(12) United States Patent
Oatley et al.

(10) Patent No.: US 12,102,069 B2
(45) Date of Patent: Oct. 1, 2024

(54) NANOS KNOCK-OUT THAT ABLATES GERMLINE CELLS

(71) Applicants: Washington State University, Pullman, WA (US); University of Maryland, College Park, MD (US); The University Court of The University of Edinburgh, Edinburgh (GB)

(72) Inventors: Jon Michael Oatley, Pullman, WA (US); Christopher Bruce Alexander Whitelaw, Biggar (GB); Simon Geoffrey Lillico, Penicuik (GB); Bhanu Prakash Telugu, Laurel, MD (US)

(73) Assignees: Washington State University, Pullman, OR (US); University of Maryland, College Park, MD (US); The University Court of The University of Edinburgh, Edinburgh (GB)

( * ) Notice: Subject to any disclaimer, the term of this patent is extended or adjusted under 35 U.S.C. 154(b) by 170 days.

(21) Appl. No.: 16/825,858

(22) Filed: Mar. 20, 2020

(65) Prior Publication Data
US 2020/0253174 A1 Aug. 13, 2020

Related U.S. Application Data

(62) Division of application No. 15/325,777, filed as application No. PCT/US2015/040379 on Jul. 14, 2015.

(60) Provisional application No. 62/023,996, filed on Jul. 14, 2014.

(51) Int. Cl.
| | | |
|---|---|---|
| A01K 67/00 | (2006.01) | |
| A01K 67/0276 | (2024.01) | |
| C12N 9/22 | (2006.01) | |
| C12N 15/90 | (2006.01) | |
| G01N 33/00 | (2006.01) | |

(52) U.S. Cl.
CPC ............ *A01K 67/0276* (2013.01); *C12N 9/22* (2013.01); *C12N 15/907* (2013.01); *C12Y 301/00* (2013.01); *A01K 2217/075* (2013.01); *A01K 2227/101* (2013.01); *A01K 2227/108* (2013.01); *A01K 2267/025* (2013.01)

(58) Field of Classification Search
CPC .......... A01K 67/0276; A01K 2217/075; A01K 2227/108; A01K 2267/025; C12N 9/22
See application file for complete search history.

(56) References Cited

U.S. PATENT DOCUMENTS

| | | |
|---|---|---|
| 5,858,354 A | 1/1999 | Brinster |
| 8,313,925 B2 * | 11/2012 | Gregory et al. |
| 8,586,526 B2 * | 11/2013 | Gregory et al. |
| 8,865,406 B2 * | 10/2014 | Zhang et al. |
| 2006/0265774 A1 * | 11/2006 | Shinohara ............... A61P 15/08 800/24 |
| 2007/0042485 A1 | 2/2007 | Heddle et al. |
| 2012/0167242 A1 | 6/2012 | Wiles et al. |
| 2012/0192298 A1 | 7/2012 | Weinstein et al. |
| 2012/0304323 A1 | 11/2012 | Lauth et al. |
| 2013/0298269 A1 | 11/2013 | Wiles et al. |
| 2014/0359796 A1 | 12/2014 | Fahrenkrug et al. |

FOREIGN PATENT DOCUMENTS

| | | |
|---|---|---|
| CN | 102638971 B | 10/2015 |
| CN | 101528924 B | 11/2015 |
| JP | 7501705 A | 2/1995 |
| JP | 2004065040 | 8/2002 |
| JP | 200628041 A | 2/2006 |
| JP | 2006115767 | 11/2006 |
| JP | 2008104401 | 5/2008 |
| WO | 9311228 A1 | 6/1993 |
| WO | 2010010862 A1 | 1/2010 |
| WO | 2014193583 A2 | 12/2014 |
| WO | 2014193583 A3 | 12/2014 |
| WO | 2015073819 A1 | 5/2015 |
| WO | 2016163386 A1 | 10/2016 |

OTHER PUBLICATIONS

Wu et al. Review: Target specificity of the CRISPR-Cas9 system. Quantitative Biology 2:59-70, (Year: 2014).*
Shmakov et al. Discovery and functional characterization of diverse Class 2 CRISPR-Cas systems. Mol. Cell 60: 385-397, 23 pages, (Year: 2015).*
Pitman et al. The fate of granulosa cells following premature oocyte loss and the development of ovarian cancers. Int. J. Dev. Biol. 56:949-958, (Year: 2012).*
Sada, Aiko et al., "The RNA-Binding Protein NANOS2 Is Required to Maintain Murine Spermatogonial Stem Cells", Science Magazine, vol. 325, pp. 1394-1398. Sep. 11, 2009.
Wang, Haoyi Dr., "One-step Generation of Knockout Pigs by Zygote Injection of CRISPR/Cas System", Cell Research, pp. 372-375. Jan. 31, 2014.
Boettcher, Paul J., et al., "The Combined Use of Embryos and Semen for Cryogenic Conservation of Mammalian Livestock Genetic Resources", Genet. Sel. Evol. 37 (2005) pp. 657-675. Jul. 6, 2005.
Hai, Tang et al., "One-Step Generation of Knockout Pigs by Zygote Injection of CRISPR/Cas System", Cell Research (2014) 24, pp. 372-375. Jan. 31, 2014.

(Continued)

*Primary Examiner* — Quang Nguyen
(74) *Attorney, Agent, or Firm* — Christensen O'Connor Johnson Kindness PLLC

(57) ABSTRACT

The present invention provides livestock animals and methods to create recipient animals for spermatogonial stem cell transplantation through modulation of the NANOS gene. In one embodiment genome editing issued to create animals with insertions or deletions (indels) that inactivate or otherwise modulate NANOS gene activity so that resulting males lack functional germ cells yet retain functional somatic cells, and females are fertile. These males can then be transplanted with donor spermatogonial stem cells and used for breeding.

10 Claims, 31 Drawing Sheets

Specification includes a Sequence Listing.

(56) References Cited

OTHER PUBLICATIONS

Park, Ki-Eun et al., "Generation of Germline Ablated Male Pigs by CRISPR/Cas9 Editing of the NANOS2 Gene", Scientific Reports, pp. 1-9, Jan. 10, 2017.
Kusz-Zamelczyk, Kamila et al., "Mutations of NANOS1, a Human Homologue of the Drosophila Morphogen, are Associated with a Lack of Germ Cells in Testes or Severe Oligo-Asthenoteratozoospermia", J Med Genet, 2013;50 pp. 187-193 Jan. 12, 2013.
Tsuda, Masayuki et al., "Conserved Role of Nanos Proteins in Germ Cell Development", Science, vol. 301, pp. 1239-1241. Aug. 29, 2003.
Lillico et al., "Live pigs produced from genome edited zygotes", Scientific Reports, vol. 3, 4 pages, Oct. 10, 2013.
Saga, Y., "Function of NANOS2 in the male germ cell lineage in mice", Cell. Mol. Life Sci., vol. 67(22), pp. 3815-3822, Nov. 2010.
"Sus scrofa chromosome 6 clone CH242-173N22, Working Draft Sequence, 4 unordered pieces", GenBank: FP102597.2, 35 pages, Aug. 19, 2009.
Suzuki et al., "Functional redundancy among NANOS proteins and a distinct role of NANOS2 during male germ cell development", Development, vol. 134, pp. 77-83, 2007.
Kusz et al., "The highly conserved NANOS2 protein", Molecular Human Reproduction, vol. 15, pp. 165-171 2009.
Kusz et al., "NANOS3 gene mutations in men with isolated sterility phenotype", Mol. Reprod. Dev., vol. 76, p. 804, 2009.
Groenen et al., "Analyses of pig genomes provide insight into porcine demography and evolution", Nature, vol. 491, pp. 393-398, 2012.
Elsik et al., "The genome sequence of taurine cattle", Science, vol. 324, pp. 522-528, 2009.
Orlando et al., "Recalibrating Equue evolution using the genome sequence of an early Middle Pleistocene horse", Nature, vol. 499, pp. 74-81, 2013.
Horii, T. and I. Hatada, "Genome Engineering Using the CRISPR/Cas System," World Journal of Medical Genetics 4(3):69-76, Aug. 2014.
Makarova, K.S., et al., "An Updated Evolutionary Classification of CRISPR-Cas Systems," Nature Review Microbiology 13(11):722-736, Nov. 2015.
Barriga, E.H., et al., "Tissue Stiffening Coordinates Morphogenesis by Triggering Collective Cell Migration In Vivo," Nature, 554(7693):523-527, Feb. 2018.
Chan C.J., et al., "Coordination of Morphogenesis and Cell-Fate Specification in Development," Current Biology, 27(18):R1024-R1035, Sep. 2017.
Chen, C et al., "ERM is Required for Transcriptional Control of the Spermatogonial Stem Cell Niche," Nature, 436:1030-1034, Aug. 2005.
Espina, J.A., et al., "Tissue Interplay During Morphogenesis," Seminars in Cell & Developmental Biology, vol. 147, Sep. 2023, pp. 12-23.
Gewiss R.L., et al., "Two Distinct Sertoli Cell States Are Regulated via Germ Cell Crosstalk," Biology of Reproduction 105(6):1591-1602, Dec. 2021.
Hyman A.A., et al., "Morphogenetic Properties of Microtubules and Mitotic Spindle Assembly," Cell, 84(3):401-410, Feb. 1996.
Jégou B., et al., "Interleukin-1, Interleukin-6 and the Germ Cell-Sertoli Cell Cross-Talk," Reproduction, Fertility and Development, 7(4):723-730, 1995.
Oatley J.M., et al., "The Germline Stem Cell Niche Unit in Mammalian Testes," Physiological Reviews 92(2):577-595, Apr. 2012.
Park, K.E., et al., "Generation of Germline Ablated Male Pigs by CRISPR/Cas9 Editing of the NANOS2 Gene," Scientific Reports, 7:40176, Jan. 2017.
Pellegrino J., et al., "Chromatin Associated Sin3a Is Essential for Male Germ Cell Lineage in the Mouse," Developmental Biology, 369(2):349-355, Sep. 2012.
Ruggiu, M. et al., "The Mouse Dazl Gene Encodes a Cytoplasmic Protein Essential for Gametogenesis," Nature, 389(6646):73-77, Oct. 1997.
Schrans-Stassen, B. H., et al., "Nature of the Spermatogenic Arrest in Dazl-/-Mice," Biology of Reproduction, 65(3):771-776 (2001).
Wu S., et al., "Crosstalk Between Sertoli and Germ Cells in Male Fertility," Trends in Molecular Medicine 26(2):215-231, Feb. 2020.
Yokonishi, T., et al., "Sertoli Cell Ablation and Replacement of the Spermatogonial Niche in Mouse," Nature Communications, 11:40, Jan. 2020.
Kanatsu-Shinohara, M., et al., "Functional Assessment of Self-Renewal Activity of Male Germline Stem Cells Following Cytotoxic Damage and Serial Transplantation," Biology of Reproduction 68(5):1801-1807, May 2003.
Bucci, M.R., et al., "Effects of Busulfan on Murine Spermatogenesis: Cytotoxicity, Sterility, Sperm Abnormalities, and Dominant Lethal Mutations," Mutation Research 176(2): 259-268, Feb. 1987.
Ryu, B-Y., et al., "Effects of Aging and Niche Microenvironment on Spermatogonial Stem Cell Self-Renewal," Stem Cells 24(6):1505-1511, Jun. 2006.

* cited by examiner

```
agttaactaagcttTGTACAAAAAGCAGGCTTTAAAGGAACCAATTCAGTCGACTGGATCCGGTACCAAGGTCGGGCAGGAAGAGGGCCTATTTCCCATGA
TTCCTTCATATTTGCATATACGATACAAGGCTGTTAGAGAGATAATTGACTGTAAACACAAAGATAATTAGTACAAAATACGTGACGTAG
AAAGTAATAATTCTTGGGTAGTTTGCAGTTTAAAATTATGTTTAAAATGA CTATCATATGCTAACCGTAACTTGAAAGTATTTCGATTTCTTGGCTTT
ATATATCTTGTGGAAAGGACGAAACACCgaatcgtcgacaagggccagGTTTTAGAGCTAGAAATAGCAAGTTAAAATAAGGCTAGTCCGTTATCAACTTGAA
AAAGTGGCACCGAGTCGGTGCTTTTTTCTAGACCCAGCTTTCTTGTACAAAGTTGGCATTActcgagatccact
```

FIG. 3A

```
agttaactaagcttTGTA CAAAAAGCAGGCTTTAAAGGAACCAATTCAGTCGACTGGATCCGGTACCAAGGTCGGGCAGGAAGAGGGCCTATTTCCCATGA
TTCCTTCATATTTGCATATACGATACAAGGCTGTTAGAGAGATAATTGACTGTAAACACAAAGATATTAGTACAAAATACGTGACGTAG
AAAGTAATAATTCTTGGGTAGTTTGCAGTTTAAAATTATGTTTAAAATGGACTATCATATGTTTAAAAATGGACTATCATATGCTTACCGT AACTTGAAAGTATTTCGATTTCTTGGCTTT
ATATATCTTGTGGAAAGGACGAAACACCgtggccctttgtcgacgattcgTTTTAGAGCTAGAAATAGCAAGTTAAAATAAGGCTAGTCCGTTATCAACTTGAAA
AAGTGGCACCGAGTCGGTGCTTTTTTCTAGACCCAGCTTTCTTGTACAAAGTTGGCATTActcgagatccact
```

FIG. 5C2 acacccgctgacgcgccctgacgggcttgtctgctcccgagcatccgttacagacaagctgtgaccgtctccggagctgcatgtgtcagaggttttcaccgtcatcacgaaacgcgcgagacg aaagggcctcg
tgatacgcctattttataggttaatgtcatgataataatggttttcttagacgtcaggtggcacttttcggggaaatgtgcgcggaacccctattgttatttttctaaatacattcaaatatgt atccgctcatgagac
aataacccctgataaatgcttcaataatattgaaaaaggaagagagtatgattcaacagcgatgaagaaccttcgtgtcgccttatccctttttgccgcatttttgctcac ccagaaacgctggtgaaagtaaaa
gatgctgaaggatcagttggctgcacgagtggttacatcgaactgatctccatcactattttctgagatcctgagagtttcgccccgaagaacgtttccaatgatgagcactttaaagttctgct atgtggcggcgta
ttatccgtattgacgccggcaagagcaactggtcgtccgcatatacactattctgagaatgactggttgagtactcaccagtcagaaaaagc atcttacgatggcatgacagtaagaattatgcagtgctgc
cataaccatgagtgatgataacactgcggccaacttacttctgacaacgttgcgcaaacattaactggcga actactactctagtctcccggcaacaattaatagactggtaagcccctccgtat cgtagttatctac
gccatccaaacgacgagcgtgacaccacgatgcctagcagtgcaacatggcaatgtgcgtatcattgcaggccagatgggcagtggtaatcgtgaagccagccactcagtgattacctcattttaa
gcaggccacttctgcctcggcctttccggctgtcggtttattgtgataatctgagatcgctgagtagcgtgagcgtggaagccatggtaactgtcagaccaagttactcatatatacttagattgattaaaactcatttttaa
acgacggggagtcaggcaactatggcaatatgacgaaatagacagatgctgagatagtgcc tcactgattaagcattgtaactgtcagaccccgtagaaaaagatcaaaggatcctctcttgagatcctt tttctgcgcgtaat
tttaaaaggatctaggtgaagatctcttttttgataatctcatgaccaaatcccttaacgtgagtttcgttccactgagcgtcagaccccgtagaacgcgtagaaaaactactgtccttcttctagtgtagccgta
ctgtcgttgtcaaacaaaaaaccgctaccagcggtggtttgtttgccgggttcagcagagctacccaactcttttttccgaaggtaactgccttcagcgagcgcagataccaaatactgtccttctagtagccgta
gttaggccaccacttcaagaactctgtagcaccgcctacatacctcgtctctgctaatcctgttacagtggctgctgccagtggcgataagtcgtgtcttaccgggttggactgaagacgatagt taccggataagc
gcagcggtcggctgaacggggggttcgtgcacacagcccagcttggagcgaacgacctacaccgaactgagatacctacagcgtgagctatgagaaagcgccacgcttccgaagggagaaaggcggacag
gtatccggtaagcggcaggggtcggaacaggagagcgcacagaggagcgcacggagagcgcacggagcacgccggaaacgcctggtatcttatagtcctgtcgggtttcgccacctctgacttgagcgtcgatttttgtgat gtcgtcagggg
gcggagcagctatggaaaaacgccagcaacgcggcctttttacggttcctggccttttgctggcctttgctcacatgt

FIG. 5C3 pSL32 & pSL38

```
WT      TGGGCCCTTTAAATCCTAAGCTCCACCTTTGCTTAGAAGGGTCTCTTTGGGAATATAAAAGGGGGTGCAGTTCC-//-TGA
Clone 1 TGGGCCCTTTAAATCCTAAGCTCCACCTTTGCTTAGAAGGGTCTTTTGGGAATATATAA--------------------
Clone 2 TGGGCCCTTTAAATCCTAAGCTCCACCTTTGCTTAGAAGGGTCTTTTGGGAATATATAA--------------------
Clone 3 TGGGCCCTTTAAATCCTAAGCTCCACCTTTGCTTAGAAGGGTCTTAGAAGGGTCTTT----------------------
Clone 4 TGGGCCCTTTAAATCCTAAGCTCCACCTTTGCTTAGAAGGGTCTTAGAAGGGTCTTT----------------------
Clone 5 TGGGCCCTTTAAATCCTAAGCTCCACCTTTGCTTAGAAGGGTCTTAGAAGGGTCTTT----------------------

WT      GCCAAGTGGTGCTGCACTGATCCAGAGTCGGGGGGCAAGGGTTGGAGACCCAAGGGACTGGGGAGCCGAGACCCGGGCC
Clone 1 ----------------------------------------CAAGGGACTGGGGAGCCGAGACCCGGGCC
Clone 2 ----------------------------------------CAAGGGACTGGGGAGCCGAGACCCGGGCC
Clone 3 -------------------------------------GGGACTGGGGAGCCGAGACCCGGGCC
Clone 4 -------------------------------------GGGACTGGGGAGCCGAGACCCGGGCC
Clone 5 ----------------------------------------GGGAGCCGAGACCCGGGCC WT      CCATGTGGAGCAGGATCAGGGGCAGGGGCGGACGCGGGGGCCGGCGGGGG
Clone 1 CCATGTGGAGCAGGATCAGGGGCAGGGGCGGACGCGGGGGCCGGCGGGGG
Clone 2 CCATGTGGAGCAGGATCAGGGGCAGGGGCGGACGCGGGGGCCGGCGGGGG
Clone 3 CCATGTGGAGCAGGATCAGGGGCAGGGGCGGACGCGGGGGCCGGCGGGGG
Clone 4 CCATGTGGAGCAGGATCAGGGGCAGGGGCGGACGCGGGGGCCGGCGGGGG
Clone 5 CCATGTGGAGCAGGATCAGGGGCAGGGGCGGACGCGGGGGCCGGCGGGGG
```

FIG. 8 pSL32 & pSL39

```
WT       TGGGCCCTTTAAATCCTAAGCTCCACCTTTGCTTAGAAGGGTCTTTTGGGAATATAAAAGGGGTGCAGTTCC-//-TGA
Clone 1  TGGGCCCTTTAAATCCTAAGCTCCACCTTTGCTTAGAAGGGTCTTTTGGG-------------GGTGCAGTTCC-//-TGA
Clone 2  TGGGCCCTTTAAATCCTAAGCTCCACCTTTGCTTAGAAGGGTCTTTGGGAATATAA----------------------
Clone 3  TGGGCCCTTTAAATCCTAAGCTCCACCTTTGCTTAGAAGGTCTTTGGGAATATAAA----------------------
Clone 4  TGGGCCCTTTAAATCCTAAGCTCCACCTTTGCTTAGAAGGTCTTTGGGA--------------GTGCAGTTCC-----
Clone 5  TGGGCCCTTTAAATCCTAAGCTCCACCTTTGCTTAGAAGGTCTTTGGGAATATAA-----------------------

WT       GCCAAGTGGTGCTGGCACTGATCCAGAGTCGGGGGCAAGGGTTGGAGACCCAAGGGACTGGGGAGCCCGAGACCCGGGCC
Clone 1  GCCAAGTGGTGCTGGCACTGATCCAGAGTCGGGGCAAGGCGGAGACCCAAGGGACTGGGGAGC----(-275bp)-
Clone 2  ---------------------------------------------------------------------------
Clone 3  ---------------------------------------------------------------------------
Clone 4  ---------------------------------------------------------------------------
Clone 5  ---------------------------------------------------------------------------

WT       CCATGTGGAGCAGGATCAGGGGCAGGGGCGGACGCGGGGCCGGCGGGG--------
Clone 1  -CATGTGGAGCAGGATCAGGGGCAGGGGCGGACGCGGGGCCGGCGGGG--------
Clone 2  -CATGTGGAGCAGGATCAGGGGCAGGGGCGGACGCGGGGCCGGCGGGGG-------
Clone 3  -CATGTGGAGCAGGATCAGGGGCAGGGGCGGACGCGGGGCCGGCGGGGG-------
Clone 4  --ATGTGGAGCAGGATCAGGGGCAGGGGCGGACGCGGGGCCGGCGGGGG-------
Clone 5  -CATGTGGAGCAGGATCAGGGGCAGGGGCGGACGCGGGGCCGGCGGGGG-------
```

FIG. 8 (CONT.)

pSL32 & pSL42

```
WT       TGGGCCCTTTAAATCCTAAGCTCCACCTTTGCTTAGAAGGGTCTTTTGGGAATATAAAAGGGGGTGCAGTTCC-//-TGA
Clone 1  TGGGCCCTTTAAATCCTAAGCTCCACCTTTGCTTAGAAGGGTCT--------------------------AAGG-------
Clone 2  TGGGCCCTTTAAATCCTAAGCTCCACCTTTGCTTAGAAGGGTCTTTTGGGAATATAA-----------------------
Clone 3  TGGGCCCTTTAAATCCTAAGCTCCACCTTTGCTTAGAAGGGTCTTTTGGGAATATAA-----------------------
Clone 4  TGGGCCCTTTAAATCCTAAGCTCCACCTTTGCTTAGAAGGG---------------------------------------
Clone 5  TGGGCCCTTTAAATCCTAAGCTCCACCTTTGCTTAGAAGG----------------------------------------

WT       GCCAAGTGGTGCTGGCACTGATCCAGAGTCGGGGCAAGGGTTGGAGACCCAAGGGACTGGGGAGCCGAGACCCGGGCC
Clone 1  --------------------------------------------------------------------------------
Clone 2  --------------------------------------------------------------------------------
Clone 3  --------------------------------------------------------------------------------
Clone 4  --------------------------------------------------------------------------------
Clone 5  --------------------------------------------------------------------------------

WT       CCATGTGGAGCAGGATCAGGGGCCAGGGGCGGACGCGGGGCCGGCGGGGG
Clone 1  ---------------------------(-445bp)--------------
Clone 2  -----------------TCAGGGGCCAGGGGCGGACGCGGGGCCGGCGGGGG
Clone 3  ---------CAGGGGCCAGGGGCGGACGCGGGGCCGGCGGGGG
Clone 4  ------------------------------------GGGG
Clone 5  -----------------CGGACGCGGGGCCGGCGGGGG
```

FIG. 8 (CONT.)

```
pSL33 & pSL38

WT        TGGGCCCTTTAAATCCTAAGCTCCACCTTTGCTTAGAAGGGTCTTTTGGGAATATAAAGNGGGTGCATGGCC-//-TGA
Clone 1   TGGGCCCTTTAAATCCTAAGCTCCACCTTTGCTTAGAAGGGTCTTTTGGGAATATAA--------------------
Clone 2   TGGGCCCTTTAAATCCTAAGCTCCACCTTTGCTTAGAAGGGTCTTTTGGGAATATAA--------------------
Clone 3   TGGGCCCTTTAAATCCTAAGCTCCACCTTTGCTTAGAAGGGTCTTTTGGGAATATAA--------------------
Clone 4   TGGGCCCTTTAAATCCTAAGCTCCACCTTTGCTTAGAAGGGTCTTTTGGGAATATAA--------------------
Clone 5   TGGGCCCTTTAAATCCTAAGCTCCACCTTTGCTTAGAAGGGTCTTTTGGGAATATAA--------------------

WT        GCCAAGTGGTGCTGGCACTGATCCAGAGTCGGGGCAAGGGTTGGAGACCCAAGGGACTGGGGAGCCGAGACCCGGGCC
Clone 1   -----------------------------------------------CAAGGGACTGGGGAGCCGAGACCCGGGCC
Clone 2   -----------------------------------------------CAAGGGACTGGGGAGCCGAGACCCGGGCC
Clone 3   -----------------------------------------------CAAGGGACTGGGGAGCCGAGACCCGGGCC
Clone 4   -----------------------------------------------CAAGGGACTGGGGAGCCGAGACCCGGGCC
Clone 5   -----------------------------------------------CAAGGGACTGGGGAGCCGAGACCCGGGCC WT        CCATGTGGAGCAGGATCAGGGGCAGGGCGGACGCGCGGGGCCGGCGGGGG
Clone 1   CCATGTGGAGCAGGATCAGGGGCAGGGCGGACGCGCGGGGCCGGCGGGGG
Clone 2   CCATGTGGAGCAGGATCAGGGGCAGGGCGGACGCGCGGGGCCGGCGGGGG
Clone 3   CCATGTGGAGCAGGATCAGGGGCAGGGCGGACGCGCGGGGCCGGCGGGGG
Clone 4   CCATGTGGAGCAGGATCAGGGGCAGGGCGGACGCGCGGGGCCGGCGGGGG
Clone 5   CCATGTGGAGCAGGATCAGGGGCAGGGCGGACGCGCGGGGCCGGCGGGGG
```

FIG. 8 (CONT.)

pSL33 & pSL39

| | |
|---|---|
| WT | TGGGCCCCTTTAAATCCTAAGCTCCACCTTTGCTTAGAAGGGTCTCTTTGGGAATATAAAAAGGGGGTGCATGGCC-//-TGA |
| Clone 1 | TGGGCCCCTTTAAATCCTAAGCTCCACCTTTGCTTAGAAGGGTCTCTTTGGGAATATAT-------------------- |
| Clone 2 | TGGGCCCCTTTAAATCCTAAGCTCCACCTTTGCTTAGAAGGGTCTCTTTGGGAATATAA-------------------- |
| Clone 3 | TGGGCCCCTTTAAATCCTAAGCTCCACCTTTGCTTAGAAGGGTCTCTTTGGGAATAT---------------------- |
| Clone 4 | TGGGCCCCTTTAAATCCTAAGCTCCACCTTTGCTTAGAAGGGTCTCTTTGGGA------------------------- |
| Clone 5 | TGGGCCCCTTTAAATCCTAAGCTCCACCTTTGCTTAGAAGGGTCTCTTTGGGAATATAA------------------- |

| | |
|---|---|
| WT | GCCAAGTGGTGCTGGCACTGATCCAGAGTCGGGGCAAGGGTTGGAGACCCAAGGGACTGGGGAGCCGAGACCCGGGCC |
| Clone 1 | -------------------------------------------------------------------------- |
| Clone 2 | -------------------------------------------------------------------------- |
| Clone 3 | -------------------------------------------------------------------------- |
| Clone 4 | -------------------------------------------------------------------------- |
| Clone 5 | -------------------------------------------------------------------------- |

| | |
|---|---|
| WT | CCATGTGGAGCAGGATCAGGGGCAGGGCGGACGCGGGGGCCCGGCGGCGGGGG |
| Clone 1 | ----GTGGAGCAGGATCAGGGGCAGGGCGGACGCGGGGGCCCGGCGGCGGGGG |
| Clone 2 | -CATGTGGAGCAGGATCAGGGGCAGGGCGGACGCGGGGGCCCGGCGGCGGGGG |
| Clone 3 | -------------GATCAGGGGCAGGGCGGACGCGGGGGCCCGGCGGCGGGGG |
| Clone 4 | ---------GCAGGATCAGGGGCAGGGCGGACGCGGGGGCCCGGCGGCGGGGG |
| Clone 5 | -CATGTGGAGCAGGATCAGGGGCAGGGCGGACGCGGGGGCCCGGCGGCGGGGG |

FIG. 8
(CONT.)

pSL33 & pSL42

```
WT       TGGGCCCCTTTAAATCCTAAGCTCCACCTTTGCTTAGAAGGGTCTTTTGGGAATATAAAGGGGGTGCATGGCC-//-TGA
Clone 1  TGGGCCCCTTTAAATCCTAAGCTCCACCTTTGCTTAGAAGG---------------------------------------
Clone 2  TGGGCCCCTTTAAATCCTAAGCTCCACCTTTGCTTAGAAGGTCTTTGG--------------------------------
Clone 3  TGGGCCCCTTTAAATCCTAAGCTCCACCTTTGCTTAGAAGGTCTTTGGGAATATAA------------------------
Clone 4  TGGGCCCCTTTAAATCCTAAGCTCCACCTTTGCTTAGAAGG---------------------------------------
Clone 5  TGGGCCCCTTTAAATCCTAAGCTCCACCTTTGCTTAGAAG----------------------------------------

WT       GCCAAGTGGTGCTGGCACTGATCCAGAGTCGGGGCAAGGGTTGGAGACCCAAGGGACTGGGGAGCCGAGACCCGGGCC
Clone 1  ------------------------------------------------------------------------------
Clone 2  ------------------------------------------------------------------------------
Clone 3  ------------------------------------------------------------------------------
Clone 4  ------------------------------------------------------------------------------
Clone 5  -------TGGTGCTGGCACTGATCCAGAGTCGGGGCAAGGTTGGAGACCCAAGGGACTGGGGAGCCGAGACCCGGGCC WT       CCATGTGGAGCAGGATCAGGGGCCAGGGGCCAGGGGCGAGGGGCGGACGCGGGGCCGGGGGG-----------------
Clone 1  -----------------------------GCAGGGGCGAGGGGCGGACGCGGGGCCGGGGGG-----------------
Clone 2  ----------------------------CGGACGCGGGGCCGGGGGG-----------------
Clone 3  ---------------------TCAGGGGCCAGGGGCGAGGGGCGGACGCGGGGCCGGGGGG-----------------
Clone 4  ---------------------------GCAGGGGCGAGGGGCGGACGCGGGGCCGGGGGG-----------------
Clone 5  CCATGTGGAGCCAGG---------(-29bp)------------------------------------------------
```

FIG. 8
*(CONT.)*

| NANOS (CRISPR) | |
|---|---|
| Nanos2 | TTGGCTCCCCGGTGCCCGGCCCTCTGGCCCTTGTCGACGATTCTGGATCAGTCCC |
| N1-1   | TTGGCTCCCCGGTGCCCGGGGCCTCTG--CCCTTGTCGACGATTCTGGATCAGTCCC |
| N1-2   | TTGGCTCCCCGGTGCCCGGGGCCTCTG---TCGACGATTCTGGATCAGTCCC |
| N3-2   | TTGGCTCCCCGGTGCCCGGGGCCTCTG---TCGACGATTCTGGATCAGTCCC |
| N3-3   | TTGGCTCCCCGGTGCCCGGGGCCTCTGG-CCCTTGTCGACGATTCTGGATCAGTCCC |
| N5-2   | TTGGCTCCCCGGTGCCCGGGGCCTCTG--CCCTTGTCCACAATTCTGGATCATTCCC |
| N5-3   | TTGGCTCCCCGGTGCCCGGGGCCTCTG--TCGACGATTCTGGATCAGTCCC |
| N6-1   | TTGGCTCCCCGGTGCCCGGGGCCTGC-CGGGCCCTTGTCGACGATTCTGGATCAGTCCC |
| N7-2   | TTGGCTCCCCGGTGCCCGGGGCCTCTG--CCCTTGTCGACGATTCTGGATCAGTCCC |
| N7-3   | TTGGCTCCCCGGTGCCCGGGGCCTCTG--CCCTTGTCGACGATTCTGGATCAGTCCC |
| N10-2  | TTGGCTCCCCGGTGCCCGGGGCCTCTG--GTCGTCGACGATTCTGGATCAGTCCC |
| N11-2  | TTGGCTCCCCGGTGCCCGGGGCCTCTC--CCCTTGTCGACGATTCTGGATCAGTCCC |
| N12-2  | TTGGCTCCCCGGTGCCCGGGGCCTGC--CCCTTGTCGTCAATTCTGGATCAGTCCC |
| N12-3  | TTGGCTCCCCGGTGCCCGGGGCCTGC------TCGACAATTCTGGATCAGTCCC |

FIG. 9D

```
NANOS  CCCGGTGCCCGGGGCCCTCTGGCCCTTGTCGACGATTCTGGATCAGTCCCAACACCACCTGG
NN6-1  CCCGGTGCCCGGGGCCCTCTGGCCCTTGTCGACGATCAGTCCCAACACCACCTGG
NN7-1  ------------------------------------------------------
NN7-2  ------------------------------------------------------
```

FIG. 10A

```
Nanos2   CTCAGGTCTCTTGGCTCCCCGGTGCCCGGGGCCCTCTGCCCCTTGTCGACGATTCTGGATCAGT
N3-1-3   CTCAGGTCTCTTGGCTCCCCGGTGCCCGGGGCCCTCTG--CCCCTTGTCGACGATTCTGGATCAGT
N3-2-3   CTCAGGTCTCTTGGCTCCCCGGTGCCCGGGGCCCTCTG--CCCCTTGTCGACGATTCTGGATCAGT
N3-6-2   CTCAGGTCTCTTGGCTCCCCGGTGCCCGGGGCCTGCC--CGGCCCCTTGTCGACGATTCTGGATCAGT
N3-7-3   ATCAGNNCTTGGCTCCCCGGTGCCCGGGGCCTGCC--CGGCCCCTTGTCGACGATTCTGGATCAGT
N3-8-3   CTCAGGTCTCTTGGCTCCCCGGTGCCCGGGGCCCG----------GGGCCCTGTCGACGATTCTGGATCAGT
N3-10-2  CTCAGGTCTCTTGGCTCCCCGGTGCCCGGGGCCCG----------GGGCCCTGTCGACGATTCTGGATCAGT
N3-12-2  CTCAGGTCTCTTGGCTCCCCGGTGCCCGGGGCCCTCTGCCCCTTGTCGAC---TTCTGGATCAGT
N3-12-3  CTCAGGTCTCTTGGCTCCCCGGTGCCCGGGGCCCTCTG--CCCCTTGTCGACGATTCTGGATCAGT
```

FIG. 10B

Nickase pair:

sgRNA1: GCACCAGCTGAAGACACCGGAGG"
sgRNA2: GCTGGTGCCGAGGAGTACACGTGG"

```
Nanos: GAATCTCGCCACGTGTACTCCTCGCACCAGCTGAAGACACCGGAGGGCGTGGTGGTGGTGTCCCAT
N2-3:  GAATCTCGCCACGTGTACTCCTCCTCGCACCAGCTGAAGACACCGGAGGGCGTGGTGGTGGTGTCCCAT
N3-1:  GAATCTCGCCACGTGTACTCCTCCTCGCACCAGCTGAAGACACCGGAGACACCGGAGGGCGTGGTGGTGGTGTCCCAT
N4-2:  GAATCTCGCCACGTGTACTCCTCCTCGCACCAGCTGAAGACACCGGAGGGCGTGGTGGTGTCCCAT
N5-2:  GAATCTCGCCACGTGTACTCCTCCTCGCACCAGCTGAAGACACCGGAGGGCGTGGTGGTGTCCCAT
N6-3:  GAATCTCGCCACGTGTACTCCTCCTCGCACCAGCTGAAGACACCGGAGGGCGTGGTGGTGGTGTCCCAT
N7-1:  GAATCTCGCCACGTGTACTCCTCCTCGCACCAGCTGAAGACACCGGAGGGCGTGGTGGTGGTGTCCCAT
```

Guide RNA sequence:

GATCAGTCCCAACACCACCTGG (reverse orientation)

NANOS2 ORF:

```
  1 ATGCAGCTGC CACCCTTTGA CATGTGGAAG GACTACTTCA ACCTGAGCCA
    M  Q  L  P   P  F  D   M  W  K    D  Y  F  N   L  S  Q

51 GGTGGTGTTG GGACTGATCC AGAATCGTCG ACAAGGGCCA GAGGCCCCGG
    V  V  L    G  L  I  Q  N  R  R    Q  G  P    E  A  P  G

101 GCACCGGGGA GCCAAGACCT GAGCCCCAC TGGAGCAGGA CCAGGGCCCG
    T  G  E    P  R  P    E  P  P  L   E  Q  D   Q  G  P

151 GGAGAGCGGG GGGCCAGCGG GGGGCTGGCC ACCCTGTGCA ACTTTTGCAA
    G  E  R  G   A  S  G    G  L  A    T  L  C  N   F  C  K

201 ACACAATGGG GAATCTCGCC ACGTGTACTC CTCGCACCAG CTGAAGACAC
    H  N  G    E  S  R  H   V  Y  S    S  H  Q    L  K  T  P

251 CGGAGGGCGT GGTGGTGTGT CCCATCCTAC GACACTATGT GTGTCCCCTG
    E  G  V    V  V  C    P  I  L  R   H  Y  V    C  P  L

301 TGCGGGGCCA CCGGTGACCA GGCTCACACA CTCAAGTACT GCCCGCTCAA
    C  G  A    T  G  D  Q  A  H  T    L  K  Y  C   P  L  N

351 CGGCGGCCAG CAGTCTCTCT ATCGCCGCAG TGGGCGCAAT TCAGCCGGCC
    G  G  Q    Q  S  L  Y   R  R  S    G  R  N    S  A  G  R

401 GCAAGGTCAA GCGCTGA
    K  V  K    R  *
```

FIG. 13

1st litter

1 piglet (Male)-Mosaic 3 alleles
```
Nanos WT       CTACTTCAACCTGAGCCAGGTGGTGTTGGGACTGATCCAGAA
Nanos pig 1-1  CTACTTCAACCTGAGCCAGGT-----TGGGACTGATCCAGAA
Nanos pig 1-2  CTACTTCAACCTGAGCCAGGTG---TTGGGACTGATCCAGAA
Nanos pig 1-3  CTACTTCAACCTGAGCCAGGAC---TGGGACTGATCCAGAA
```

2 piglet (Male)- - Tag #137 (homozygous Knockout)
```
Nanos WT       CTACTTCAACCTGAGCCAGGTGG-TGTTGGGACTGATCCAGAA
Nanos pig 2-1  CTACTTCAACCTGAGCCAGGTGGGTGTTGGGACTGATCCAGAA
Nanos pig 2-4  CTACTTCAACCTGAGCCAGGTG--TGTTGGGACTGATCCAGAA
```

3 piglet (Female)
```
Nanos WT       CTACTTCAACCTGAGCCAGGTGGTGTTGGGACTGATCCAGAA
Nanos pig 3-1  CTACTTCAACCTGAGCCAGGT-----TGGGACCGATCCAGAA
```

4 piglet (Female)
```
Nanos WT       CTACTTCAACCTGAGCCAGGTGGTGTTGGGACTGATCCAGAA
Nanos pig 4-1  CTACTTCAACCTGAGCCAGGTG---TTGGGACTGATCCAGAA
Nanos pig 4-2  CTACTTCAACCTGAGCCAGGTG---TTGGGACTGATCCAGAA
```

2nd litter

1 piglet (Male)
```
Nanos WT        CTACTTCAACCTGAGCCAGGTGGTGTTGGGACTGATCCAGAA
Nanos pig 10-1  CTACTTCAACCTGAGCCAGG----------ACTGATCCAGAA
Nanos pig 10-2  CTACTTCAACCTGAGCCAGGTG---TTGGGACTGATCCAGAA
```

2 piglet (Male)
```
Nanos WT        CTACTTCAACCTGAGCCAGGTGGTGTTGGGACTGATCCAGAA
Nanos pig 11-1  CTACTTCAACCTGAGCCAGGTGT----TGGGACTGATCCAGAA
Nanos pig 11-4  CTACTTCAACCTGAGCCAGGT-----TGGGACTGATCCAGAA
```

3 piglet (Female)
```
Nanos WT        CTACTTCAACCTGAGCCAGGT-G--GTGTTGGGACTGATCCAGAA
Nanos pig 12-1  CTACTTCAACCTGAGTCAGGT------GTTGGGACTGATCCAGAA
Nanos pig 12-2  CTACTTCAACCTAAGCCAGGTTGAAGTGTTGGGACTGATCCAGAA
```

FIG. 14A

3rd litter

1 piglet (Female)
Nanos WT    CTACTTCAACCTGAGCCAGGTGGTGTTGGGACTGATCCAGAA
Allele-1    CTACTTCAACCTGAGCCAGGTG---TTGGGACTGATCCAGAA
Allele-2    CTACTTCAACCTGAGCCAGGTG-TGTTGGGACTGATCCAGAA

2 piglet (Female)
Allele-1    CTACCTCAACCTGAGCCAGG-GGTG---GGACTGATCCAGAA
Allele-2    CTACTTCAACCTGAGCCTGGT-GTGTTGGGACTGATCCAGAA

3 piglet (Female)
Allele-1    CTACTTCAACCTGAGCCAGGTG---TTGGGACTGATCCAGAA
Allele-2    CTACTTCAACCTGAGCCAGGTG---TTGGGACTGATCCAGAA

4 piglet (Male) - Tag #146 (homozygous Knockout)
Allele-1    CTACTTCAACCTGAGCCAGGTC----TGGGACTGATCCAGAA
Allele-2    ---150bp Deletion---------TGGGACTGATCCAGAA

5 piglet (Male)
Allele-1    CTACTTCAACCTGAGCCAGGTTGAAGTGTTGGGACTGATCCAGAA
Allele-2    CTACTTCAACCTGAGCCAGGT------GTTGGGACTGATCCAGAA

6 piglet (Male)
Allele-1    CTACTTCAACCTGAGCCAGGTGT---TGGGACTGATCCAGAA
Allele-2    CTACTTCAACCTGAGCCAGGTGT----TGGGACTGATCCAGAA

7 piglet (Male)
Allele-1    CTACTTCAACCTGAGCCAGGT-----TGGGACTGATCCAGAA
Allele-2    CTACTTCAACCTGAGCCAGGT-----TGGGACTGATCCAGAA

8 piglet (Male) - Tag #144 (homozygous Knockout)
Allele-1    CTACTTCAACCTGAGCCAGGTG-TGTTGGGACTGATCAATAA
Allele-2    CTACTTCAACCTGAGCCAGTGT----TGGGACTGATCCAGAA

9 piglet (Male)
Allele-1    CTACTTCAACCTGAGCCAGGTG---TTGGGACTGATCCAGAA
Allele-2    CTACTTCAACCTGAGCCAGGCGGGGTTGGGACTGATCCAGAA

10 piglet (Male)
Nanos WT    CTACTTCAACCTGAGCCAGGTGGTGTTGGGACTGATCCAGAA
Allele-1    CTACTTCAACCTGAGCCAGGTGTT---GGGACTGATCCAGAA
Allele-2    CTACTTCAACCTGAGCCAGGT--T---GGGACTGATCCAGAA

11 piglet (Male) - Tag #251 (homozygous Knockout)
Nanos WT    CTACTTCAACCTGAGCCAGGTGGTGTTGGGACTGATCCAGAA
Allele-1    CTACTTCAACCTGAGCCAGGTG-TGTTGGGACTGATCCAGAA
Allele-2    CTACTTCAACCTGAGCCAG--------------------AA

*FIG. 14B*

Genotype of NANOS2 null male piglet

```
Nanos WT   ATCCAGAATCGTCGACAAGGGCCAGAGGCCCGGGCACCGGGGAGCCAAGA
Allele 1   ATCCAGAATCGTCGACAAGGGCC----------CCGGGCACCGGGGAGCCAAGA
Allele 2   ATCCAGAATCGTCGACAAGGGCC----------CCGGGCACCGGGGAGCCAAGA
```

Genotype of NANOS2 null female piglets

```
Nanos WT   ATCCAGAATCGTCGACAAGGGCCAGAGGCCCCGGGCACCGGGGAGCCAAGA
Allele 1   ATCCAGAATCGTCGACAGGG-AGAGCCCCGGGCACCGGGGAGCCAAGA
Allele 2   ATCCAGAATCGTCGA----------GGCCCCGGGCACCGGGGAGCCAAGA
```

FIG. 15

SEQUENCE LISTING

```
<160> NUMBER OF SEQ ID NOS: 204

<210> SEQ ID NO 1
<211> LENGTH: 417
<212> TYPE: DNA
<213> ORGANISM: Sus scrofa

<400> SEQUENCE: 1
atgcagctgc cacccttga catgtggaag gactacttca acctgagcca ggtggtgttg     60
ggactgatcc agaatcgtcg acaagggcca gaggccccgg gcaccgggga gccaagacct    120
gagcccccac tggagcagga ccaggcccg ggagagcggg gggccagcgg ggggctggcc     180
accctgtgca acttttgcaa acacaatggg gaatctcgcc acgtgtactc ctcgcaccag    240
ctgaagacac cggagggcgt ggtggtgtgt cccatcctac gacactatgt gtgtcccctg    300
tgcggggcca ccggtgacca ggctcacaca ctcaagtact gcccgctcaa cggcggccag    360
cagtctctct atcgccgcag tgggcgcaat tcagccggcc gcaaggtcaa gcgctga       417

<210> SEQ ID NO 2
<211> LENGTH: 138
<212> TYPE: PRT
<213> ORGANISM: Sus scrofa

<400> SEQUENCE: 2

Met Gln Leu Pro Pro Phe Asp Met Trp Lys Asp Tyr Phe Asn Leu Ser
1               5                   10                  15

Gln Val Val Leu Gly Leu Ile Gln Asn Arg Arg Gln Gly Pro Glu Ala
            20                  25                  30

Pro Gly Thr Gly Glu Pro Arg Pro Glu Pro Leu Glu Gln Asp Gln
        35                  40                  45

Gly Pro Gly Glu Arg Gly Ala Ser Gly Gly Leu Ala Thr Leu Cys Asn
    50                  55                  60

Phe Cys Lys His Asn Gly Glu Ser Arg His Val Tyr Ser Ser His Gln
65                  70                  75                  80

Leu Lys Thr Pro Glu Gly Val Val Val Cys Pro Ile Leu Arg His Tyr
            85                  90                  95

Val Cys Pro Leu Cys Gly Ala Thr Gly Asp Gln Ala His Thr Leu Lys
            100                 105                 110
```

```
Tyr Cys Pro Leu Asn Gly Gly Gln Gln Ser Leu Tyr Arg Arg Ser Gly
            115                 120                 125

Arg Asn Ser Ala Gly Arg Lys Val Lys Arg
        130                 135

<210> SEQ ID NO 3
<211> LENGTH: 1073
<212> TYPE: DNA
<213> ORGANISM: Sus scrofa

<400> SEQUENCE: 3
cagcccaccc agggaccatg cattcctttg gcaggtgcat ttttggagga gcagcagcaa      60 gccccctgt gacaataagg aacctcccac agcctgctcc tccctcttca cacccccttg     120
gaggtataag gagggaactg acagcccaga ctcctgggct ccagagagag aaagggaggg     180 gcaggggaa ggggatagaa ggacgatctt tggggtggct gggtttcttc tctctctctg     240 cccttcacc tggtacactt tgcccagcca tggggacctt caacctgtgg acagattacc     300
tgggtttggc acgcctggtg ggggctctgc gtggggaaga ggaacctgag acgaggctgg     360 accccagcc agcaccagtg ccaggaccag agggtcagag gcccagcccg aatcctcac      420 cagctcctga acgcctgtgc tctttctgca aacataatgg cgaatcccgg ccatctacc     480 agtcccacgt gctcaaggat gaagcgggcc gagttctgtg ccccattctt cgagactacg     540
tgtgccccca gtgcggtgcc acgcgcagc gtgcccatac ccgccgcttc tgccctctca     600
ccagccaggg ctacacctct gtctacagct acaccacccg caactcggcc ggcaagaagc     660
tggcccgccc ggacaaggcg aggacacagg actctggaca tcggcgagga ggaggaggag     720
gaggtgccag cacaggttcc aaaggtgccg ggaagtcttc tggaacttct ccgtctccct     780
gctgtccctc cacttctgcc taagaggctg gcgcgagcag gacggagatg ctgccttcac     840
ctggggatgg ggacccaggc tcagtggagg ctgggtttca gggacgacct acccttcgcg     900
gatccgcccc tgcccccagc ctgggagccc tgcaagggag ccaggcctgg aagctcggcc     960
aaaagagagc cgctcctttc tccccatctc ccaccccaag aaaggaggtg gtcctctggc    1020
aaccctgccc tccttcccca gcgctgggca cccagttagc actcaataaa tac           1073

<210> SEQ ID NO 4
<211> LENGTH: 261
<212> TYPE: PRT
<213> ORGANISM: Sus scrofa

<400> SEQUENCE: 4

Met His Ser Phe Gly Arg Cys Ile Phe Gly Gly Ala Ala Ala Ser Pro
1               5                   10                  15

Pro Val Thr Ile Arg Asn Leu Pro Gln Pro Ala Pro Ser Ser His
            20                  25                  30

Pro Leu Gly Gly Ile Arg Arg Glu Leu Thr Ala Gln Thr Pro Gly Leu
        35                  40                  45

Gln Arg Glu Lys Gly Arg Gly Arg Lys Gly Ile Glu Gly Arg Ser
    50                  55                  60

Leu Gly Trp Leu Gly Phe Phe Ser Leu Ser Ala Leu Ser Pro Gly Thr
65                  70                  75                  80

Leu Cys Pro Ala Met Gly Thr Phe Asn Leu Trp Thr Asp Tyr Leu Gly
                85                  90                  95

Leu Ala Arg Leu Val Gly Ala Leu Arg Gly Glu Glu Pro Glu Thr
            100                 105                 110
```

```
Arg Leu Asp Pro Gln Pro Ala Pro Val Pro Gly Pro Glu Gly Gln Arg
            115                 120                 125

Pro Ser Pro Glu Ser Ser Pro Ala Pro Glu Arg Leu Cys Ser Phe Cys
        130                 135                 140

Lys His Asn Gly Glu Ser Arg Ala Ile Tyr Gln Ser His Val Leu Lys
145                 150                 155                 160

Asp Glu Ala Gly Arg Val Leu Cys Pro Ile Leu Arg Asp Tyr Val Cys
                165                 170                 175

Pro Gln Cys Gly Ala Thr Arg Glu Arg Ala His Thr Arg Arg Phe Cys
            180                 185                 190

Pro Leu Thr Ser Gln Gly Tyr Thr Ser Val Tyr Ser Tyr Thr Thr Arg
        195                 200                 205

Asn Ser Ala Gly Lys Lys Leu Ala Arg Pro Asp Lys Ala Arg Thr Gln
    210                 215                 220

Asp Ser Gly His Arg Arg Gly Gly Gly Gly Gly Ala Ser Thr Gly
225                 230                 235                 240

Ser Lys Gly Ala Gly Lys Ser Ser Gly Thr Ser Pro Ser Pro Cys Cys
                245                 250                 255

Pro Ser Thr Ser Ala
            260

<210> SEQ ID NO 5
<211> LENGTH: 1906
<212> TYPE: DNA
<213> ORGANISM: Sus scrofa

<400> SEQUENCE: 5 cgcaggggc agggccgcgg cagcgaggcc gggggcggg gaggagcggg gcccgataaa      60
aggcagcgag gcgccccac cccgctgcag gccggcgggc aggctcggcg cgtccttcc    120 gtccggcccg cgccggcggc ggggaggcgg cgcgcgcggc ccgcagcccg cccatggagg   180
cttccccctg ggcccccgc tcgccccgcc gcggccgcgt cccccgccc atggcgctcg    240 tgcccagcgc ccgctacgtg agcgcccagg gcccggcgca cccgcaaccc ttcagctcgt   300
ggaacgacta cctgggactc gccacgctca tcaccaaggc ggtggacggc gagccgcgct   360
ttggctgcgc ccgcggcgag gacggcggcg gcggcggcgg ctccccaccc tcctcttcct   420
cctcgtcgtg ctgctcccc cacgcggggg ccgggcctgg ggcgctgggg ccgcgctgg    480 ggccacccga ctacgacgag gacgacgacg acgacagcga cgagccgggg tcccggggcc   540
gctacctggg gggcacgctg gagctgcgcg cgctggagct gtgcgcggac ccctcggagg   600
ccgggctgct ggaggagcgc ttcgccgagc tgagcccgtt cgcgggtcgc gccaccgctg   660
tgctgctggg ctgggcaccc gccactgccg ccaccgccga ggcggcaccg cgcgaggagc   720
gggccccggc gtgggcggcc gagccccggc tgcacgcagc ctttgggcg gccggcgccc    780 ggctgctcaa gcccgagctg caggtgtgtg tgttttgccg gaacaacaag gaggcggtgg   840
cgctctacac cacccacatc ttgaagggac ccgacgggga gtgctgtgc ccgtgctgc    900 gccgctacac gtgtcccctg tgcggcgcca gcggcgacaa cgcgcacacc atcaagtact   960
gcccgctctc caaagtgccg ccgccgcgca gcgtcaggga cggcctgccc ggcaagaagc  1020
tgcgctgagg gccggactc cggtctgcta ctgccacctg acgccaccag ggtcgccgcc  1080
tgcccaatgt ctagtttggc ctgcgcacca tctctctctc tcgctgctga ggagcgtgga  1140
gctcagctgt tggttgaact tgagatgtac tgatttttt tttttttttt tcaaagaac   1200 ccggcggtac tgagtccttt cctgtcgaag agcgcttaag actagaagct aaaatcttga  1260
```

```
tttgtttatc tctagtttgt gcacatccag acggtgaagg ctgggtgttc gttccactaa    1320
ctgaaatgtg gcaacttaga agtgtttatt tactctatac gtcaacctat tttagatgcg    1380
catcagtata tgaaattgtc tcaatctaat cttggatgtt taattttatg aatggaggca    1440
ctttactagg cctagaatat tttttttaaaa gcctctaaac tgaacttaac tggcgatttt    1500
atggaatgtc agcaaaatga cttttattgt ttgaaacaag taataatatt tctgttgtcc    1560
ttaatcagtt attctaattc caggtgaagc aaccctcacc tgcctggtag catcattaag    1620
tgaaggctta gtaaactttc cagtgttagt ttgggtgggt gttccccccg tggcttgttt    1680
ctgtcctagc tggaggtgta aagatgtaca atctgtggca ggtagaatac agctccttat    1740 cctttttatgt accacatctt ttattactga acgagcaact agcgtttccc atctttcaaa    1800
gtcgtgccag gttatataat attgtgtata cacttggaaa tggtgctgtt taaaagaatt    1860
tgtgtattta tacagtaaca gtatatgaat tcattaatct tgtctt                   1906
```

<210> SEQ ID NO 6
<211> LENGTH: 284
<212> TYPE: PRT
<213> ORGANISM: Sus scrofa

<400> SEQUENCE: 6

```
Met Glu Ala Phe Pro Trp Ala Pro Arg Ser Pro Arg Arg Gly Arg Val
1               5                   10                  15

Pro Pro Pro Met Ala Leu Val Pro Ser Ala Arg Tyr Val Ser Ala Gln
            20                  25                  30

Gly Pro Ala His Pro Gln Pro Phe Ser Ser Trp Asn Asp Tyr Leu Gly
        35                  40                  45

Leu Ala Thr Leu Ile Thr Lys Ala Val Asp Gly Glu Pro Arg Phe Gly
    50                  55                  60

Cys Ala Arg Gly Glu Asp Gly Gly Gly Gly Ser Pro Pro Ser
65                  70                  75                  80

Ser Ser Ser Ser Ser Cys Cys Ser Pro His Ala Gly Ala Gly Pro Gly
                85                  90                  95

Ala Leu Gly Pro Ala Leu Gly Pro Pro Asp Tyr Asp Glu Asp Asp Asp
            100                 105                 110

Asp Asp Ser Asp Glu Pro Gly Ser Arg Gly Arg Tyr Leu Gly Gly Thr
        115                 120                 125

Leu Glu Leu Arg Ala Leu Glu Leu Cys Ala Asp Pro Ser Glu Ala Gly
    130                 135                 140

Leu Leu Glu Glu Arg Phe Ala Glu Leu Ser Pro Phe Ala Gly Arg Ala
145                 150                 155                 160

Thr Ala Val Leu Leu Gly Trp Ala Pro Ala Thr Ala Ala Thr Ala Glu
                165                 170                 175

Ala Ala Pro Arg Glu Glu Arg Ala Pro Ala Trp Ala Ala Glu Pro Arg
            180                 185                 190

Leu His Ala Ala Phe Gly Ala Ala Gly Ala Arg Leu Leu Lys Pro Glu
        195                 200                 205

Leu Gln Val Cys Val Phe Cys Arg Asn Asn Lys Glu Ala Val Ala Leu
    210                 215                 220

Tyr Thr Thr His Ile Leu Lys Gly Pro Asp Gly Arg Val Leu Cys Pro
225                 230                 235                 240

Val Leu Arg Arg Tyr Thr Cys Pro Leu Cys Gly Ala Ser Gly Asp Asn
                245                 250                 255
```

Ala His Thr Ile Lys Tyr Cys Pro Leu Ser Lys Val Pro Pro Arg
            260                 265                 270

Ser Val Arg Asp Gly Leu Pro Gly Lys Lys Leu Arg
        275                 280

<210> SEQ ID NO 7
<211> LENGTH: 23
<212> TYPE: DNA
<213> ORGANISM: Sus scrofa

<400> SEQUENCE: 7
gaagacaccg agggcgtgg tgg                                            23

<210> SEQ ID NO 8
<211> LENGTH: 23
<212> TYPE: DNA
<213> ORGANISM: Sus scrofa

<400> SEQUENCE: 8
gaatcgtcga caagggccag agg                                           23

<210> SEQ ID NO 9
<211> LENGTH: 548
<212> TYPE: DNA
<213> ORGANISM: Bovine

<400> SEQUENCE: 9
tcagctgctc ctgtctgcgg gcccccagcc cacttctctc cagccaccca ccaccaacac    60
tcccccgggt gccatgcagc tgccacccct tgacatgtgg aaggactact caacctgag   120 ccaagtggtg ctggcactga tccagagtcg ggggcaaggg ttggagaccc aagggactgg   180
ggagccgaga cccgggcccc atgtggagca ggatcagggg cagggcggac gcggggctgg   240
cgggggcctg gccaccctgt gcaacttttg caaacacaat ggagagtctc gccacgtgta   300
ctcctcacac cagctgaaga ccccggaggg cgtggtggtg tgtcccattc tgcggcatta   360
tgtatgtccc ctgtgcgggg ccaccgggga ccaggcccac acactcaagt actgcccact   420
caacggagga cagcagtctc tctaccgccg cagtgggcgc aactcagccg ccgcaaggt   480 caagcgctga agaccgtcag gtacccaccc gctgcagccc aaccctccc tggttcagcc   540 ctcccaag                                                           548

<210> SEQ ID NO 10
<211> LENGTH: 138
<212> TYPE: PRT
<213> ORGANISM: Bovine

<400> SEQUENCE: 10

Met Gln Leu Pro Pro Phe Asp Met Trp Lys Asp Tyr Phe Asn Leu Ser
1               5                   10                  15

Gln Val Val Leu Ala Leu Ile Gln Ser Arg Gly Gln Gly Leu Glu Thr
            20                  25                  30

Gln Gly Thr Gly Glu Pro Arg Pro Gly Pro His Val Glu Gln Asp Gln
        35                  40                  45

Gly Gln Gly Gly Arg Gly Ala Gly Gly Leu Ala Thr Leu Cys Asn
    50                  55                  60

Phe Cys Lys His Asn Gly Glu Ser Arg His Val Tyr Ser Ser His Gln
65                  70                  75                  80

Leu Lys Thr Pro Glu Gly Val Val Val Cys Pro Ile Leu Arg His Tyr
                85                  90                  95

Val Cys Pro Leu Cys Gly Ala Thr Gly Asp Gln Ala His Thr Leu Lys
            100                 105                 110
Tyr Cys Pro Leu Asn Gly Gly Gln Gln Ser Leu Tyr Arg Arg Ser Gly
        115                 120                 125
Arg Asn Ser Ala Gly Arg Lys Val Lys Arg
    130                 135

<210> SEQ ID NO 11
<211> LENGTH: 1624
<212> TYPE: DNA
<213> ORGANISM: Bovine

<400> SEQUENCE: 11

| | | | | | | |
|---|---|---|---|---|---|---|
| gccgccgccg | cggccaccgc | cgaagcagca | ccgcgagagg | agcgggcccc | ggcgtgggcg | 60 |
| gccgagccca | agctgcacgc | cgcctccggg | gcggccgccg | cccggctgct | caagcccgag | 120 |
| ctgcaggtgt | gcgtgttttg | ccggaacaac | aaggaggcgg | tggcgctcta | caccacccac | 180 |
| atcctgaagg | acccgacgg | gcgggtgctg | tgccccgtgc | tgcgccggta | cacgtgtccc | 240 |
| ctgtgcggtg | ccagcggcga | caacgcgcac | accatcaagt | actgcccgct | ttccaaagtg | 300 |
| ccgccgccgc | ctgcagcccg | cccgccgccg | cgcagcgccc | gggacggcct | gcccggcaag | 360 |
| aagctgcgct | aagggcccgg | accccggtct | gctgctgcca | cctgatgcca | ctggggtagc | 420 |
| cgcccgccca | ctctcgtgtt | tggtctgcgc | accatctctt | cctcgctgcc | ggggagtgtg | 480 |
| gagctcgtct | tggttttcc | agaggaagcc | gacggtaccg | agtattttcc | taacgaagag | 540 |
| cagttgagac | tagacgttaa | aattttgatt | aatgtttcta | gtttgtgcac | atccagatgg | 600 |
| tgaaggctgg | gtattccact | aactgaaatg | tggcaactta | gaggcgctgt | ggtttattta | 660 |
| tacgtcgacc | tattttagat | gcgcatcagt | atgaaattgt | ctcagtctaa | tcttggatgt | 720 |
| ttaattttat | gaatggaggc | actttactag | gtctagaata | ttttttaaa | agcctctcaa | 780 |
| ctgaacttaa | aactggcgat | tttatggagt | gtcagcaaaa | tgactatttt | attgtctgaa | 840 |
| acaatatttc | tgttgtcctt | acccagttgt | aattccaggt | gaagccctgc | gtggtagcat | 900 |
| cattaagtga | agacttggta | tgctttacag | tgttagtttg | ggtgggtgtt | ccctccttgt | 960 |
| ggcttgtttt | tgtcctagct | ggagatgtat | aaaatgtaca | atttgtaggt | agcaggtaga | 1020 |
| atacagctca | tgtaccagat | cttttttatta | ctgaacgagc | aactactacc | gttttttcccc | 1080 |
| tttaaaaata | gtgccaagtt | ataatcatat | tgtgtataca | cttgaaaatg | gtgctgttta | 1140 |
| aaaaaattgt | gtatttatac | agtaacagta | tatgaattca | ttaaccttgc | ctttaactct | 1200 |
| acttggcttt | ttctttatgc | cccttcctat | tccagttctt | caaaaatatg | tgatacttaa | 1260 |
| gatcaaacgg | gtgcaataac | tcattcactc | tgaattgctc | catttcaggg | tctctaaata | 1320 |
| gtggaaatct | cattccagct | gttgcctctc | agactaaatg | taagatggaa | tcctttgagc | 1380 |
| tctggaaggt | taatgaaaca | actggtgttc | aggaaggttc | cactctggac | tgtgtcagct | 1440 |
| ttaaaccatc | acagaagtcc | tcaaaccagt | ataagtacca | attaaaggaa | ctgactgggt | 1500 |
| gtagggggg | taacacaagg | aacacagcct | ccatctattg | tgttcccatt | ctcattagaa | 1560 |
| gacaacccctt | ctggaatccc | accagttatt | ttcatcggtg | agattaaatc | taatcttggg | 1620 |
| caaa | | | | | | 1624 |

<210> SEQ ID NO 12
<211> LENGTH: 123
<212> TYPE: PRT
<213> ORGANISM: Bovine

<400> SEQUENCE: 12

| | | | | | | | | | | | | | | |
|---|---|---|---|---|---|---|---|---|---|---|---|---|---|---|
| Ala | Ala | Ala | Ala | Ala | Thr | Ala | Glu | Ala | Ala | Pro | Arg | Glu | Glu | Arg | Ala |
| 1 | | | | 5 | | | | | 10 | | | | | 15 | |
| Pro | Ala | Trp | Ala | Ala | Glu | Pro | Lys | Leu | His | Ala | Ala | Ser | Gly | Ala | Ala |
| | | | 20 | | | | | 25 | | | | | 30 | | |
| Ala | Ala | Arg | Leu | Leu | Lys | Pro | Glu | Leu | Gln | Val | Cys | Val | Phe | Cys | Arg |
| | | 35 | | | | | 40 | | | | | 45 | | | |
| Asn | Asn | Lys | Glu | Ala | Val | Ala | Leu | Tyr | Thr | Thr | His | Ile | Leu | Lys | Gly |
| | 50 | | | | | 55 | | | | | 60 | | | | |
| Pro | Asp | Gly | Arg | Val | Leu | Cys | Pro | Val | Leu | Arg | Arg | Tyr | Thr | Cys | Pro |
| 65 | | | | | 70 | | | | | 75 | | | | | 80 |
| Leu | Cys | Gly | Ala | Ser | Gly | Asp | Asn | Ala | His | Thr | Ile | Lys | Tyr | Cys | Pro |
| | | | | 85 | | | | | 90 | | | | | 95 | |
| Leu | Ser | Lys | Val | Pro | Pro | Pro | Ala | Ala | Arg | Pro | Pro | Arg | Ser |
| | | | 100 | | | | | 105 | | | | | 110 | |
| Ala | Arg | Asp | Gly | Leu | Pro | Gly | Lys | Lys | Leu | Arg |
| | | 115 | | | | | 120 | | | |

<210> SEQ ID NO 13
<211> LENGTH: 2056
<212> TYPE: DNA
<213> ORGANISM: Bovine

<400> SEQUENCE: 13

```
cgctacgtga gcacccaggg cccggcgcac ccgcagccct tcagctcgtg gaacgactat      60
ctgggactcg ccacgctcat caccaaggcg gtggacggcg agccgcgctt cggctgcgcc     120
cgcggcgggg acggcggcgg ggacggctcc ccgccttctt cttcctcctc gtcgtgctgc     180
tccccccacg tggggccgg gcctggggcg ctggggcccg cgctggggcc gcccgactac      240
gacgaggacg acgacgacga cgacagcgac gatccggggt cccggagccg ctacctgggg     300
ggcgcgctgg agctgcgcgc gctggagctg tgcgcggacc ctgccgaggc cgggctgctg     360
gaggagcgtt cgctgagct gagcccgttc gctggtcgcg ccgctgccgt gcttctgggc      420
tgcgcacccg ccgccgccgc gcggccacc gccgaagcag caccgcgaga ggagcgggcc      480
ccggcgtggg cggccgagcc caagctgcac gccgcctccg gggcggccgc cgcccggctg     540
ctcaagcccg agctgcaggt gtgcgtgttt tgccggaaca acaaggaggc ggtggcgctc     600
tacaccaccc acatcctgaa gggacccgac gggcgggtgc tgtgccccgt gctgcgccgg     660
tacacgtgtc ccctgtgcgg tgccagcggc gacaacgcgc acaccatcaa gtactgcccg     720
ctttccaaag tgccgccgcc gcctgcagcc cgcccgccgc cgcgcagcgc ccgggacggc     780
ctgcccggca agaagctgcg ctaagggccc ggacccggt ctgctgctgc acctgatgc       840
cactggggta gccgcccgcc cactctcgtg tttggtctgc gcaccatctc ttcctcgctg     900
ccggggagtg tggagctcgt cttggttttt ccagaggaag ccgacggtac cgagtatttt     960
cctaacgaag agcagttgag actagacgtt aaaattttga ttaatgtttc tagtttgtgc    1020
acatccagat ggtgaaggct gggtattcca ctaactgaaa tgtggcaact tagaggcgct    1080
gtggtttatt tatacgtcga cctatttag atgcgcatca gtatgaaatt gtctcagtct     1140
aatcttggat gtttaatttt atgaatggag gcacttact aggtctagaa tattttttta     1200
aaagcctctc aactgaactt aaaactggcg atttttatgga gtgtcagcaa atgactatt    1260
ttattgtctg aaacaatatt tctgttgtcc ttacccagtt gtaattccag gtgaagccct    1320
```

```
gcgtggtagc atcattaagt gaagacttgg tatgctttac agtgttagtt tgggtgggtg    1380
ttccctcctt gtggcttgtt tttgtcctag ctggagatgt ataaaatgta caatttgtag    1440
gtagcaggta gaatacagct catgtaccag atctttttat tactgaacga gcaactacta    1500 ccgttttttcc cctttaaaaa tagtgccaag ttataatcat attgtgtata cacttgaaaa    1560
tggtgctgtt taaaaaaatt gtgtatttat acagtaacag tatatgaatt cattaacctt    1620
gcctttaact ctacttggct ttttctttat gccccttcct attccagttc ttcaaaaata    1680
tgtgatactt aagatcaaac gggtgcaata actcattcac tctgaattgc tccatttcag    1740
ggtctctaaa tagtggaaat ctcattccag ctgttgcctc tcagactaaa tgtaagatgg    1800
aatcctttga gctctggaag gttaatgaaa caactggtgt tcaggaaggt tccactctgg    1860
actgtgtcag ctttaaacca tcacagaagt cctcaaacca gtataagtac caattaaagg    1920
aactgactgg gtgtaggggg ggtaacacaa ggaacacagc ctccatctat tgtgttccca    1980
ttctcattag aagacaaccc ttctggaatc ccaccagtta ttttcatcgg tgagattaaa    2040
tctaatcttg ggcaaa                                                    2056
```

<210> SEQ ID NO 14
<211> LENGTH: 267
<212> TYPE: PRT
<213> ORGANISM: Bovine

<400> SEQUENCE: 14

```
Arg Tyr Val Ser Thr Gln Gly Pro Ala His Pro Gln Pro Phe Ser Ser
1               5                   10                  15

Trp Asn Asp Tyr Leu Gly Leu Ala Thr Leu Ile Thr Lys Ala Val Asp
            20                  25                  30

Gly Glu Pro Arg Phe Gly Cys Ala Arg Gly Gly Asp Gly Gly Gly Asp
        35                  40                  45

Gly Ser Pro Pro Ser Ser Ser Ser Cys Cys Ser Pro His Val
    50                  55                  60

Gly Ala Gly Pro Gly Ala Leu Gly Pro Ala Leu Gly Pro Pro Asp Tyr
65                  70                  75                  80

Asp Glu Asp Asp Asp Asp Asp Ser Asp Asp Pro Gly Ser Arg Ser
            85                  90                  95

Arg Tyr Leu Gly Gly Ala Leu Glu Leu Arg Ala Leu Glu Leu Cys Ala
            100                 105                 110

Asp Pro Ala Glu Ala Gly Leu Leu Glu Glu Arg Phe Ala Glu Leu Ser
        115                 120                 125

Pro Phe Ala Gly Arg Ala Ala Ala Val Leu Leu Gly Cys Ala Pro Ala
    130                 135                 140

Ala Ala Ala Ala Thr Ala Glu Ala Pro Arg Glu Glu Arg Ala
145                 150                 155                 160

Pro Ala Trp Ala Ala Glu Pro Lys Leu His Ala Ala Ser Gly Ala Ala
            165                 170                 175

Ala Ala Arg Leu Leu Lys Pro Glu Leu Gln Val Cys Val Phe Cys Arg
            180                 185                 190

Asn Asn Lys Glu Ala Val Ala Leu Tyr Thr Thr His Ile Leu Lys Gly
        195                 200                 205

Pro Asp Gly Arg Val Leu Cys Pro Val Leu Arg Arg Tyr Thr Cys Pro
    210                 215                 220

Leu Cys Gly Ala Ser Gly Asp Asn Ala His Thr Ile Lys Tyr Cys Pro
225                 230                 235                 240
```

Leu Ser Lys Val Pro Pro Pro Ala Ala Arg Pro Pro Pro Arg Ser
            245                 250                 255

Ala Arg Asp Gly Leu Pro Gly Lys Lys Leu Arg
        260                 265

<210> SEQ ID NO 15
<211> LENGTH: 482
<212> TYPE: DNA
<213> ORGANISM: Artificial Sequence
<220> FEATURE:
<223> OTHER INFORMATION: Synthetic polynucleotide

<400> SEQUENCE: 15

| | | |
|---|---|---:|
| agttaactaa gctttgtaca aaaaagcagg ctttaaagga accaattcag tcgactggat | | 60 |
| ccggtaccaa ggtcgggcag gaagagggcc tatttcccat gattccttca tatttgcata | | 120 |
| tacgatacaa ggctgttaga gagataatta gaattaattt gactgtaaac acaaagatat | | 180 |
| tagtacaaaa tacgtgacgt agaaagtaat aatttcttgg gtagtttgca gttttaaaat | | 240 |
| tatgttttaa aatggactat catatgctta ccgtaacttg aaagtatttc gatttcttgg | | 300 |
| ctttatatat cttgtggaaa ggacgaaaca ccgaatcgtc gacaagggcc aggttttaga | | 360 |
| gctagaaata gcaagttaaa ataaggctag tccgttatca acttgaaaaa gtggcaccga | | 420 |
| gtcggtgctt ttttctaga cccagctttc ttgtacaaag ttggcattac tcgagatcca | | 480 |
| ct | | 482 |

<210> SEQ ID NO 16
<211> LENGTH: 482
<212> TYPE: DNA
<213> ORGANISM: Artificial Sequence
<220> FEATURE:
<223> OTHER INFORMATION: Synthetic polynucleotide

<400> SEQUENCE: 16

| | | |
|---|---|---:|
| agttaactaa gctttgtaca aaaaagcagg ctttaaagga accaattcag tcgactggat | | 60 |
| ccggtaccaa ggtcgggcag gaagagggcc tatttcccat gattccttca tatttgcata | | 120 |
| tacgatacaa ggctgttaga gagataatta gaattaattt gactgtaaac acaaagatat | | 180 |
| tagtacaaaa tacgtgacgt agaaagtaat aatttcttgg gtagtttgca gttttaaaat | | 240 |
| tatgttttaa aatggactat catatgctta ccgtaacttg aaagtatttc gatttcttgg | | 300 |
| ctttatatat cttgtggaaa ggacgaaaca ccgaatcgtc gacaagggcc aggttttaga | | 360 |
| gctagaaata gcaagttaaa ataaggctag tccgttatca acttgaaaaa gtggcaccga | | 420 |
| gtcggtgctt ttttctaga cccagctttc ttgtacaaag ttggcattac tcgagatcca | | 480 |
| ct | | 482 |

<210> SEQ ID NO 17
<211> LENGTH: 482
<212> TYPE: DNA
<213> ORGANISM: Artificial Sequence
<220> FEATURE:
<223> OTHER INFORMATION: Synthetic polynucleotide

<400> SEQUENCE: 17

| | | |
|---|---|---:|
| agttaactaa gctttgtaca aaaaagcagg ctttaaagga accaattcag tcgactggat | | 60 |
| ccggtaccaa ggtcgggcag gaagagggcc tatttcccat gattccttca tatttgcata | | 120 |
| tacgatacaa ggctgttaga gagataatta gaattaattt gactgtaaac acaaagatat | | 180 |
| tagtacaaaa tacgtgacgt agaaagtaat aatttcttgg gtagtttgca gttttaaaat | | 240 |

-continued

```
tatgttttaa aatggactat catatgctta ccgtaacttg aaagtatttc gatttcttgg    300
ctttatatat cttgtggaaa ggacgaaaca ccgtggccct tgtcgacgat tcgttttaga    360
gctagaaata gcaagttaaa ataaggctag tccgttatca acttgaaaaa gtggcaccga    420
gtcggtgctt ttttctaga cccagctttc ttgtacaaag ttggcattac tcgagatcca     480
ct                                                                    482
```

<210> SEQ ID NO 18
<211> LENGTH: 318
<212> TYPE: DNA
<213> ORGANISM: Artificial Sequence
<220> FEATURE:
<223> OTHER INFORMATION: Synthetic polynucleotide

<400> SEQUENCE: 18

```
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacacc                                                  318
```

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19

```
gtggcccttg tcgacgattc                                                 20
```

<210> SEQ ID NO 20
<211> LENGTH: 76
<212> TYPE: DNA
<213> ORGANISM: Artificial Sequence
<220> FEATURE:
<223> OTHER INFORMATION: Synthetic polynucleotide

<400> SEQUENCE: 20

```
gttttagagc tagaaatagc aagttaaaat aaggctagtc cgttatcaac ttgaaaaagt    60
ggcaccgagt cggtgc                                                    76
```

<210> SEQ ID NO 21
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(10)
<223> OTHER INFORMATION: n is a, c, g, or t

<400> SEQUENCE: 21

```
tttttttnnn                                                            10
```

<210> SEQ ID NO 22
<211> LENGTH: 360
<212> TYPE: DNA

```
<213> ORGANISM: Artificial Sequence
<220> FEATURE:
<223> OTHER INFORMATION: Synthetic polynucleotide

<400> SEQUENCE: 22
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacaccg gtcttcgag aagacctgtt tagagctag aaatagcaag ttaaataag        300 gctagtccgt tatcaacttg aaaaagtggc accgagtcgg tgcttttttg ttttagagct     360

<210> SEQ ID NO 23
<211> LENGTH: 240
<212> TYPE: DNA
<213> ORGANISM: Artificial Sequence
<220> FEATURE:
<223> OTHER INFORMATION: Synthetic oligonucleotide

<400> SEQUENCE: 23
tttcccatga ttccttcata tttgcatata cgatacaagg ctgttagaga gataattgga      60
attaatttga ctgtaaacac aaagatatta gtacaaaata cgtgacgtag aaagtaataa     120
tttcttgggt agtttgcagt tttaaaatta tgttttaaaa tggactatca tatgcttacc     180
gtaacttgaa agtatttcga tttcttggct ttatatatct tgtggaaagg acgaaacacc     240

<210> SEQ ID NO 24
<211> LENGTH: 76
<212> TYPE: DNA
<213> ORGANISM: Artificial Sequence
<220> FEATURE:
<223> OTHER INFORMATION: Synthetic oligonucleotide

<400> SEQUENCE: 24
gttttagagc tagaaatagc aagttaaaat aaggctagtc cgttatcaac ttgaaaaagt      60
ggcaccgagt cggtgc                                                      76

<210> SEQ ID NO 25
<211> LENGTH: 10
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (7)..(10)
<223> OTHER INFORMATION: n is a, c, g, or t

<400> SEQUENCE: 25 tttttnnnn                                                              10

<210> SEQ ID NO 26
<211> LENGTH: 61
<212> TYPE: DNA
<213> ORGANISM: Sus scrofa

<400> SEQUENCE: 26
cccggtgccc ggggcctctg gcccttgtcg acgattctgg atcagtccca acaccacctg      60
g                                                                      61
```

```
<210> SEQ ID NO 27
<211> LENGTH: 61
<212> TYPE: DNA
<213> ORGANISM: Sus scrofa

<400> SEQUENCE: 27
cccggtgccc ggggcccttg tcgacgatca gcccttctgg atcagtccca acaccacctg    60
g                                                                    61

<210> SEQ ID NO 28
<211> LENGTH: 356
<212> TYPE: DNA
<213> ORGANISM: Sus scrofa

<400> SEQUENCE: 28
tcagcgcttg accttgcggc cggctgaatt gcgcccactg cggcgataga gagactgctg    60
gccgccgttg agcgggcagt acttgagtgt gtgagcctgg tcaccggtgg ccccgcacag   120
gggacacaca tagtgtcgta ggatgggaca caccaccacg ccctccggtg tcttcagctg   180
gtgcgaggag tacacgtggc gagattcccc attgtgtttg caaaagttgc acagggtggc   240 cagcccccccg ctggccccc gctctcccgg gccctggtcc tgctccagtg ggggctcagg   300
tcttggctcc tcaggttgaa gtagtccttc cacatgtcaa agggtggcag ctgcat       356

<210> SEQ ID NO 29
<211> LENGTH: 56
<212> TYPE: DNA
<213> ORGANISM: Sus scrofa

<400> SEQUENCE: 29
ttggctcccc ggtgcccggg gcctctggcc cttgtcgacg attctggatc agtccc        56

<210> SEQ ID NO 30
<211> LENGTH: 56
<212> TYPE: DNA
<213> ORGANISM: Sus scrofa

<400> SEQUENCE: 30
ttggctcccc ggtgcccggg gcctctggcc cttgtcgacg attctggatc agtccc        56

<210> SEQ ID NO 31
<211> LENGTH: 49
<212> TYPE: DNA
<213> ORGANISM: Sus scrofa

<400> SEQUENCE: 31
ttggctcccc ggtgcccggg gcctctgtcg acgattctgg atcagtccc                49

<210> SEQ ID NO 32
<211> LENGTH: 49
<212> TYPE: DNA
<213> ORGANISM: Sus scrofa

<400> SEQUENCE: 32
ttggctcccc ggtgcccggg gcctctgtcg acgattctgg atcagtccc                49

<210> SEQ ID NO 33
<211> LENGTH: 55
<212> TYPE: DNA
<213> ORGANISM: Sus scrofa

<400> SEQUENCE: 33
```

```
ttggctcccg gtgcccgggg cctctggccc ttgtcgacga ttctggatca gtccc        55
```

<210> SEQ ID NO 34
<211> LENGTH: 54
<212> TYPE: DNA
<213> ORGANISM: Sus scrofa

<400> SEQUENCE: 34

```
ttggctcccc ggtgcccggg gcctctgccc ttgtccacaa ttctggatca tccc         54
```

<210> SEQ ID NO 35
<211> LENGTH: 49
<212> TYPE: DNA
<213> ORGANISM: Sus scrofa

<400> SEQUENCE: 35

```
ttggctcccc ggtgcccggg gcctctgtcg acgattctgg atcagtccc               49
```

<210> SEQ ID NO 36
<211> LENGTH: 49
<212> TYPE: DNA
<213> ORGANISM: Sus scrofa

<400> SEQUENCE: 36

```
ttggctcccc ggtgcccggt gcccttgtcg acgattctgg atcagtccc               49
```

<210> SEQ ID NO 37
<211> LENGTH: 49
<212> TYPE: DNA
<213> ORGANISM: Sus scrofa

<400> SEQUENCE: 37

```
ttggctcccc ggtgcccggg gcccttgtcg acgattctgg atcagtccc               49
```

<210> SEQ ID NO 38
<211> LENGTH: 54
<212> TYPE: DNA
<213> ORGANISM: Sus scrofa

<400> SEQUENCE: 38

```
ttggctcccc ggtgcccggg gcctctgcct tgtcgacgat tctggatcag tccc         54
```

<210> SEQ ID NO 39
<211> LENGTH: 49
<212> TYPE: DNA
<213> ORGANISM: Sus scrofa

<400> SEQUENCE: 39

```
ttggctcccc ggtgcccggg gcctctgtcg acgattctgg atcagtccc               49
```

<210> SEQ ID NO 40
<211> LENGTH: 50
<212> TYPE: DNA
<213> ORGANISM: Sus scrofa

<400> SEQUENCE: 40

```
ttggctcccc ggtgcccggg gccccttgtc gacgattctg gatcagtccc              50
```

<210> SEQ ID NO 41
<211> LENGTH: 55
<212> TYPE: DNA
<213> ORGANISM: Sus scrofa

<400> SEQUENCE: 41

```
ttggctcccc ggtgcccggg gcctctgccc ttgtcgtcaa ttctggatca gtccc         55

<210> SEQ ID NO 42
<211> LENGTH: 49
<212> TYPE: DNA
<213> ORGANISM: Sus scrofa

<400> SEQUENCE: 42
ttggctcccc ggtgcccggg gcctctgtcg acaattctgg atcagtccc                49

<210> SEQ ID NO 43
<211> LENGTH: 9289
<212> TYPE: DNA
<213> ORGANISM: Artificial Sequence
<220> FEATURE:
<223> OTHER INFORMATION: Synthetic polynucleotide

<400> SEQUENCE: 43
gagggcctat ttcccatgat tccttcatat ttgcatatac gatacaaggc tgttagagag      60
ataattggaa ttaatttgac tgtaaacaca agatattag tacaaaatac gtgacgtaga     120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg ggtcttcgag aagacctgtt ttagagctag aaatagcaag ttaaaataag    300
gctagtccgt tatcaacttg aaaaagtggc accgagtcgg tgctttttg ttttagagct     360 agaaatagca agttaaaata aggctagtcc gttttagcg cgtgcgccaa ttctgcagac     420
aaatggctct agaggtaccc gttacataac ttacggtaaa tggcccgcct ggctgaccgc    480
ccaacgaccc ccgcccattg acgtcaatag taacgccaat agggactttc cattgacgtc    540
aatgggtgga gtatttacgg taaactgccc acttggcagt acatcaagtg tatcatatgc    600
caagtacgcc ccctattgac gtcaatgacg gtaaatggcc cgcctggcat tgtgcccagt    660
acatgacctt atgggacttt cctacttggc agtacatcta cgtattagtc atcgctatta    720
ccatggtcga ggtgagcccc acgttctgct tcactctccc catctccccc ccctccccac    780
ccccaatttt gtatttattt attttttaat tattttgtgc agcgatgggg gcgggggggg    840
ggggggggcg cgcgccaggc ggggcgggc ggggcgaggg gcgggcggg gcgaggcgga     900 gaggtgcggc ggcagccaat cagagcggcg cgctccgaaa gtttccttt atggcgaggc     960 ggcggcggcg gcggccctat aaaaagcgaa gcgcgcggcg gcgggagtc gctgcgacgc    1020 tgccttcgcc ccgtgccccg ctccgccgcc gcctcgcgcc gcccgccccg gctctgactg    1080
accgcgttac tcccacaggt gagcgggcgg gacggccctt ctcctccggg ctgtaattag    1140
ctgagcaaga ggtaagggtt taagggatgg ttggttggtg gggtattaat gtttaattac    1200
ctggagcacc tgcctgaaat caatgacgat aagatggccc caaagaagaa gcggaaggtc    1260
ggtatccacg gagtcccagc agccgacaag aagtacagca tcggcctgga catcggcacc    1320
aactctgtgg gctgggccgt gatcaccgac gagtacaagg tgcccagcaa gaaattcaag    1380
gtgctgggca acaccgaccg gcacagcatc aagaagaacc tgatcggagc cctgctgttc    1440
gacagcggca aaacagccga ggccaccgg ctgaagagaa ccgccagaag aagatacacc     1500
agacggaaga accggatctg ctatctgcaa gagatcttca gcaacgagat ggccaaggtg    1560
gacgacagct tcttccacag actggaagag tccttcctgg tggaagagga taagaagcac    1620
gagcggcacc ccatcttcgg caacatcgtg gacgaggtgg cctaccacga gaagtacccc    1680
```

```
accatctacc acctgagaaa gaaactggtg gacagcaccg acaaggccga cctgcggctg    1740
atctatctgg ccctggccca catgatcaag ttccggggcc acttcctgat cgagggcgac    1800
ctgaaccccg acaacagcga cgtggacaag ctgttcatcc agctggtgca gacctacaac    1860
cagctgttcg aggaaaaccc catcaacgcc agcggcgtgg acgccaaggc catcctgtct    1920
gccagactga gcaagagcag acggctggaa aatctgatcg cccagctgcc cggcgagaag    1980
aagaatggcc tgttcggaaa cctgattgcc ctgagcctgg gcctgacccc caacttcaag    2040
agcaacttcg acctggccga ggatgccaaa ctgcagctga gcaaggacac ctacgacgac    2100
gacctggaca acctgctggc ccagatcggc gaccagtacg ccgacctgtt tctggccgcc    2160
aagaacctgt ccgacgccat cctgctgagc gacatcctga gagtgaacac cgagatcacc    2220
aaggcccccc tgagcgcctc tatgatcaag agatacgacg agcaccacca ggacctgacc    2280
ctgctgaaag ctctcgtgcg gcagcagctg cctgagaagt acaaagagat tttcttcgac    2340
cagagcaaga acggctacgc cggctacatt gacggcggag ccagccagga agagttctac    2400
aagttcatca agcccatcct ggaaaagatg gacggcaccg aggaactgct cgtgaagctg    2460
aacagagagg acctgctgcg gaagcagcgg accttcgaca acggcagcat ccccaccag    2520
atccacctgg gagagctgca cgccattctg cggcggcagg aagatttta cccattcctg    2580
aaggacaacc gggaaaagat cgagaagatc ctgaccttcc gcatccccta ctacgtgggc    2640
cctctggcca ggggaaacag cagattcgcc tggatgacca aaagagcga ggaaaccatc    2700
accccctgga acttcgagga agtggtggac aagggcgctt ccgcccagag cttcatcgag    2760
cggatgacca acttcgataa gaacctgccc aacgagaagg tgctgcccaa gcacagcctg    2820
ctgtacgagt acttcaccgt gtataacgag ctgaccaaag tgaaatacgt gaccgaggga    2880
atgagaaagc ccgccttcct gagcggcgag cagaaaaagg ccatcgtgga cctgctgttc    2940
aagaccaacc ggaaagtgac cgtgaagcag ctgaagagg actacttcaa gaaaatcgag    3000
tgcttcgact ccgtggaaat ctccggcgtg gaagatcggt tcaacgcctc cctgggcaca    3060
taccacgatc tgctgaaaat tatcaaggac aaggacttcc tggacaatga ggaaaacgag    3120
gacattctgg aagatatcgt gctgaccctg acactgtttg aggacagaga gatgatcgag    3180
gaacggctga aaacctatgc ccacctgttc gacgacaaag tgatgaagca gctgaagcgg    3240
cggagataca caccggctgggg caggctgagc cggaagctga tcaacggcat ccgggacaag    3300
cagtccggca agacaatcct ggatttcctg aagtccgacg gcttcgccaa cagaaacttc    3360
atgcagctga tccacgacga cagcctgacc tttaaagagg acatccagaa agcccaggtg    3420
tccggccagg gcgatagcct gcacgagcac attgccaatc tggccggcag ccccgccatt    3480
aagaagggca tcctgcagac agtgaaggtg gtggacgagc tcgtgaaagt gatgggccgg    3540
cacaagcccg agaacatcgt gatcgaaatg gccagagaga accagaccac ccagaaggga    3600
cagaagaaca gccgcgagag aatgaagcgg atcgaagagg gcatcaaaga gctgggcagc    3660
cagatcctga aagaacaccc cgtggaaaac acccagctgc agaacgagaa gctgtacctg    3720
tactacctgc agaatgggcg ggatatgtac gtggaccagg aactggacat caaccggctg    3780
tccgactacg atgtggacca tatcgtgcct cagagctttc tgaaggacga ctccatcgac    3840
aacaaggtgc tgaccagaag cgacaagaac cggggcaaga gcgacaacgt gccctccgaa    3900
gaggtcgtga agaagatgaa gaactactgg cggcagctgc tgaacgccaa gctgattacc    3960
cagagaaagt tcgacaatct gaccaaggcc gagagaggcg gcctgagcga actggataag    4020
gccggcttca tcaagagaca gctggtggaa acccggcaga tcacaaagca cgtggcacag    4080
```

```
atcctggact cccggatgaa cactaagtac gacgagaatg acaagctgat ccgggaagtg    4140
aaagtgatca ccctgaagtc caagctggtg tccgatttcc ggaaggattt ccagttttac    4200
aaagtgcgcg agatcaacaa ctaccaccac gcccacgacg cctacctgaa cgccgtcgtg    4260
ggaaccgccc tgatcaaaaa gtaccctaag ctggaaagcg agttcgtgta cggcgactac    4320
aaggtgtacg acgtgcggaa gatgatcgcc aagagcgagc aggaaatcgg caaggctacc    4380
gccaagtact tcttctacag caacatcatg aacttttttca agaccgagat taccctggcc    4440
aacggcgaga tccggaagcg gcctctgatc gagacaaacg gcgaaaccgg ggagatcgtg    4500
tgggataagg gccgggattt tgccaccgtg cggaaagtgc tgagcatgcc ccaagtgaat    4560
atcgtgaaaa agaccgaggt gcagacaggc ggcttcagca agagtctat cctgcccaag    4620
aggaacagcg ataagctgat cgccagaaag aaggactggg accctaagaa gtacggcggc    4680
ttcgacagcc ccaccgtggc ctattctgtg ctggtggtgg ccaaagtgga aaagggcaag    4740
tccaagaaac tgaagagtgt gaaagagctg ctggggatca ccatcatgga agaagcagc    4800
ttcgagaaga atcccatcga cttttctggaa gccaagggct acaaagaagt gaaaaaggac    4860
ctgatcatca agctgcctaa gtactccctg ttcgagctgg aactttttttt caggttggac    4920
cggtgccacc atggactata aggaccacga cggagactac aaggatcatg atattgatta    4980
caaagacgaa cggccggaag agaatgctgg cctctgccgg cgaactgcag aagggaaacg    5040
aactggccct gccctccaaa tatgtgaact tcctgtacct ggccagccac tatgagaagc    5100
tgaagggctc ccccgaggat aatgagcaga acagctgtt tgtggaacag cacaagcact    5160
acctggacga gatcatcgag cagatcagcg agttctccaa gagagtgatc ctggccgacg    5220
ctaatctgga caaagtgctg tccgcctaca acaagcaccg ggataagccc atcagagagc    5280
aggccgagaa tatcatccac ctgtttaccc tgaccaatct gggagcccct gccgccttca    5340
agtactttga caccaccatc gaccggaaga ggtacaccag caccaaagag gtgctggacg    5400
ccaccctgat ccaccagagc atcaccggcc tgtacgagac acggatcgac ctgtctcagc    5460
tgggaggcga caaaaggccg gcggccacga aaaaggccgg ccaggcaaaa aagaaaaagg    5520
aattcggcag tggagagggc agaggaagtc tgctaacatg cggtgacgtc gaggagaatc    5580
ctggcccagt gagcaagggc gaggagctgt tcaccgggt ggtgcccatc ctggtcgagc    5640
tggacggcga cgtaaacggc cacaagttca gcgtgtccgg cgagggcgag ggcgatgcca    5700
cctacggcaa gctgaccctg aagttcatct gcaccaccgg caagctgccc gtgccctggc    5760
ccaccctcgt gaccaccctg acctacggcg tgcagtgctt cagccgctac cccgaccaca    5820
tgaagcagca cgacttcttc aagtccgcca tgcccgaagg ctacgtccag gagcgcacca    5880
tcttcttcaa ggacgacggc aactacaaga cccgcgccga ggtgaagttc gagggcgaca    5940
ccctggtgaa ccgcatcgag ctgaagggca tcgacttcaa ggaggacggc aacatcctgg    6000
ggcacaagct ggagtacaac tacaacagcc acaacgtcta tatcatggcc gacaagcaga    6060
agaacggcat caaggtgaac ttcaagatcc gccacaacat cgaggacggc agcgtgcagc    6120
tcgccgacca ctaccagcag aacacccca tcggcgacgg ccccgtgctg ctgcccgaca    6180
accactacct gagcacccag tccgccctga gcaaagaccc caacgagaag cgcgatcaca    6240
tggtcctgct ggagttcgtg accgccgccg ggatcactct cggcatggac gagctgtaca    6300
aggaattcta actagagctc gctgatcagc ctcgactgtg ccttctagtt gccagccatc    6360
tgttgtttgc ccctcccccg tgccttcctt gaccctggaa ggtgccactc ccactgtcct    6420
```

```
ttcctaataa aatgaggaaa ttgcatcgca ttgtctgagt aggtgtcatt ctattctggg    6480
gggtggggtg gggcaggaca gcaaggggga ggattgggaa gagaatagca ggcatgctgg    6540
ggagcggccg caggaacccc tagtgatgga gttggccact ccctctctgc gcgctcgctc    6600
gctcactgag gccgggcgac caaaggtcgc ccgacgcccg ggctttgccc gggcggcctc    6660
agtgagcgag cgagcgcgca gctgcctgca ggggcgcctg atgcggtatt ttctccttac    6720
gcatctgtgc ggtatttcac accgcatacg tcaaagcaac catagtacgc gccctgtagc    6780
ggcgcattaa gcgcggcggg tgtggtggtt acgcgcagcg tgaccgctac acttgccagc    6840
gccctagcgc ccgctccttt cgctttcttc ccttcctttc tcgccacgtt cgccggcttt    6900
ccccgtcaag ctctaaatcg gggctccct ttagggttcc gatttagtgc tttacggcac    6960
ctcgacccca aaaaacttga tttgggtgat ggttcacgta gtgggccatc gccctgatag    7020 acggttttc gccctttgac gttggagtcc acgttcttta atagtggact cttgttccaa    7080
actggaacaa cactcaaccc tatctcgggc tattctttg atttataagg gattttgccg    7140
atttcggcct attggttaaa aaatgagctg atttaacaaa aatttaacgc gaattttaac    7200
aaaatattaa cgtttacaat tttatggtgc actctcagta caatctgctc tgatgccgca    7260
tagttaagcc agccccgaca cccgccaaca cccgctgacg cgccctgacg gcttgtctg    7320 ctcccggcat ccgcttacag acaagctgtg accgtctccg ggagctgcat gtgtcagagg    7380
ttttcaccgt catcaccgaa acgcgcgaga cgaaagggcc tcgtgatacg cctatttta    7440 taggttaatg tcatgataat aatggtttct tagacgtcag gtggcacttt tcggggaaat    7500
gtgcgcggaa cccctatttg tttatttttc taaatacatt caaatatgta tccgctcatg    7560
agacaataac cctgataaat gcttcaataa tattgaaaaa ggaagagtat gagtattcaa    7620
catttccgtg tcgcccttat ccctttttt gcggcatttt gccttcctgt ttttgctcac    7680
ccagaaacgc tggtgaaagt aaaagatgct gaagatcagt tgggtgcacg agtgggttac    7740
atcgaactgg atctcaacag cggtaagatc cttgagagtt ttcgccccga agaacgtttt    7800
ccaatgatga gcacttttaa agttctgcta tgtggcgcgg tattatcccg tattgacgcc    7860
gggcaagagc aactcggtcg ccgcatacac tattctcaga atgacttggt tgagtactca    7920
ccagtcacag aaaagcatct tacggatggc atgacagtaa gagaattatg cagtgctgcc    7980
ataaccatga gtgataacac tgcggccaac ttacttctga caacgatcgg aggaccgaag    8040
gagctaaccg cttttttgca caacatgggg gatcatgtaa ctcgccttga tcgttgggaa    8100
ccggagctga atgaagccat accaaacgac gagcgtgaca ccacgatgcc tgtagcaatg    8160
gcaacaacgt tgcgcaaact attaactggc gaactactta ctctagcttc ccggcaacaa    8220
ttaatagact ggatggaggc ggataaagtt gcaggaccac ttctgcgctc ggcccttccg    8280
gctggctggt ttattgctga taaatctgga gccggtgagc gtggaagccg cggtatcatt    8340
gcagcactgg ggccagatgg taagccctcc cgtatcgtag ttatctacac gacgggagt    8400 caggcaacta tggatgaacg aaatagacag atcgctgaga taggtgcctc actgattaag    8460
cattggtaac tgtcagacca agtttactca tatatacttt agattgattt aaaacttcat    8520
ttttaattta aaaggatcta ggtgaagatc ctttttgata atctcatgac caaaatccct    8580
taacgtgagt tttcgttcca ctgagcgtca gaccccgtag aaaagatcaa aggatcttct    8640
tgagatcctt ttttctgcg cgtaatctgc tgcttgcaaa caaaaaaacc accgctacca    8700
gcggtggttt gtttgccgga tcaagagcta ccaactcttt ttccgaaggt aactggcttc    8760
agcagagcgc agataccaaa tactgtcctt ctagtgtagc cgtagttagg ccaccacttc    8820
```

-continued

```
aagaactctg tagcaccgcc tacatacctc gctctgctaa tcctgttacc agtggctgct    8880
gccagtggcg ataagtcgtg tcttaccggg ttggactcaa gacgatagtt accggataag    8940
gcgcagcggt cgggctgaac gggggttcg tgcacacagc ccagcttgga gcgaacgacc     9000
tacaccgaac tgagatacct acagcgtgag ctatgagaaa gcgccacgct tcccgaaggg    9060
agaaaggcgg acaggtatcc ggtaagcggc agggtcggaa caggagagcg cacgagggag    9120
cttccagggg gaaacgcctg gtatctttat agtcctgtcg ggtttcgcca cctctgactt    9180
gagcgtcgat ttttgtgatg ctcgtcaggg gggcggagcc tatggaaaaa cgccagcaac    9240 gcggccttt tacggttcct ggccttttgc tggccttttg ctcacatgt                 9289
```

<210> SEQ ID NO 44
<211> LENGTH: 61
<212> TYPE: DNA
<213> ORGANISM: Sus scrofa

<400> SEQUENCE: 44

```
ctcaggtctt ggctccccgg tgcccggggc ctctggccct tgtcgacgat tctggatcag    60
t                                                                   61
```

<210> SEQ ID NO 45
<211> LENGTH: 60
<212> TYPE: DNA
<213> ORGANISM: Sus scrofa

<400> SEQUENCE: 45

```
ctcaggtctt ggctccccgg tgcccggggc ctctgcccct gtcgacgatt ctggatcagt    60
```

<210> SEQ ID NO 46
<211> LENGTH: 60
<212> TYPE: DNA
<213> ORGANISM: Sus scrofa

<400> SEQUENCE: 46

```
ctcaggtctt ggctccccgg tgcccggtgc ccgggcccct gtcgacgatt ctggatcagt    60
```

<210> SEQ ID NO 47
<211> LENGTH: 60
<212> TYPE: DNA
<213> ORGANISM: Sus scrofa

<400> SEQUENCE: 47

```
ctcaggtctt ggctccccgg tgcccggtgc ccgggcccct gtcgacgatt ctggatcagt    60
```

<210> SEQ ID NO 48
<211> LENGTH: 54
<212> TYPE: DNA
<213> ORGANISM: Sus scrofa
<220> FEATURE:
<221> NAME/KEY: misc_feature
<222> LOCATION: (6)..(7)
<223> OTHER INFORMATION: n is a, c, g, or t

<400> SEQUENCE: 48

```
atcagnnctt ggctccccgg tgcccggggc ctctggccac gattctggat cagt          54
```

<210> SEQ ID NO 49
<211> LENGTH: 54
<212> TYPE: DNA
<213> ORGANISM: Sus scrofa

```
<400> SEQUENCE: 49
ctcaggtctt ggctccccgg tgcccggggc ctctgtcgac gattctggat cagt          54

<210> SEQ ID NO 50
<211> LENGTH: 54
<212> TYPE: DNA
<213> ORGANISM: Sus scrofa

<400> SEQUENCE: 50
ctcaggtctt ggctccccgg tgcccggggc ctctgtcgac gattctggat cagt          54

<210> SEQ ID NO 51
<211> LENGTH: 59
<212> TYPE: DNA
<213> ORGANISM: Sus scrofa

<400> SEQUENCE: 51
ctcaggtctt ggctccccgg tgcccggggc ctctggccct tgtcgacttc tggatcagt     59

<210> SEQ ID NO 52
<211> LENGTH: 60
<212> TYPE: DNA
<213> ORGANISM: Sus scrofa

<400> SEQUENCE: 52
ctcaggtctt ggctccccgg tgcccggggc ctctgcccct gtcgacgatt ctggatcagt    60

<210> SEQ ID NO 53
<211> LENGTH: 24
<212> TYPE: DNA
<213> ORGANISM: Sus scrofa

<400> SEQUENCE: 53
gcaccagctg aagaccaccg gagg                                           24

<210> SEQ ID NO 54
<211> LENGTH: 23
<212> TYPE: DNA
<213> ORGANISM: Sus scrofa

<400> SEQUENCE: 54
gctggtgcga ggagtacacg tgg                                            23

<210> SEQ ID NO 55
<211> LENGTH: 65
<212> TYPE: DNA
<213> ORGANISM: Sus scrofa

<400> SEQUENCE: 55
gaatctcgcc acgtgtactc ctcgcaccag ctgaagacac cggagggcgt ggtggtgtgt    60
cccat                                                                65

<210> SEQ ID NO 56
<211> LENGTH: 64
<212> TYPE: DNA
<213> ORGANISM: Sus scrofa

<400> SEQUENCE: 56
gaatctcgcc acgtgtactc ctcgcaccag ctgaagacac cggagggcgt ggtggtgttc    60
ccat                                                                 64
```

```
<210> SEQ ID NO 57
<211> LENGTH: 65
<212> TYPE: DNA
<213> ORGANISM: Sus scrofa

<400> SEQUENCE: 57
gaatctcgcc acgtgtactc ctcgcaccag ctgaagacac cggagggcgt ggtggtgtgt    60
cccat                                                                65

<210> SEQ ID NO 58
<211> LENGTH: 64
<212> TYPE: DNA
<213> ORGANISM: Sus scrofa

<400> SEQUENCE: 58
gaatctcgcc acgtgtactc ctcgcaccag ctgaagacac cggagggcgt ggtggtgttc    60
ccat                                                                 64

<210> SEQ ID NO 59
<211> LENGTH: 65
<212> TYPE: DNA
<213> ORGANISM: Sus scrofa

<400> SEQUENCE: 59
gaatctcgcc acgtgtactc ctcgcaccag ctgaagacac cggagggcgt ggtggtgtgt    60
cccat                                                                65

<210> SEQ ID NO 60
<211> LENGTH: 65
<212> TYPE: DNA
<213> ORGANISM: Sus scrofa

<400> SEQUENCE: 60
gaatctcgcc acgtgtactc ctcgcaccag ctgaagacac cggagggcgt ggtggtgtgt    60
cccat                                                                65

<210> SEQ ID NO 61
<211> LENGTH: 65
<212> TYPE: DNA
<213> ORGANISM: Sus scrofa

<400> SEQUENCE: 61
gaatctcgcc acgtgtactc ctcgcaccag ctgaagacac cggagggcgt ggtggtgtgt    60
cccat                                                                65

<210> SEQ ID NO 62
<211> LENGTH: 1000
<212> TYPE: DNA
<213> ORGANISM: Bovine

<400> SEQUENCE: 62
gaaggatggg ggtgggggcg tttgcagaca tgaagttttg ttgaaaggac agaaaaactg    60
aggcccaggg agacgggtct ttccagaggt cacagagcac cttgcaggcc aagcaagcac   120
cagagacaac aggaaagacc cccttccaca tctccatggg gaattaaagt cagaaggaat   180
caaaggtgag gagtgggccc tttaaatcct aagctccacc tttgcttaga agggtctttg   240
ggaatataaa aggggggtgca gttcctctct gctcctgaaa accatcagct gctcctgtct   300
gcgggccccc agcccacttc tctccagcca cccaccacca acactccccc gggtgccatg   360
```

| | |
|---|---:|
| cagctgccac cctttgacat gtggaaggac tacttcaacc tgagccaagt ggtgctggca | 420 |
| ctgatccaga gtcggggca agggttggag acccaaggga ctggggagcc gagacccggg | 480 |
| ccccatgtgg agcaggatca ggggcagggc ggacgcgggg ctggcggggg cctggccacc | 540 |
| ctgtgcaact tttgcaaaca caatggagag tctcgccacg tgtactcctc acaccagctg | 600 |
| aagacccegg agggcgtggt ggtgtgtccc attctgcggc attatgtatg tccctgtgc | 660 |
| ggggccaccg gggaccaggc ccacacactc aagtactgcc cactcaacgg aggacagcag | 720 |
| tctctctacc gccgcagtgg gcgcaactca gccggccgca aggtcaagcg ctgaagaccg | 780 |
| tcaggtaccc accgctgca gccccaaccc tccctggttc agccctccca gcccctgga | 840 |
| ctctccccat ctatggactc gtcaggccct ttggaatgtc tgactctcag tacttgatcc | 900 |
| ctgctggatc ctggaacaac ggaggcagtg ggaagccagg ccaactccgc ggccccttag | 960 |
| aactctcagc tctccggact cttgtctgcg agtgtctgtg | 1000 |

```
<210> SEQ ID NO 63
<211> LENGTH: 417
<212> TYPE: DNA
<213> ORGANISM: Bovine

<400> SEQUENCE: 63
```

| | |
|---|---:|
| atgcagctgc caccctttga catgtggaag gactacttca acctgagcca agtggtgctg | 60 |
| gcactgatcc agagtcgggg gcaagggttg gagacccaag ggactgggga gccgagaccc | 120 |
| gggccccatg tggagcagga tcaggggcag gcggacgcg gggctggcgg gggcctggcc | 180 |
| accctgtgca acttttgcaa acacaatgga gagtctcgcc acgtgtactc ctcacaccag | 240 |
| ctgaagaccc cggagggcgt ggtggtgtgt cccattctgc ggcattatgt atgtcccctg | 300 |
| tgcggggcca ccggggacca ggcccacaca ctcaagtact gccccactca acggaggacag | 360 |
| cagtctctct accgccgcag tgggcgcaac tcagccggcc gcaaggtcaa gcgctga | 417 |

```
<210> SEQ ID NO 64
<211> LENGTH: 20
<212> TYPE: DNA
<213> ORGANISM: Bovine

<400> SEQUENCE: 64
```

| | |
|---|---:|
| agacgggtct ttccagaggt | 20 |

```
<210> SEQ ID NO 65
<211> LENGTH: 20
<212> TYPE: DNA
<213> ORGANISM: Bovine

<400> SEQUENCE: 65
```

| | |
|---|---:|
| aagctccacc tttgcttaga | 20 |

```
<210> SEQ ID NO 66
<211> LENGTH: 21
<212> TYPE: DNA
<213> ORGANISM: Bovine

<400> SEQUENCE: 66
```

| | |
|---|---:|
| ctttgcttag aagggtcttt t | 21 |

```
<210> SEQ ID NO 67
<211> LENGTH: 20
<212> TYPE: DNA
<213> ORGANISM: Bovine
```

```
<400> SEQUENCE: 67
ggtctttggg aatataaaag                                                 20

<210> SEQ ID NO 68
<211> LENGTH: 19
<212> TYPE: DNA
<213> ORGANISM: Bovine

<400> SEQUENCE: 68
ggcaagggtt ggagaccca                                                  19

<210> SEQ ID NO 69
<211> LENGTH: 20
<212> TYPE: DNA
<213> ORGANISM: Bovine

<400> SEQUENCE: 69
gccgagaccc gggccccatg                                                 20

<210> SEQ ID NO 70
<211> LENGTH: 20
<212> TYPE: DNA
<213> ORGANISM: Bovine

<400> SEQUENCE: 70
cccatgtgga gcaggatcag                                                 20

<210> SEQ ID NO 71
<211> LENGTH: 19
<212> TYPE: DNA
<213> ORGANISM: Bovine

<400> SEQUENCE: 71
tccccatctc tggactcgt                                                  19

<210> SEQ ID NO 72
<211> LENGTH: 20
<212> TYPE: DNA
<213> ORGANISM: Bovine

<400> SEQUENCE: 72
tctggactcg tccggccctt                                                 20

<210> SEQ ID NO 73
<211> LENGTH: 20
<212> TYPE: DNA
<213> ORGANISM: Bovine

<400> SEQUENCE: 73
tctcagtact tgatccctgc                                                 20

<210> SEQ ID NO 74
<211> LENGTH: 20
<212> TYPE: DNA
<213> ORGANISM: Bovine

<400> SEQUENCE: 74
acaagagtcc ggagagctga                                                 20

<210> SEQ ID NO 75
<211> LENGTH: 54
<212> TYPE: DNA
```

```
<213> ORGANISM: Sus scrofa

<400> SEQUENCE: 75
tgccatgcag ctgccaccct ttgacatgtg aaggactac ttcaacctga gcca        54

<210> SEQ ID NO 76
<211> LENGTH: 18
<212> TYPE: DNA
<213> ORGANISM: Sus scrofa

<400> SEQUENCE: 76
tgccatgcag ctgccacc                                                18

<210> SEQ ID NO 77
<211> LENGTH: 18
<212> TYPE: DNA
<213> ORGANISM: Sus scrofa

<400> SEQUENCE: 77
tggctcaggt tgaagtag                                                18

<210> SEQ ID NO 78
<211> LENGTH: 52
<212> TYPE: DNA
<213> ORGANISM: Sus scrofa

<400> SEQUENCE: 78
tttgacatgt ggaaggacta cttcaacctg agccaggtgg tgttgggact ga          52

<210> SEQ ID NO 79
<211> LENGTH: 18
<212> TYPE: DNA
<213> ORGANISM: Sus scrofa

<400> SEQUENCE: 79
tttgacatgt ggaaggac                                                18

<210> SEQ ID NO 80
<211> LENGTH: 18
<212> TYPE: DNA
<213> ORGANISM: Sus scrofa

<400> SEQUENCE: 80
tcagtcccaa caccacct                                                18

<210> SEQ ID NO 81
<211> LENGTH: 53
<212> TYPE: DNA
<213> ORGANISM: Sus scrofa

<400> SEQUENCE: 81
tcaacctgag ccaggtggtg ttgggactga tccagaatcg tcgacaaggg cca         53

<210> SEQ ID NO 82
<211> LENGTH: 18
<212> TYPE: DNA
<213> ORGANISM: Sus scrofa

<400> SEQUENCE: 82
tcaacctgag ccaggtgg                                                18

<210> SEQ ID NO 83
<211> LENGTH: 16
```

```
<212> TYPE: DNA
<213> ORGANISM: Sus scrofa

<400> SEQUENCE: 83
gcccttgtcg acgatt                                                     16

<210> SEQ ID NO 84
<211> LENGTH: 19
<212> TYPE: DNA
<213> ORGANISM: Sus scrofa

<400> SEQUENCE: 84
gcgggcagta cttgagtgt                                                  19

<210> SEQ ID NO 85
<211> LENGTH: 20
<212> TYPE: DNA
<213> ORGANISM: Sus scrofa

<400> SEQUENCE: 85
ccagaaaacc ttctgctgct                                                 20

<210> SEQ ID NO 86
<211> LENGTH: 26
<212> TYPE: DNA
<213> ORGANISM: Sus scrofa

<400> SEQUENCE: 86
ccagaatcgt cgacaagggc cagagg                                          26

<210> SEQ ID NO 87
<211> LENGTH: 26
<212> TYPE: DNA
<213> ORGANISM: Sus scrofa

<400> SEQUENCE: 87
ggtcttagca gctgttcccg gtctcc                                          26

<210> SEQ ID NO 88
<211> LENGTH: 24
<212> TYPE: DNA
<213> ORGANISM: Bovine

<400> SEQUENCE: 88
caccggtctt tgggaatata aaag                                            24

<210> SEQ ID NO 89
<211> LENGTH: 24
<212> TYPE: DNA
<213> ORGANISM: Bovine

<400> SEQUENCE: 89 aaaccttta tattcccaaa gacc                                             24

<210> SEQ ID NO 90
<211> LENGTH: 23
<212> TYPE: DNA
<213> ORGANISM: Bovine

<400> SEQUENCE: 90
caccgtcttt gggaatataa aag                                             23

<210> SEQ ID NO 91
```

```
<211> LENGTH: 23
<212> TYPE: DNA
<213> ORGANISM: Bovine

<400> SEQUENCE: 91 aaaccttttat tattcccaaa gac                                              23

<210> SEQ ID NO 92
<211> LENGTH: 25
<212> TYPE: DNA
<213> ORGANISM: Bovine

<400> SEQUENCE: 92
caccgctttg cttagaaggg tcttt                                             25

<210> SEQ ID NO 93
<211> LENGTH: 25
<212> TYPE: DNA
<213> ORGANISM: Bovine

<400> SEQUENCE: 93
aaacaaagac ccttctaagc aaagc                                             25

<210> SEQ ID NO 94
<211> LENGTH: 23
<212> TYPE: DNA
<213> ORGANISM: Bovine

<400> SEQUENCE: 94
caccgttgct tagaagggtc ttt                                               23

<210> SEQ ID NO 95
<211> LENGTH: 22
<212> TYPE: DNA
<213> ORGANISM: Bovine

<400> SEQUENCE: 95
aacaaagacc cttctaagca ac                                                22

<210> SEQ ID NO 96
<211> LENGTH: 25
<212> TYPE: DNA
<213> ORGANISM: Bovine

<400> SEQUENCE: 96
caccgagctc cacctttgct tagaa                                             25

<210> SEQ ID NO 97
<211> LENGTH: 25
<212> TYPE: DNA
<213> ORGANISM: Bovine

<400> SEQUENCE: 97
aaacttctaa gcaaaggtgg agctc                                             25

<210> SEQ ID NO 98
<211> LENGTH: 23
<212> TYPE: DNA
<213> ORGANISM: Bovine

<400> SEQUENCE: 98
caccgctcca cctttgctta gaa                                               23
```

```
<210> SEQ ID NO 99
<211> LENGTH: 23
<212> TYPE: DNA
<213> ORGANISM: Bovine

<400> SEQUENCE: 99
aaacttctaa gcaaaggtgg agc                                             23

<210> SEQ ID NO 100
<211> LENGTH: 24
<212> TYPE: DNA
<213> ORGANISM: Bovine

<400> SEQUENCE: 100
caccggcaag ggttggagac ccaa                                            24

<210> SEQ ID NO 101
<211> LENGTH: 24
<212> TYPE: DNA
<213> ORGANISM: Bovine

<400> SEQUENCE: 101
aaacttgggt ctccaaccct tgcc                                            24

<210> SEQ ID NO 102
<211> LENGTH: 23
<212> TYPE: DNA
<213> ORGANISM: Bovine

<400> SEQUENCE: 102
caccgcaagg gttggagacc caa                                             23

<210> SEQ ID NO 103
<211> LENGTH: 23
<212> TYPE: DNA
<213> ORGANISM: Bovine

<400> SEQUENCE: 103
aaacttgggt ctccaaccct tgc                                             23

<210> SEQ ID NO 104
<211> LENGTH: 24
<212> TYPE: DNA
<213> ORGANISM: Bovine

<400> SEQUENCE: 104
caccgccgag acccgggccc catg                                            24

<210> SEQ ID NO 105
<211> LENGTH: 24
<212> TYPE: DNA
<213> ORGANISM: Bovine

<400> SEQUENCE: 105
aaaccatggg gcccgggtct cggc                                            24

<210> SEQ ID NO 106
<211> LENGTH: 21
<212> TYPE: DNA
<213> ORGANISM: Bovine

<400> SEQUENCE: 106
caccgagacc cgggccccat g                                               21
```

```
<210> SEQ ID NO 107
<211> LENGTH: 21
<212> TYPE: DNA
<213> ORGANISM: Bovine

<400> SEQUENCE: 107
aaaccatggg gcccgggtct c                                          21

<210> SEQ ID NO 108
<211> LENGTH: 25
<212> TYPE: DNA
<213> ORGANISM: Bovine

<400> SEQUENCE: 108
caccgcccat gtggagcagg atcag                                      25

<210> SEQ ID NO 109
<211> LENGTH: 25
<212> TYPE: DNA
<213> ORGANISM: Bovine

<400> SEQUENCE: 109
aaacctgatc ctgctccaca tgggc                                      25

<210> SEQ ID NO 110
<211> LENGTH: 23
<212> TYPE: DNA
<213> ORGANISM: Bovine

<400> SEQUENCE: 110
caccgcatgt ggagcaggat cag                                        23

<210> SEQ ID NO 111
<211> LENGTH: 23
<212> TYPE: DNA
<213> ORGANISM: Bovine

<400> SEQUENCE: 111
aaacctgatc ctgctccaca tgc                                        23

<210> SEQ ID NO 112
<211> LENGTH: 25
<212> TYPE: DNA
<213> ORGANISM: Bovine

<400> SEQUENCE: 112
caccgtcccc atctctggac tcgtc                                      25

<210> SEQ ID NO 113
<211> LENGTH: 25
<212> TYPE: DNA
<213> ORGANISM: Bovine

<400> SEQUENCE: 113
aaacgacgag tccagagatg gggac                                      25

<210> SEQ ID NO 114
<211> LENGTH: 23
<212> TYPE: DNA
<213> ORGANISM: Bovine

<400> SEQUENCE: 114
caccgcccat ctctggactc gtc                                        23
```

<210> SEQ ID NO 115
<211> LENGTH: 23
<212> TYPE: DNA
<213> ORGANISM: Bovine

<400> SEQUENCE: 115
aaacgacgag tccagagatg ggc                                           23

<210> SEQ ID NO 116
<211> LENGTH: 25
<212> TYPE: DNA
<213> ORGANISM: Bovine

<400> SEQUENCE: 116
caccgtctgg actcgtccgg ccctt                                         25

<210> SEQ ID NO 117
<211> LENGTH: 201
<212> TYPE: DNA
<213> ORGANISM: Bovine

<400> SEQUENCE: 117
tgggcccttt aaatcctaag ctccacctttt gcttagaagg gtctttggga atataaaagg   60
gggtgcagtt cctgagccaa gtggtgctgg cactgatcca gagtcggggg caagggttgg   120
agacccaagg gactggggag ccgagacccg gccccatgtg gagcaggatc aggggcaggg   180
cggacgcggg gccggcgggg g                                            201

<210> SEQ ID NO 118
<211> LENGTH: 132
<212> TYPE: DNA
<213> ORGANISM: Bovine

<400> SEQUENCE: 118
tgggcccttt aaatcctaag ctccaccttt gcttagaagg gtctttggga atataacaag   60
ggactgggga gccgagaccc ggccccatgt ggagcaggat caggggcagg gcggacgcgg   120
ggccggcggg gg                                                      132

<210> SEQ ID NO 119
<211> LENGTH: 132
<212> TYPE: DNA
<213> ORGANISM: Bovine

<400> SEQUENCE: 119
tgggcccttt aaatcctaag ctccaccttt gcttagaagg gtctttggga atataacaag   60
ggactgggga gccgagaccc ggccccatgt ggagcaggat caggggcagg gcggacgcgg   120
ggccggcggg gg                                                      132

<210> SEQ ID NO 120
<211> LENGTH: 119
<212> TYPE: DNA
<213> ORGANISM: Bovine

<400> SEQUENCE: 120
tgggcccttt aaatcctaag ctccaccttt gcttagaagg gtctttggga ctggggagcc   60
gagacccggc cccatgtgga gcaggatcag gggcagggcg gacgcggggc cggcggggg   119

<210> SEQ ID NO 121

```
<211> LENGTH: 119
<212> TYPE: DNA
<213> ORGANISM: Bovine

<400> SEQUENCE: 121
tgggcccttt aaatcctaag ctccaccttt gcttagaagg gtctttggga ctggggagcc      60
gagacccggc cccatgtgga gcaggatcag gggcagggcg gacgcggggc cggcggggg     119

<210> SEQ ID NO 122
<211> LENGTH: 112
<212> TYPE: DNA
<213> ORGANISM: Bovine

<400> SEQUENCE: 122
tgggcccttt aaatcctaag ctccaccttt gcttagaagg gtctttggga gccgagaccc      60
ggccccatgt ggagcaggat caggggcagg gcggacgcgg ggccggcggg gg            112

<210> SEQ ID NO 123
<211> LENGTH: 201
<212> TYPE: DNA
<213> ORGANISM: Bovine

<400> SEQUENCE: 123
tgggcccttt aaatcctaag ctccaccttt gcttagaagg gtctttggga atataaaagg      60
gggtgcagtt cctgagccaa gtggtgctgg cactgatcca gagtcggggg caagggttgg     120
agacccaagg gactggggag ccgagacccg gccccatgtg gagcaggatc aggggcaggg     180
cggacgcggg gccggcgggg g                                               201

<210> SEQ ID NO 124
<211> LENGTH: 129
<212> TYPE: DNA
<213> ORGANISM: Bovine

<400> SEQUENCE: 124
tgggcccttt aaatcctaag ctccaccttt gcttagaagg gtctttgggg gtgcagttcc      60
tgagccaagt ggtgctggca ctgatccaga gtcgggggca agggttggag acccaaggga     120
ctggggagc                                                             129

<210> SEQ ID NO 125
<211> LENGTH: 103
<212> TYPE: DNA
<213> ORGANISM: Bovine

<400> SEQUENCE: 125
tgggcccttt aaatcctaag ctccaccttt gcttagaagg gtctttggga atataacatg      60
tggagcagga tcaggggcag gcggacgcg gggccggcgg ggg                        103

<210> SEQ ID NO 126
<211> LENGTH: 104
<212> TYPE: DNA
<213> ORGANISM: Bovine

<400> SEQUENCE: 126
tgggcccttt aaatcctaag ctccaccttt gcttagaagg gtctttggga atataaacat      60
gtggagcagg atcaggggca gggcggacgc ggggccggcg gggg                      104

<210> SEQ ID NO 127
<211> LENGTH: 106
```

```
<212> TYPE: DNA
<213> ORGANISM: Bovine

<400> SEQUENCE: 127
tgggcccttt aaatcctaag ctccaccttt gcttagaagg gtctttggga gtgcagttcc      60
atgtggagca ggatcagggg cagggcggac gcgggccgg cggggg                    106

<210> SEQ ID NO 128
<211> LENGTH: 103
<212> TYPE: DNA
<213> ORGANISM: Bovine

<400> SEQUENCE: 128
tgggcccttt aaatcctaag ctccaccttt gcttagaagg gtctttggga atataacatg      60
tggagcagga tcaggggcag gcggacgcg gggccggcgg ggg                       103

<210> SEQ ID NO 129
<211> LENGTH: 201
<212> TYPE: DNA
<213> ORGANISM: Bovine

<400> SEQUENCE: 129
tgggcccttt aaatcctaag ctccaccttt gcttagaagg gtctttggga atataaaagg      60
gggtgcagtt cctgagccaa gtggtgctgg cactgatcca gagtcggggg caagggttgg    120
agacccaagg gactggggag ccgagacccg gccccatgtg gagcaggatc aggggcaggg    180
cggacgcggg gccggcgggg g                                              201

<210> SEQ ID NO 130
<211> LENGTH: 48
<212> TYPE: DNA
<213> ORGANISM: Bovine

<400> SEQUENCE: 130
tgggcccttt aaatcctaag ctccaccttt gcttagaagg gtctaagg                  48

<210> SEQ ID NO 131
<211> LENGTH: 89
<212> TYPE: DNA
<213> ORGANISM: Bovine

<400> SEQUENCE: 131
tgggcccttt aaatcctaag ctccaccttt gcttagaagg gtctttggga atataatcag      60
gggcagggcg gacgcggggc cggcggggg                                       89

<210> SEQ ID NO 132
<211> LENGTH: 88
<212> TYPE: DNA
<213> ORGANISM: Bovine

<400> SEQUENCE: 132
tgggcccttt aaatcctaag ctccaccttt gcttagaagg gtctttggga atataacagg      60
ggcagggcgg acgcggggcc ggcggggg                                        88

<210> SEQ ID NO 133
<211> LENGTH: 45
<212> TYPE: DNA
<213> ORGANISM: Bovine

<400> SEQUENCE: 133
```

```
tgggcccttt aaatcctaag ctccaccttt gctggccggg ggggg        45
```

<210> SEQ ID NO 134
<211> LENGTH: 62
<212> TYPE: DNA
<213> ORGANISM: Bovine

<400> SEQUENCE: 134

```
tgggcccttt aaatcctaag ctccaccttt gcttagaagg cggacgcgg ggccggcggg   60
gg                                                                 62
```

<210> SEQ ID NO 135
<211> LENGTH: 200
<212> TYPE: DNA
<213> ORGANISM: Bovine

<400> SEQUENCE: 135

```
tgggcccttt aaatcctaag ctccaccttt gcttagaagg gtctttggga atataaaagg   60
gggtgcagtt cctgagccaa gtggtgctgg cactgatcca gagtcggggg caagggttgg  120
agacccaagg gactggggag ccgagacccg gccccatgtg gagcaggatc aggggcaggg  180
cggacgcggg gccggcgggg                                              200
```

<210> SEQ ID NO 136
<211> LENGTH: 132
<212> TYPE: DNA
<213> ORGANISM: Bovine

<400> SEQUENCE: 136

```
tgggcccttt aaatcctaag ctccaccttt gcttagaagg gtctttggga atataacaag   60
ggactgggga gccgagaccc ggccccatgt ggagcaggat caggggcagg gcggacgcgg  120
ggccggcggg gg                                                      132
```

<210> SEQ ID NO 137
<211> LENGTH: 132
<212> TYPE: DNA
<213> ORGANISM: Bovine

<400> SEQUENCE: 137

```
tgggcccttt aaatcctaag ctccaccttt gcttagaagg gtctttggga atataacaag   60
ggactgggga gccgagaccc ggccccatgt ggagcaggat caggggcagg gcggacgcgg  120
ggccggcggg gg                                                      132
```

<210> SEQ ID NO 138
<211> LENGTH: 132
<212> TYPE: DNA
<213> ORGANISM: Bovine

<400> SEQUENCE: 138

```
tgggcccttt aaatcctaag ctccaccttt gcttagaagg gtctttggga atataacaag   60
ggactgggga gccgagaccc ggccccatgt ggagcaggat caggggcagg gcggacgcgg  120
ggccggcggg gg                                                      132
```

<210> SEQ ID NO 139
<211> LENGTH: 132
<212> TYPE: DNA
<213> ORGANISM: Bovine

<400> SEQUENCE: 139
tgggcccttt aaatcctaag ctccaccttt gcttagaagg gtctttggga atataacaag        60
ggactgggga gccgagaccc ggccccatgt ggagcaggat caggggcagg gcggacgcgg       120
ggccggcggg gg                                                          132

<210> SEQ ID NO 140
<211> LENGTH: 132
<212> TYPE: DNA
<213> ORGANISM: Bovine

<400> SEQUENCE: 140
tgggcccttt aaatcctaag ctccaccttt gcttagaagg gtctttggga atataacaag        60
ggactgggga gccgagaccc ggccccatgt ggagcaggat caggggcagg gcggacgcgg       120
ggccggcggg gg                                                          132

<210> SEQ ID NO 141
<211> LENGTH: 201
<212> TYPE: DNA
<213> ORGANISM: Bovine

<400> SEQUENCE: 141
tgggcccttt aaatcctaag ctccaccttt gcttagaagg gtctttggga atataaaagg        60
gggtgcagtt cctgagccaa gtggtgctgg cactgatcca gagtcggggg caagggttgg       120
agacccaagg gactggggag ccgagacccg gccccatgtg gagcaggatc aggggcaggg       180
cggacgcggg gccggcgggg g                                                201

<210> SEQ ID NO 142
<211> LENGTH: 98
<212> TYPE: DNA
<213> ORGANISM: Bovine

<400> SEQUENCE: 142
tgggcccttt aaatcctaag ctccaccttt gcttagaagg gtctttggga atatgtggag        60
caggatcagg ggcagggcgg acgcggggcc ggcggggg                                98

<210> SEQ ID NO 143
<211> LENGTH: 103
<212> TYPE: DNA
<213> ORGANISM: Bovine

<400> SEQUENCE: 143
tgggcccttt aaatcctaag ctccaccttt gcttagaagg gtctttggga atataacatg        60
tggagcagga tcaggggcag ggcggacgcg gggccggcgg ggg                         103

<210> SEQ ID NO 144
<211> LENGTH: 89
<212> TYPE: DNA
<213> ORGANISM: Bovine

<400> SEQUENCE: 144
tgggcccttt aaatcctaag ctccaccttt gcttagaagg gtctttggga atatgatcag        60
gggcagggcg gacgcggggc cggcggggg                                         89

<210> SEQ ID NO 145
<211> LENGTH: 89
<212> TYPE: DNA
<213> ORGANISM: Bovine

```
<400> SEQUENCE: 145
tgggcccttt aaatcctaag ctccacctttt gcttagaagg gtctttggga gcaggatcag    60
gggcagggcg gacgcggggc cggcggggg                                      89

<210> SEQ ID NO 146
<211> LENGTH: 103
<212> TYPE: DNA
<213> ORGANISM: Bovine

<400> SEQUENCE: 146
tgggcccttt aaatcctaag ctccacctttt gcttagaagg gtctttggga atataacatg    60
tggagcagga tcaggggcag ggcggacgcg gggccggcgg ggg                      103

<210> SEQ ID NO 147
<211> LENGTH: 201
<212> TYPE: DNA
<213> ORGANISM: Bovine

<400> SEQUENCE: 147
tgggcccttt aaatcctaag ctccacctttt gcttagaagg gtctttggga atataaaagg    60
gggtgcagtt cctgagccaa gtggtgctgg cactgatcca gagtcggggg caagggttgg   120
agacccaagg gactggggag ccgagacccg gccccatgtg gagcaggatc agggggcaggg  180 cggacgcggg gccggcgggg g                                             201

<210> SEQ ID NO 148
<211> LENGTH: 68
<212> TYPE: DNA
<213> ORGANISM: Bovine

<400> SEQUENCE: 148
tgggcccttt aaatcctaag ctccacctttt gcttctcagg ggcagggcgg acgcggggcc    60
ggcggggg                                                             68

<210> SEQ ID NO 149
<211> LENGTH: 70
<212> TYPE: DNA
<213> ORGANISM: Bovine

<400> SEQUENCE: 149
tgggcccttt aaatcctaag ctccacctttt gcttagaagg gtctttgggc ggacgcgggg    60
ccggcggggg                                                           70

<210> SEQ ID NO 150
<211> LENGTH: 88
<212> TYPE: DNA
<213> ORGANISM: Bovine

<400> SEQUENCE: 150
gggcccttta atcctaagc tccacctttg cttagaaggg tctttgggaa tataatcagg     60
ggcagggcgg acgcggggcc ggcggggg                                       88

<210> SEQ ID NO 151
<211> LENGTH: 67
<212> TYPE: DNA
<213> ORGANISM: Bovine

<400> SEQUENCE: 151
tgggcccttt aaatcctaag ctccacctttt gcttagaagg gcagggcgga cgcggggccg    60
```

```
gcggggg                                                              67

<210> SEQ ID NO 152
<211> LENGTH: 125
<212> TYPE: DNA
<213> ORGANISM: Bovine

<400> SEQUENCE: 152
tgggcccttt aaatcctaag ctccacctttt gcttagaagt ggtgctggca ctgatccaga    60
gtcgggggca agggttggag acccaaggga ctggggagcc gagacccggc cccatgtgga   120
gcagg                                                               125

<210> SEQ ID NO 153
<211> LENGTH: 25
<212> TYPE: DNA
<213> ORGANISM: Bovine

<400> SEQUENCE: 153
aaacaagggc cggacgagtc cagac                                          25

<210> SEQ ID NO 154
<211> LENGTH: 21
<212> TYPE: DNA
<213> ORGANISM: Bovine

<400> SEQUENCE: 154
caccggactc gtccggccct t                                              21

<210> SEQ ID NO 155
<211> LENGTH: 21
<212> TYPE: DNA
<213> ORGANISM: Bovine

<400> SEQUENCE: 155
aaacaagggc cggacgagtc c                                              21

<210> SEQ ID NO 156
<211> LENGTH: 25
<212> TYPE: DNA
<213> ORGANISM: Bovine

<400> SEQUENCE: 156
caccgtctca gtacttgatc cctgc                                          25

<210> SEQ ID NO 157
<211> LENGTH: 25
<212> TYPE: DNA
<213> ORGANISM: Bovine

<400> SEQUENCE: 157
aaacgcaggg atcaagtact gagac                                          25

<210> SEQ ID NO 158
<211> LENGTH: 23
<212> TYPE: DNA
<213> ORGANISM: Bovine

<400> SEQUENCE: 158
caccgtcagt acttgatccc tgc                                            23

<210> SEQ ID NO 159
```

```
<211> LENGTH: 23
<212> TYPE: DNA
<213> ORGANISM: Bovine

<400> SEQUENCE: 159
aaacgcaggg atcaagtact gac                                              23

<210> SEQ ID NO 160
<211> LENGTH: 22
<212> TYPE: DNA
<213> ORGANISM: Sus scrofa

<400> SEQUENCE: 160
gatcagtccc aacaccacct gg                                               22

<210> SEQ ID NO 161
<211> LENGTH: 22
<212> TYPE: DNA
<213> ORGANISM: Sus scrofa

<400> SEQUENCE: 161
ccaggtggtg ttgggactga tc                                               22

<210> SEQ ID NO 162
<211> LENGTH: 23
<212> TYPE: DNA
<213> ORGANISM: Sus scrofa

<400> SEQUENCE: 162
gaatcgtcga caagggccag agg                                              23

<210> SEQ ID NO 163
<211> LENGTH: 42
<212> TYPE: DNA
<213> ORGANISM: Sus scrofa

<400> SEQUENCE: 163
ctacttcaac ctgagccagg tggtgttggg actgatccag aa                         42

<210> SEQ ID NO 164
<211> LENGTH: 37
<212> TYPE: DNA
<213> ORGANISM: Sus scrofa

<400> SEQUENCE: 164
ctacttcaac ctgagccagg ttgggactga tccagaa                               37

<210> SEQ ID NO 165
<211> LENGTH: 39
<212> TYPE: DNA
<213> ORGANISM: Sus scrofa

<400> SEQUENCE: 165
ctacttcaac ctgagccagg tgttgggact gatccagaa                             39

<210> SEQ ID NO 166
<211> LENGTH: 39
<212> TYPE: DNA
<213> ORGANISM: Sus scrofa

<400> SEQUENCE: 166
ctacttcaac ctgagccagg gactgggact gatccagaa                             39
```

```
<210> SEQ ID NO 167
<211> LENGTH: 43
<212> TYPE: DNA
<213> ORGANISM: Sus scrofa

<400> SEQUENCE: 167
ctacttcaac ctgagccagg tgggtgttgg gactgatcca gaa                43

<210> SEQ ID NO 168
<211> LENGTH: 41
<212> TYPE: DNA
<213> ORGANISM: Sus scrofa

<400> SEQUENCE: 168
ctacttcaac ctgagccagg tgtgttggga ctgatccaga a                  41

<210> SEQ ID NO 169
<211> LENGTH: 37
<212> TYPE: DNA
<213> ORGANISM: Sus scrofa

<400> SEQUENCE: 169
ctacttcaac ctgagccagg ttgggaccga tccagaa                       37

<210> SEQ ID NO 170
<211> LENGTH: 39
<212> TYPE: DNA
<213> ORGANISM: Sus scrofa

<400> SEQUENCE: 170
ctacttcaac ctgagccagg tgtttgggact gatccagaa                    39

<210> SEQ ID NO 171
<211> LENGTH: 39
<212> TYPE: DNA
<213> ORGANISM: Sus scrofa

<400> SEQUENCE: 171
ctacttcaac ctgagccagg tgttgggact gatccagaa                     39

<210> SEQ ID NO 172
<211> LENGTH: 32
<212> TYPE: DNA
<213> ORGANISM: Sus scrofa

<400> SEQUENCE: 172
ctacttcaac ctgagccagg actgatccag aa                            32

<210> SEQ ID NO 173
<211> LENGTH: 39
<212> TYPE: DNA
<213> ORGANISM: Sus scrofa

<400> SEQUENCE: 173
ctacttcaac ctgagccagg tgttgggact gatccagaa                     39

<210> SEQ ID NO 174
<211> LENGTH: 39
<212> TYPE: DNA
<213> ORGANISM: Sus scrofa

<400> SEQUENCE: 174
ctacttcaac ctgagccagg tgttgggact gatccagaa                     39
```

<210> SEQ ID NO 175
<211> LENGTH: 37
<212> TYPE: DNA
<213> ORGANISM: Sus scrofa

<400> SEQUENCE: 175
ctacttcaac ctgagccagg ttgggactga tccagaa                                37

<210> SEQ ID NO 176
<211> LENGTH: 39
<212> TYPE: DNA
<213> ORGANISM: Sus scrofa

<400> SEQUENCE: 176
ctacttcaac ctgagtcagg tgttgggact gatccagaa                              39

<210> SEQ ID NO 177
<211> LENGTH: 45
<212> TYPE: DNA
<213> ORGANISM: Sus scrofa

<400> SEQUENCE: 177
ctacttcaac ctaagccagg ttgaagtgtt gggactgatc cagaa                       45

<210> SEQ ID NO 178
<211> LENGTH: 39
<212> TYPE: DNA
<213> ORGANISM: Sus scrofa

<400> SEQUENCE: 178
ctacttcaac ctgagccagg tgttgggact gatccagaa                              39

<210> SEQ ID NO 179
<211> LENGTH: 41
<212> TYPE: DNA
<213> ORGANISM: Sus scrofa

<400> SEQUENCE: 179
ctacttcaac ctgagccagg tgtgttggga ctgatccaga a                           41

<210> SEQ ID NO 180
<211> LENGTH: 38
<212> TYPE: DNA
<213> ORGANISM: Sus scrofa

<400> SEQUENCE: 180
ctacctcaac ctgagccagg ggtgggactg atccagaa                               38

<210> SEQ ID NO 181
<211> LENGTH: 41
<212> TYPE: DNA
<213> ORGANISM: Sus scrofa

<400> SEQUENCE: 181
ctacttcaac ctgagcctgg tgtgttggga ctgatccaga a                           41

<210> SEQ ID NO 182
<211> LENGTH: 39
<212> TYPE: DNA
<213> ORGANISM: Sus scrofa

<400> SEQUENCE: 182
ctacttcaac ctgagccagg tgttgggact gatccagaa                              39

<210> SEQ ID NO 183
<211> LENGTH: 39
<212> TYPE: DNA
<213> ORGANISM: Sus scrofa

<400> SEQUENCE: 183
ctacttcaac ctgagccagg tgttgggact gatccagaa                    39

<210> SEQ ID NO 184
<211> LENGTH: 38
<212> TYPE: DNA
<213> ORGANISM: Sus scrofa

<400> SEQUENCE: 184
ctacttcaac ctgagccagg tctgggactg atccagaa                     38

<210> SEQ ID NO 185
<211> LENGTH: 16
<212> TYPE: DNA
<213> ORGANISM: Sus scrofa

<400> SEQUENCE: 185
tgggactgat ccagaa                                             16

<210> SEQ ID NO 186
<211> LENGTH: 45
<212> TYPE: DNA
<213> ORGANISM: Sus scrofa

<400> SEQUENCE: 186
ctacttcaac ctgagccagg ttgaagtgtt gggactgatc cagaa              45

<210> SEQ ID NO 187
<211> LENGTH: 45
<212> TYPE: DNA
<213> ORGANISM: Sus scrofa

<400> SEQUENCE: 187
ctacttcaac ctgagccagg ttgaagtgtt gggactgatc cagaa              45

<210> SEQ ID NO 188
<211> LENGTH: 39
<212> TYPE: DNA
<213> ORGANISM: Sus scrofa

<400> SEQUENCE: 188
ctacttcaac ctgagccagg tgttgggact gatccagaa                    39

<210> SEQ ID NO 189
<211> LENGTH: 39
<212> TYPE: DNA
<213> ORGANISM: Sus scrofa

<400> SEQUENCE: 189
ctacttcaac ctgagccagg tgttgggact gatccagaa                    39

<210> SEQ ID NO 190
<211> LENGTH: 37
<212> TYPE: DNA
<213> ORGANISM: Sus scrofa

<400> SEQUENCE: 190

-continued

```
ctacttcaac ctgagccagg ttgggactga tccagaa                                    37

<210> SEQ ID NO 191
<211> LENGTH: 37
<212> TYPE: DNA
<213> ORGANISM: Sus scrofa

<400> SEQUENCE: 191
ctacttcaac ctgagccagg ttgggactga tccagaa                                    37

<210> SEQ ID NO 192
<211> LENGTH: 41
<212> TYPE: DNA
<213> ORGANISM: Sus scrofa

<400> SEQUENCE: 192
ctacttcaac ctgagccagg tgtgttggga ctgatcaata a                               41

<210> SEQ ID NO 193
<211> LENGTH: 38
<212> TYPE: DNA
<213> ORGANISM: Sus scrofa

<400> SEQUENCE: 193
ctacttcaac ctgagccagt gttgggactg atccagaa                                   38

<210> SEQ ID NO 194
<211> LENGTH: 39
<212> TYPE: DNA
<213> ORGANISM: Sus scrofa

<400> SEQUENCE: 194
ctacttcaac ctgagccagg tgttgggact gatccagaa                                  39

<210> SEQ ID NO 195
<211> LENGTH: 42
<212> TYPE: DNA
<213> ORGANISM: Sus scrofa

<400> SEQUENCE: 195
ctacttcaac ctgagccagg cggggttggg actgatccag aa                              42

<210> SEQ ID NO 196
<211> LENGTH: 39
<212> TYPE: DNA
<213> ORGANISM: Sus scrofa

<400> SEQUENCE: 196
ctacttcaac ctgagccagg tgttgggact gatccagaa                                  39

<210> SEQ ID NO 197
<211> LENGTH: 37
<212> TYPE: DNA
<213> ORGANISM: Sus scrofa

<400> SEQUENCE: 197
ctacttcaac ctgagccagg ttgggactga tccagaa                                    37

<210> SEQ ID NO 198
<211> LENGTH: 41
<212> TYPE: DNA
<213> ORGANISM: Sus scrofa

<400> SEQUENCE: 198
```

```
ctacttcaac ctgagccagg tgtgttggga ctgatccaga a                41
```

<210> SEQ ID NO 199
<211> LENGTH: 21
<212> TYPE: DNA
<213> ORGANISM: Sus scrofa

<400> SEQUENCE: 199

```
ctacttcaac ctgagccaga a                                     21
```

<210> SEQ ID NO 200
<211> LENGTH: 51
<212> TYPE: DNA
<213> ORGANISM: Sus scrofa

<400> SEQUENCE: 200

```
atccagaatc gtcgacaagg gccagaggcc ccgggcaccg gggagccaag a    51
```

<210> SEQ ID NO 201
<211> LENGTH: 44
<212> TYPE: DNA
<213> ORGANISM: Sus scrofa

<400> SEQUENCE: 201

```
atccagaatc gtcgacaagg gccccgggca ccggggagcc aaga            44
```

<210> SEQ ID NO 202
<211> LENGTH: 44
<212> TYPE: DNA
<213> ORGANISM: Sus scrofa

<400> SEQUENCE: 202

```
atccagaatc gtcgacaagg gccccgggca ccggggagcc aaga            44
```

<210> SEQ ID NO 203
<211> LENGTH: 50
<212> TYPE: DNA
<213> ORGANISM: Sus scrofa

<400> SEQUENCE: 203

```
atccagaatc gtcgacgacg cgagaagccc cgggcaccgg ggagccaaga      50
```

<210> SEQ ID NO 204
<211> LENGTH: 40
<212> TYPE: DNA
<213> ORGANISM: Sus scrofa

<400> SEQUENCE: 204

```
atccagaatc gtcgaggccc cgggcaccgg ggagccaaga                 40
```

NANOS KNOCK-OUT THAT ABLATES GERMLINE CELLS

CROSS-REFERENCE TO RELATED APPLICATIONS

This is a divisional application of U.S. Ser. No. 15/325,777, filed Jan. 12, 2017, which is a National Phase application claiming priority to PCT/US15/40379, filed Jul. 14, 2015, which claims priority to provisional application U.S. Ser. No. 62/023,996, filed on Jul. 14, 2014, all of which are herein incorporated by reference in their entirety.

FIELD OF THE INVENTION

The present invention relates to a genetically edited non-human livestock animal. The methods of the present invention provide for modified NANOS genes in animals so that males lack germline cells while females are fertile. The resultant male animals are then available for spermatogonial stem cell transplantation and use in breeding programs.

BACKGROUND TO THE INVENTION

Genetic gain in livestock can be described as the improvement in production characteristics within a population from generation-to-generation as a result of selective breeding. Exploiting this principle is an important aspect for food animal production to enhance growth efficiency, animal health, and product quality for the consumer while also reducing environmental impact. In livestock production, the majority of genetic gain is made via selective breeding of desirable sires. Thus, expanding the availability of sperm from individual sires can greatly impact food animal production on a global scale. Artificial insemination (AI) methodology has been exploited in commercial livestock production to improve production characteristics worldwide. Despite advances, expansive use of elite boars and bulls for AI in the livestock breeding industry has been hampered due to limitations in the absolute number of sperm that can be collected from an individual. For boars, ejaculates are collected 1-2 times a week and a single ejaculate yields ~20 AI doses. Each sow is inseminated 2-3 times during a given estrous cycle. Thus, less than 20 sows can be bred each week with sperm from a desirable sire. Thus, novel approaches for expanding the output and availability of gametes from desirable sires and preserving the germline are of significant need.

Spermatogenesis produces millions of sperm daily and the foundation for such vast numbers is provided by the actions of the undifferentiated spermatogonial population that contains spermatogonial stem cells (SSCs). One of the unique properties of SSCs is their ability to colonize the testis of a recipient animal and regenerate spermatogenesis following transplantation. SSC transplantation methodology has been developed for rodent models and adaptation of this approach to pigs would provide an effective breeding tool for expanding and preserving the germline and genetic merit of individual sires. Critical aspects for applying SSC transplantation methodology are: 1) production of recipient animals that lack an endogenous germline, but possess intact support cell populations (i.e. Sertoli and Leydig cells); 2) expansion of the relatively rare donor SSCs in vitro to generate optimal numbers for successful transplantation into several recipient males; and 3) injection of SSCs into recipient testis.

The efficiency of donor SSC colonization is influenced by the environment of recipient testes. Elimination of endogenous germ cells is critical for accessibility of donor SSCs to engraft within seminiferous tubules of recipient testes. In addition, spermatogenesis is regulated by intimate interaction between germ cells and testis support cell populations including Sertoli and Leydig cells. Thus, health of somatic cells at the time of transplantation impacts the success of donor SSC colonization. For rodents, treating adult males with chemotoxic drugs, notably the alkylating agent busulfan and localized testicular irradiation have each been used to effectively prepare recipients for SSC transplantation. While both treatments result in depletion of endogenous germ cells and donor SSCs are able to engraft, the function of somatic support cells is often negatively impacted and some endogenous germ cells always remain leading to regeneration of a mix of donor and endogenous spermatogenesis. In mice, the greatest success of SSC transplantation involves the use of recipients that are sterile due to inactivation of genes required for germ cell survival at the earliest stages of spermatogenesis. Partial ablation of spermatogenesis in which the spermatogonial population persists is not effective for preparing recipients. In such a case, chemotoxic drugs must still be used to eliminate the persisting spermatogonia thereby opening niches for donor SSCs to engraft. Males in which survival of primordial germ cells (PGCs), gonocytes, or SSCs is compromised provide an ideal recipient.

For pigs and other large domestic animals, treatment with chemotoxic drugs to prepare recipient males is not feasible due to the requirement of high dosage of drugs for complete elimination of germ cells. These treatments often produce unintended consequences of toxicity on bone marrow stem cells and other tissue-specific stem cells. Additionally, feces and urine would need to be collected as a bio-hazardous waste. Local testicular irradiation is a potential alternative that overcomes the limitations of chemotoxic drug treatment, however the dose of irradiation needs to be precisely controlled and the procedure inflicts damage on the supporting cells, including Leydig cells thereby negatively affecting generation of donor-derived spermatogenesis. Ideal recipients are males lacking an endogenous germline due to a genetic deficiency that leaves the somatic support cell population functionally intact.

As can be seen, there is a need in the art for animals where the male has no germ cells but retains functional somatic cells and is thus eligible for SSC transplantation, while ideally females are fertile.

SUMMARY OF THE INVENTION

The present invention provides animals and methods for spermatogonial stem cell transplantation by creating recipient animals that have modulated NANOS expression. The animals have inactivated or otherwise modulated NANOS gene activity resulting in males which lack functional germ cells yet retain functional somatic cells, and females which are fertile. These animals can be created using any of a number of protocols such as knock-out technology or gene-editing.

Thus an embodiment of the invention is a genetically edited or modified livestock animal comprising a genome with inactivation of a NANOS gene selective for germline cell function.

Yet another embodiment of the invention is a process of making a livestock animal comprising introducing to a livestock animal cell or livestock embryo, an agent that specifically binds to a chromosomal target site of the cell and causes a double-stranded DNA break or otherwise inactivates a NANOS gene therein using gene editing methods such as the Clustered Regularly Interspaced Short Palindromic Repeats (CRISPR)/Cas system, Transcription Activator-Like Effector Nucleases (TALENs), Zinc Finger Nucleases (ZFN), or recombinase fusion proteins.

Yet another embodiment of the invention is a process of producing a male sperm donor for livestock breeding with a desired spermatogonial stem cell genetic component comprising; collecting donor SSCs from a desired male donor, proliferating SSCs in vitro, and thereafter transplanting donor SSCs to a NANOS2 –/– male so that spermatogenic colonies are generated and persist for a long period of time with the donor germline cells.

Yet another embodiment of the invention includes the production of livestock animals comprising natural mating and/or artificial insemination of female livestock with donor sperm from the recipient NANAOS2 –/– male.

Also described herein is the use of one or more particular NANOS loci in tandem with a polypeptide capable of effecting cleavage and/or integration of specific nucleic acid sequences within the NANOS loci. Examples of the use of NANOS loci in tandem with a polypeptide capable of effecting cleavage and/or integration of the NANOS loci include a polypeptide selected from the group consisting of zinc finger proteins, meganucleases, TAL domains, TALENs, RNA-guided CRISPR/Cas recombinases, leucine zippers, and others known to those in the art. Particular examples include a chimeric ("fusion") protein comprising a site-specific DNA binding domain polypeptide and cleavage domain polypeptide (e.g., a nuclease), such as a ZFN protein comprising a zinc-finger polypeptide and a FokI nuclease polypeptide. In certain aspects, described herein are polypeptides comprising a DNA-binding domain that specifically binds to a NANOS gene. In some embodiments such a polypeptide may also comprise a nuclease (cleavage) domain or half-domain (e.g., a ZFN, a recombinase, a transposase, or a homing endonuclease, including a homing endonuclease with a modified DNA-binding domain, TAL domains, TALENs, RNA-guided CRISPR/Cas), and/or a ligase domain, such that the polypeptide may induce a targeted double-stranded break, and/or facilitate recombination of a nucleic acid of interest at the site of the break. In particular embodiments, a DNA-binding domain that targets a NANOS locus may be a DNA-cleaving functional domain. The foregoing polypeptides may be used in some embodiments to introduce an exogenous nucleic acid into the genome of a host organism (e.g., an animal species) at one or more NANOS loci. In certain embodiments, the DNA-binding domains comprise a zinc finger protein with one or more zinc fingers (e.g., 2, 3, 4, 5, 6, 7, 8, 9 or more zinc fingers), which is engineered (non-naturally occurring) to bind to any sequence within a NANOS gene. Any of the zinc finger proteins described herein may bind to a target site within the coding sequence of the target gene or within adjacent sequences (e.g., promoter or other expression elements). In certain embodiments, the zinc finger protein binds to a target site in a NANOS gene, for example, approximately 20 bases in exon 1.

Further embodiments will become evident from the detailed description of the invention which follows.

DESCRIPTION OF THE FIGURES

FIGS. 3A, 3B and 3C show the sequence of guide RNA binding sequence (SEQ ID NO:15 and SEQ ID NO:16). FIG. 3C shows the construct with the guides, the human U6 promoter, sgRNA binding sequence and terminator sequence. U6 promoter sequence (SEQ ID NO: 18), target sequence (SEQ ID NO:19), gRNA scaffold (SEQ ID NO: 20) terminal sequence (SEQ ID NO: 21).

FIG. 5C1-5C3 show the entire construct sequence (SEQ ID NO:43).

FIG. 8 shows the sequences of the bovine indels compared to wild type.
    pSL32 & pSL38: WT (SEQ ID NO:117), Clone 1 (SEQ ID NO:118); CLONE 2 (SEQ ID NO:119); CLONE 3 (SEQ ID NO:120); CLONE 4 (SEQ ID NO:121); CLONE 5 (SEQ ID NO:122).
    pSL32 & pSL39: WT (SEQ ID NO:123), Clone 1 (SEQ ID NO:124); CLONE 2 (SEQ ID NO:125); CLONE 3 (SEQ ID NO:126); CLONE 4 (SEQ ID NO:127); CLONE 5 (SEQ ID NO:128).
    pSL32 & pSL42 WT (SEQ ID NO:129), Clone 1 (SEQ ID NO:130); CLONE 2 (SEQ ID NO:131); CLONE 3 (SEQ ID NO:132); CLONE 4 (SEQ ID NO:133); CLONE 5 (SEQ ID NO:134).
    pSL33 & pSL38 WT (SEQ ID NO:135), Clone 1 (SEQ ID NO:136); CLONE 2 (SEQ ID NO:137); CLONE 3 (SEQ ID NO:138); CLONE 4 (SEQ ID NO:139); CLONE 5 (SEQ ID NO:140).
    pSL33 & pSL39 WT (SEQ ID NO:141), Clone 1 (SEQ ID NO:142); CLONE 2 (SEQ ID NO:143); CLONE 3 (SEQ ID NO:144); CLONE 4 (SEQ ID NO:145); CLONE 5 (SEQ ID NO:146).

pSL33 & pSL42 WT (SEQ ID NO:147), Clone 1 (SEQ ID NO:148); CLONE 2 (SEQ ID NO:149); CLONE 3 (SEQ ID NO:150); CLONE 4 (SEQ ID NO:151); CLONE 5 (SEQ ID NO:152).

Figure 9A:
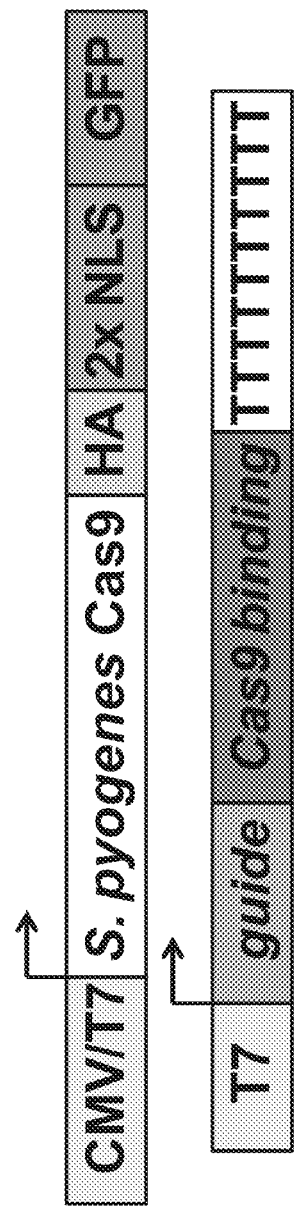
Figure 9B:
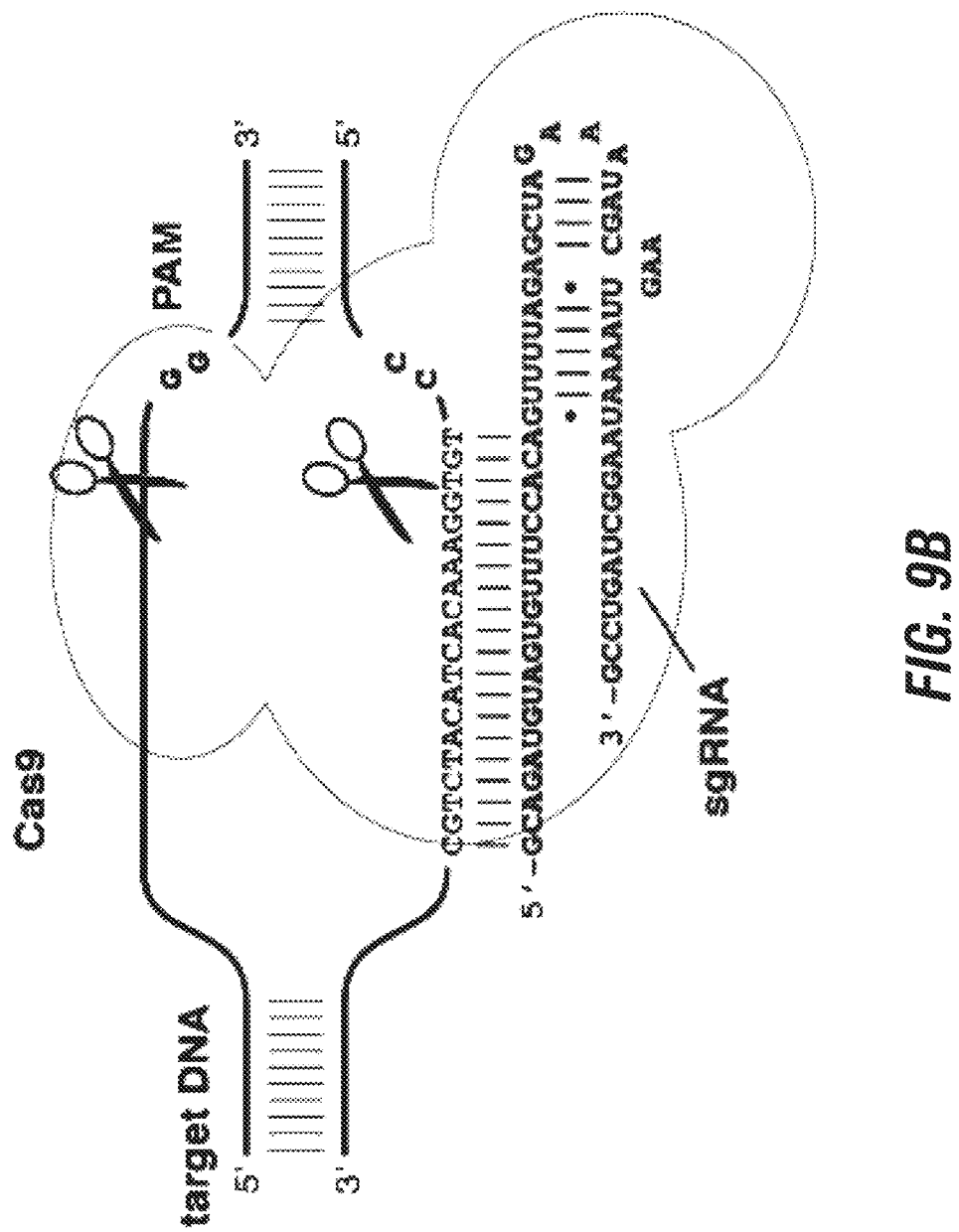
Figure 9C:
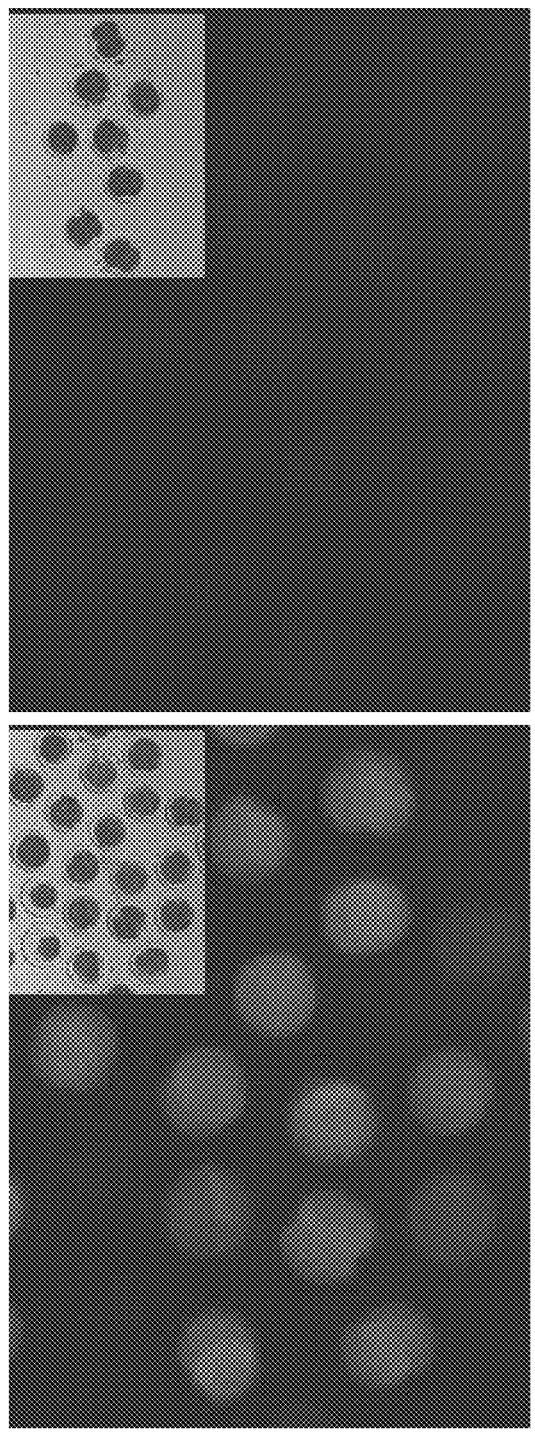

FIGS. 9A-9D show CRISPR mediated gene targeting of NANOS2 locus in porcine embryos. FIG. 9A is a schematic of CMV promoter for mammalian expression, and T7 for in vitro transcription of Cas9:GFP expression vector: HA tag, and NLS: nuclear localization signals for nuclear localization of expressed Cas9 nuclease protein. A T7 promoter driven chimeric single guide RNA (sgRNA) expression cassette harbouring the guide RNA and Cas9 binding sequence. FIG. 9B is a schematic of Cas9, sgRNA mediated targeting of intended genomic sequence. FIG. 9C is a fluorescent micrograph of porcine 1-cell embryos, either non-injected (right) or injected (left) with RNA from both panel A cassettes (Cas9:GFP and guide) on day-2 confirming expression from the Cas9:GFP. Bright field images of the developing embryos are shown in the inset. FIG. 9D shows sequencing of injected embryos depicts various degrees of indels, which were often bi-allelic. Wild type sequence is shown in the top lane with highlighted sequences showing target guide sequence (yellow), and PAM motif (AGG, green) in reverse orientation. NANOS2 (SEQ ID NO:29); N1-1 (SEQ ID NO:30); N1-2 (SEQ ID NO:31); N3-2 (SEQ ID NO:32); N3-3 (SEQ ID NO: 33); N5-2 (SEQ ID NO:34); N5-3 (SEQ ID NO:35); N6-1 (SEQ ID NO:36); N7-2 (SEQ ID NO:37); N7-3 (SEQ ID NO:38); N10-2 (SEQ ID NO:39); N11-2 (SEQ ID NO:40); N12-2 (SEQ ID NO:41) N12-3 (SEQ ID NO:42).

FIG. 10A shows the sequencing of porcine embryos injected with two sgRNAs. As shown in the figure, injections of two sgRNAs resulted in the deletion of a large segment of NANOS2 locus, and an insertion of extraneous sequence (red) in NANOS2 alleles. NANOS (SEQ ID NO:26); NN6-1 (SEQ ID NO:27); NN7-1 and NN7-2 (SEQ ID NO: 28). FIG. 10B shows further indel sequence from blastocysts NANOS (SEQ ID NO:44); N3-1-3 (SEQ ID NO:45); N3-2-3 (SEQ ID NO:46); N3-6-2 (SEQ ID NO:47); N3-7-3 (SEQ ID NO:48); N3-8-3 (SEQ ID NO:49); N3-10-2 (SEQ ID NO:50); N3-12-2 (SEQ ID NO:51); N3-12-3 (SEQ ID NO:52).

FIG. 11 shows the pair (Nickase pair) of single guide RNAs are designed to target on opposite strands. Both the sgRNAs are shown in the box in the figure, with the reverse strand highlighted in yellow. PAM motifs of both sgRNAs are highlighted in green. No modifications were identified around the target site. sgRNA1 (SEQ ID NO:53); sgRNA2 (SEQ ID NO:54); NANOS (SEQ ID NO:55); N2-3 (SEQ ID NO:56); N3-1 (SEQ ID NO:57); N4-2 (SEQ ID NO:58); N5-2 (SEQ ID NO:59); N6-3 (SEQ ID NO:60); N7-1 (SEQ ID NO:61).

Figure 12:
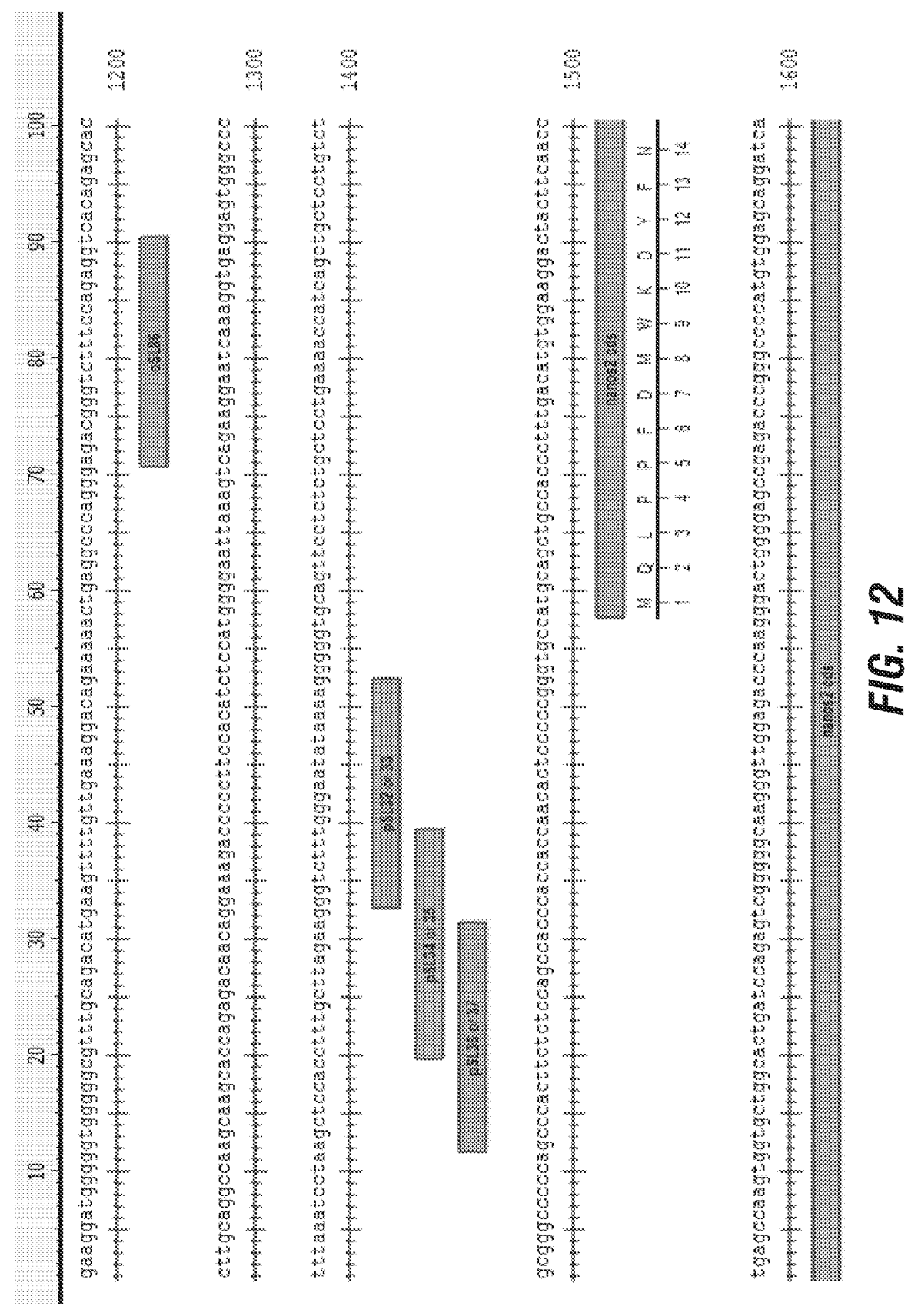

FIG. 12 shows the bovine NANOS2 sequence with the designed guides and amplification primers annotated. Entire nucleotide sequence (SEQ ID NO:62); NANOS 2 CDS (SEQ ID NO:63); oSL86 (SEQ ID NO:64); pSL36 or 37 (SEQ ID NO:65); pSL34 or 35 (SEQ ID NO:66); pSL32 or 33 (SEQ ID NO:67); pSL38 or 39 (SEQ ID NO:68); pSL39 or 40 (SEQ ID NO:69); pSL41 or 42 (SEQ ID NO:70); pSL43 or 44 (SEQ ID NO:71); pSL45 or 46 (SEQ ID NO:72); pSL47 or 48 (SEQ ID NO:73); oSL87 (SEQ ID NO:74).

FIG. 13 shows the CRISPR/Cas system approach to generate mono- or bi-allelic knockout NANOS2 piglets. The 20 nucleotide guide sequence is underlined and the PAM motif highlighted in yellow (note: guide is in reverse orientation). The CRISPR target sequence is underlined within the NANOS2 ORF. CRISPR guide RNA sequence (SEQ ID NO:160); NANOS2 ORF (SEQ ID NOS:1 and 2); CRISPR target sequence (SEQ ID NO:161).

FIGS. 14A and 14B show the genotypes of CRISPR/Cas mediated NANOS2 mono or bi-allelic knockout piglets. NANOS WT (SEQ ID NO:163); NANOS pig 1-1 (SEQ ID NO:164); NANOS pig 1-2 (SEQ ID NO:165); NANOS pig 1-3 (SEQ ID NO:166); NANOS pig 2-1 (SEQ ID NO:167); NANOS pig 2-4 (SEQ ID NO:168); NANOS pig 3-1 (SEQ ID NO:169); NANOS pig 4-1 (SEQ ID NO:170); NANOS pig 4-2 (SEQ ID NO:171); NANOS pig 10-1 (SEQ ID NO:172); NANOS pig 10-2 (SEQ ID NO:173); NANOS pig 11-1 (SEQ ID NO:174); NANOS pig 11-4 (SEQ ID NO:164); NANOS pig 12-1 (SEQ ID NO:176); NANOS pig 12-2 (SEQ ID NO:177); NANOS piglet #1 Allele-1 (SEQ ID NO:178); NANOS piglet #1 Allele-2 (SEQ ID NO:179); NANOS piglet #2 Allele-1 (SEQ ID NO:180); NANOS piglet #2 Allele-2 (SEQ ID NO:181); NANOS piglet #3 Allele-1 (SEQ ID NO:182); NANOS piglet #3 Allele-2 (SEQ ID NO:183); NANOS piglet #4 Allele-1 (SEQ ID NO:184); NANOS piglet #4 Allele-2 (SEQ ID NO:185); NANOS piglet #5 Allele-1 (SEQ ID NO:186); NANOS piglet #5 Allele-2 (SEQ ID NO:187); NANOS piglet #6 Allele-1 (SEQ ID NO:188); NANOS piglet #6 Allele-2 (SEQ ID NO:189); NANOS piglet #7 Allele-1 (SEQ ID NO:164); NANOS piglet #7 Allele-2 (SEQ ID NO:164); NANOS piglet #8 Allele-1 (SEQ ID NO:192); NANOS piglet #8 Allele-2 (SEQ ID NO:193); NANOS piglet #9 Allele-1 (SEQ ID NO:194); NANOS piglet #9 Allele-2 (SEQ ID NO:195); NANOS piglet #10 Allele-1 (SEQ ID NO:196); NANOS piglet #10 Allele-2 (SEQ ID NO:164); NANOS piglet #11 Allele-1 (SEQ ID NO:198); NANOS piglet #11 Allele-2 (SEQ ID NO:199).

FIG. 15 shows the genotypes of NANOS2 null male and female piglets generated by SCNT. In the figure, the 20 nucleotide guide sequence targeting NANOS2 (SEQ ID NO:162) is highlighted in green and underlined followed by the 3 nt PAM motif (highlighted in blue). In the male knockouts, both alleles have 7 nt deletions in the NANOS2 ORF causing disruption of NANOS2 gene. In the female, one allele has 1 nt deletion and several altered nucleotide sequences, and the second allele has 11 nt deletions. Together, these alleles render the female animals null for NANOS2.

Figure 16:
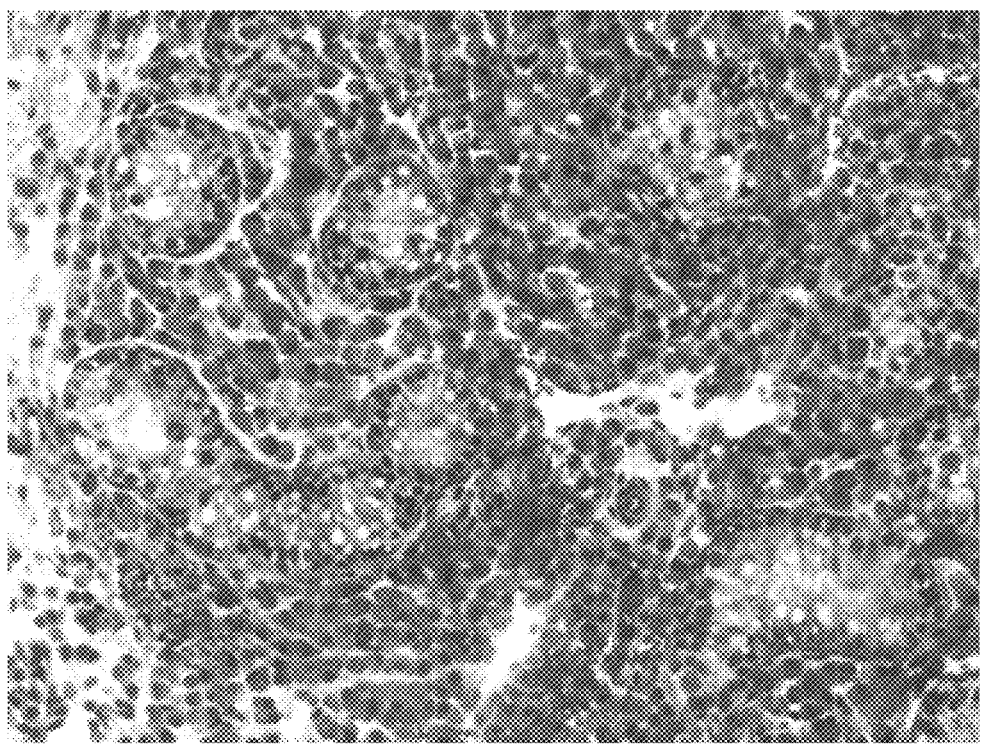

FIG. 16 shows a representative image of cross-sections from testicular biopsies of Nanos2 homozygous knockout pigs at 3 months of age. The image of the cross-sectional biopsy was generated using light microscopy and shows intact seminiferous cords and the presence of somatic support cells. In addition, FIG. 16 shows the absence of multiple layers of germ cells within the cords.

DETAILED DESCRIPTION OF THE INVENTION

The present invention now will be described more fully with reference to the accompanying examples. The invention may be embodied in many different forms and should not be construed as limited to the embodiments set forth in this application; rather, these embodiments are provided so that this disclosure will satisfy applicable legal requirements.

Many modifications and other embodiments of the invention will come to mind to one skilled in the art to which this invention pertains, having the benefit of the teachings presented in the descriptions and the drawings herein. As a result, it is to be understood that the invention is not to be limited to the specific embodiments disclosed and that modifications and other embodiments are intended to be included within the scope of the appended claims. Although specific terms are used in the specification, they are used in a generic and descriptive sense only and not for purposes of limitation.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e. g., Diagnostic Molecular Microbiology: Principles and Applications, D. H. Persing et al., Ed., American Society for Microbiology, Washington, D.C. (1993). The product of amplification is termed an amplicon.

The term "conservatively modified variants" applies to both amino acid and nucleic acid sequences. With respect to particular nucleic acid sequences, "conservatively modified variants" refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another: [1] Alanine (A), Serine (S), Threonine (T); [2] Aspartic acid (D), Glutamic acid (E); [3] Asparagine (N), Glutamine (Q); [4] Arginine (R), Lysine (K); [5] Isoleucine (I), Leucine (L), Methionine (M), Valine (V); and [6] Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of a native (nonsynthetic), endogenous, biologically active form of the specified protein. Methods to determine whether a sequence is full-length are well known in the art including such exemplary techniques as northern or western blots, primer extension, S1 protection, and ribonuclease protection. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells.

The term "hybridization complex" includes reference to a duplex nucleic acid structure formed by two single-stranded nucleic acid sequences selectively hybridized with each other.

The term "introduced" in the context of inserting a nucleic acid into a cell is equivalent to "transfection" or "transformation" or "transduction," and includes reference to the incorporation of a nucleic acid into a eukaryotic or prokaryotic cell where the nucleic acid may be incorporated into the genome of the cell (e. g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment—the isolated material optionally comprises material not found with the material in its natural environment; or (2) if the material is in its natural environment, the material has been synthetically altered by deliberate human intervention to a composition and/or placed at a location in the cell (e.g., genome or subcellular organelle) not native that material. The alteration to yield the synthetic material can be performed on the material within, or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "mutation" includes reference to alterations in the nucleotide sequence of a polynucleotide, such as for example a gene or coding DNA sequence (CDS), compared to the wild-type sequence. The term includes, without limitation, substitutions, insertions, frameshifts, deletions, inversions, translocations, duplications, splice-donor site mutations, point-mutations or the like.

As used herein, "nucleic acid" includes reference to a deoxyribonucleotide or ribonucleotide polymer in either single- or double-stranded form, and unless otherwise limited, encompasses conservatively modified variants and known analogues having the essential nature of natural nucleotides in that they hybridize to single-stranded nucleic acids in a manner similar to naturally occurring nucleotides (e. g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, CA (Berger); Sambrook et al., Molecular Cloning-A Laboratory Manual, 2nded, Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary join two protein coding regions, contiguously and in the same reading frame.

As used herein, "polynucleotide" includes reference to a deoxyribopolynucleotide, ribopolynucleotide, or conservatively modified variants; the term may also refer to analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms also may apply to conservatively modified variants and to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, the protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear.

For instance, polypeptides may be branched as a result of ubiquitization, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. Examples of promoters under developmental control include promoters that preferentially initiate transcription in certain tissues, such as testes, ovaries, or placenta. Such promoters are referred to as "tissue preferred". Promoters which initiate transcription only in certain tissue are referred to as "tissue specific". A "cell type" specific promoter primarily drives expression in certain cell types in one or more organs, for example, germ cells in testes or ovaries. An "inducible" or "repressible" promoter is a promoter which is under environmental control. Examples of environmental conditions that may affect transcription by inducible promoters include stress, and temperature. Tissue specific, tissue preferred, cell type specific and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to another nucleic acid sequence or other biologics. When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule.

The term "stringent conditions" or "stringent hybridization conditions" includes reference to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e. g., 10 to 50 nucleotides) and at least about 60° C. for long probes (e.g., greater than 50 nucleotides). Stringent conditions may also be achieved with the addition of destabilizing agents such as formamide. Specificity is typically the function of post-hybridization washes, the critical factors being the ionic strength and temperature of the final wash solution. For DNA/DNA hybrids, the thermal melting point (Tm) can be approximated from the equation of Meinkoth and Wahl, Anal. Biochem., 138: 267-284 (1984): Tm [° C.]=81.5+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1 to 4° C. lower than the Tm; moderately stringent conditions can utilize a hybridization and/or wash at 6 to 10° C. lower than the Tm; low stringency conditions can utilize a hybridization and/or wash at 11 to 20° C. lower than the Tm. Using the equation, hybridization and wash compositions, and desired Tm, those of ordinary skill will understand that variations in the stringency of hybridization and/or wash solutions are inherently described. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic animal, cell or tissue" includes reference to an animal which includes within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a)"reference sequence", (b)"comparison window", (c) "sequence identity", and (d)"percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); and by computerized implementations of these algorithms, including, but not limited to: CLUSTAL in the PC/Gene program by Intelligenetics, Mountain View, California; GAP, BESTFIT, BLAST, FASTA, and TFASTA, and related programs in the GCG Wisconsin Genetics Software Package, Version 10 (available from Accelrys Inc., 9685 Scranton Road, San Diego, California, USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997). Software for performing BLAST analyses is publicly available, for example through the National Center for Biotechnology Information (ncbi.nlm.nih.gov/). This algorithm has been thoroughly described in a number of publications. See, e.g., Altschul S F et al., Gapped BLAST and PSI-BLAST: a new generation of protein database search programs, 25 NUCLEIC ACIDS RES. 3389 (1997); National Center for Biotechnology Information, THE NCBI HANDBOOK [INTERNET], Chapter 16: The BLAST Sequence Analysis Tool (McEntyre J, Ostell J, eds., 2002), available at http://www.ncbi.nlm.nih.gov/books/NBK21097/pdf/ch16.pdf The BLASTP program for amino acid sequences has also been thoroughly described (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP represents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89: 10915).

Multiple alignment of the sequences can be performed using the CLUSTAL method of alignment (Higgins and Sharp (1989) CABIOS. 5: 151-153) with the default parameters (GAPPENALTY=10, GAP LENGTH PENALTY=10). Default parameters for pairwise alignments using the CLUSTAL method include KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions may be calculated according to the algorithm of Meyers and Miller, Computer Applic. Biol. Sci., 4: 11-17 (1988), for example as implemented in the program PC/GENE (Intelligenetics, Mountain View, California, USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "gene editing," "gene edited" "genetically edited" and "gene editing effectors" refer to the use of naturally occurring or artificially engineered nucleases, also referred to as "molecular scissors." The nucleases create specific double-stranded break (DSBs) at desired locations in the genome, which in some cases harnesses the cell's endogenous mechanisms to repair the induced break by natural processes of homologous recombination (HR) and/or nonhomologous end-joining (NHEJ). Gene editing effectors include Zinc Finger Nucleases (ZFNs), Transcription Activator-Like Effector Nucleases (TALENs), the Clustered Regularly Interspaced Short Palindromic Repeats/CAS9 (CRISPR/Cas9) system, and meganuclease re-engineered as homing endonucleases. The terms also include the use of transgenic procedures and techniques, including, for example, where the change is relatively small and/or does not introduce DNA from a foreign species. The terms "genetic manipulation" and "genetically manipulated" include gene editing techniques, as well as and/or in addition to other techniques and processes that alter or modify the nucleotide sequence of a gene or gene, or modify or alter the expression of a gene or genes.

As used herein "homing DNA technology" or "homing technology" covers any mechanisms that allow a specified molecule to be targeted to a specified DNA sequence including Zinc Finger (ZF) proteins, Transcription Activator-Like Effectors (TALEs) meganucleases, and the CRISPR/Cas9 system.

The term "livestock animal" includes animals traditionally raised in livestock farming, such as beef cattle, dairy cattle, pigs, sheep, goats, horses, mules, asses, buffalo, and camels. The term also includes birds raised commercially for meat or eggs (i.e., chickens, turkeys, ducks, geese, guinea fowl, and squabs). This does not include rats, mice, or other rodents.

As used herein "Blastocyst" means an early developmental stage of embryo comprising of inner cell mass (from which embryo proper arises) and a fluid filled cavity typically surrounded by a single layer of trophoblast cells. "Developmental Biology", sixth edition, ed. by Scott F. Gilbert, Sinauer Associates, Inc., Publishers, Sunderland, Mass. (2000)

As used herein "Conditional Knock-out" or "Conditional mutation" means when the knock-out or mutation is achieved when certain conditions are met. These conditions include but are not limited to presence of certain inducing agents, recombinases, antibiotics, and certain temperature or salt levels.

The term "Early stage embryo" means any embryo at embryonic stages between fertilized ovum and blastocyst. Typically, eight cell stage and morula stage embryos are referred to as early stage embryos.

"Embryonic germ cells" or "EG cells" means primordial germ cell derived cells which have the potential to differentiate into all the cell types of body and are as amenable to genetic modification as Embryonic stem cells, to the extent that sometimes the distinction between EG cells and ES cells is ignored. "Developmental Biology", sixth edition, ed. by Scott F. Gilbert, Sinauer Associates, Inc., Publishers, Sunderland, Mass. (2000).

"Embryonic stem cells" or "ES cells" means cultured cells derived from inner cell mass of early stage embryo, which are amenable to genetic modification and which retain their totipotency and can contribute to all organs of resulting chimeric animal if injected into host embryo. "Developmental Biology", sixth edition, ed. by Scott F. Gilbert, Sinauer Associates, Inc., Publishers, Sunderland, Mass. (2000).

As used herein, "Fertilization" means the union of male and female gametes during reproduction resulting into formation of zygote, the earliest developmental stage of an embryo. "Foreign cell" means any cell that can be genetically edited or can be derived from a genetically edited cell and that can contribute towards the germ line of a chimeric embryo when injected or aggregated with a donor blastocyst/embryo. This includes, but is not limited to, embryonic stem (ES) cells, teratocarcinoma stem cells, primordial germ cells, and embryonic germ (EG) cells.

The phrase "Genetically edited" means those animals or embryos or cells which have a desired genetic modification such as a knock-out, knock-in, conditional, inducible, transient or point mutation(s) of any gene or its regulatory mechanism or a transgenic with foreign or modified gene/s or regulatory sequences, or having undergone genomic modification in any way including but not limited to recombination, chromosomal deletion, addition, translocation, rearrangement or addition, deletion or modification of nucleic acid, protein or any other natural or synthetic molecule or organelle, or cytoplasmic or nuclear transfer, leading to inheritable changes.

"Germ cell development" means the process by which certain cells in the early stage developing embryo differentiate into primordial germ cells.

"Germ cell migration" means the process by which primordial germ cells, after originating in the extraembryonic mesoderm travel back in the embryo through allantois (precursor of umbilical cord) and continue to migrate through adjacent yolk sac, hindgut, and dorsal mesentery to finally reach the genital ridge (developing gonad). "Developmental Biology", sixth edition, ed. by Scott F. Gilbert, Sinauer Associates, Inc., Publishers, Sunderland, Mass. (2000).

"Germ line cell" means any cell, at any stage of differentiation towards mature gametes, including mature gametes.

As used herein, the term "Knock-in" means replacement of an endogenous gene with a transgene or with same endogenous gene with some structural modification/s, but retaining the transcriptional control of the endogenous gene.

"Knock-out" means disruption of the structure or regulatory mechanism of a gene. Knock-outs may be generated through homologous recombination of targeting vectors, replacement vectors or hit-and-run vectors or random insertion of a gene trap vector resulting into complete, partial or conditional loss of gene function. "Oogenesis" means the process of generation of mature eggs from the primordial germ cells in females.

"Primordial germ cells" means those cells arising early in the embryonic development that give rise to the spermatogenic lineage via a gonocyte intermediate or female germline via an oogonia intermediate.

"Spermatogenesis" means the process of generation of mature sperms from spermatogonial stem cells in males.

"Wild type" means those animals and blastocysts, embryos or cells derived therefrom, which have not been genetically edited and are usually inbred and outbred strains developed from naturally occurring strains. 0082] A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of naturally occurring zinc finger or TALE proteins. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 5,789,538; 5,925, 523; 6,007,988; 6,013,453; 6,200,759; WO 95/19431; WO 96/06166; WO 98/53057; WO 98/54311; WO 00/27878; WO 01/60970 WO 01/88197, WO 02/099084 and U.S. Publication No. 20110301073.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

Means for generating a double strand DNA break: As used herein, the term "means for generating a double strand DNA break" is intended to invoke the special claiming provisions authorized by Congress in 35 U.S.C. sctn.112, sixth paragraph. Specifically, a "means for generating a double strand DNA break" refers to a molecular structure that is capable of cleaving both strands of a double-stranded DNA molecule. Such structures include polypeptide domains comprised within many known nuclease proteins, for example, the FokI nuclease domain, the catalytic domain is selected from the group consisting of proteins Mme1, Colicin-E7 (CEA7_ECOLX), Colicin-E9, APFL, EndA, Endo I (END1_EC0LI), Human Endo G (NUCG_HUMAN), Bovine Endo G (NUCG_BOVIN), R.HinP1I, I-Bas-1, I-Bmo-1, I-Hmu1, I-Tev-1, I-TevII, I-TevIII, I-Two1, R.Msp1, R.Mva1, NucA, NucM, Vvn, Vvn_CLS, Staphylococcal nuclease (NUC_STAAU), Staphylococcal nuclease (NUC_STAHY), Micrococcal nuclease (NUC_SHIFL), Endonuclease yncB, Endodeoxyribonuclease I (ENRN_BPT7), Metnase, Nb.BsrDI, BsrDI A, Nt.BspD61 (R.BspD61 large subunit), ss.BspD61 (R.BspD61 small subunit), R.PIe1, Mly1, Alw1, Mva12691, Bsr1, Bsm1, Nb.BtsCI, Nt.BtsCI, R1.Bts1, R2.Bts1, BbvCI subunit 1, BbvCI subunit 2, BpulOI alpha subunit, BpulOI beta subunit, Bmr1, Bfi1, 1-Cre1, hExo1 (EX01JHUMAN), Yeast Exo1 (EX01_YEAST), E. coli Exo1, Human TREX2, Mouse TREX1, Human TREX1, Bovine TREX1, Rat TREX1, Human DNA2, Yeast DNA2 (DNA2 YEAST).

Means for repairing a double strand DNA break: As used herein, the term "means for repairing a double strand DNA break" is also intended to invoke the special claiming provisions authorized by Congress in 35 U.S.C. sctn.112, sixth paragraph. Specifically, a "means for repairing a double strand DNA break" refers to a molecular structure that is capable of facilitating/catalyzing the joining of the ends of double-stranded DNA molecules, for example, by joining ends generated by cleaving a single double-stranded DNA molecule, or by joining one end generated by cleaving a single double-stranded DNA molecule with the end of an exogenous double-stranded DNA molecule. Such structures include polypeptide domains comprised within many known ligase proteins, for example, Cre recombinase. In some examples, the same molecular structure may serve as both a means for generating a double strand DNA break and a means for repairing a double strand DNA break, where the same structure facilitates both the cleavage and repair of double-stranded DNA molecules (e.g., Hin recombinase).

The induction of the site specific double stranded breaks in the genome induces the host cell DNA repair pathway which resolves the double stranded break through homology-directed repair (HDR) or non-homologous end-joining (NHEJ) repair. It is possible to have one or more ZFN cuts sites on the donor molecule (a single ZFN cut site to linearize the entire donor molecule, 2 of the same ZFN sites to release a smaller donor DNA fragment or 2 different ZFN sites to release a fragment from the donor and a corresponding fragment from the host genomic DNA (DNA replacement).

Thus, the donor polynucleotide can be DNA or RNA, single-stranded and/or double-stranded and can be introduced into a cell in linear or circular form. See, e.g., U.S. Patent Publication Nos. 20100047805 and 20110207221. In certain, embodiments of the present invention may also include linear exogenous (donor) nucleic acid(s), compositions comprising these nucleic acids and methods of making and using these linear donor molecules. In certain embodiments, the linear donor molecule stably persists in the cell into which it is introduced. In other embodiments, the linear donor molecule is modified to resist exonucleolytic cleavage, for example by placing one or more phosphorothioate phosphodiester bonds between one or more base pairs on the ends of the donor molecule. The linear exogenous nucleic acid may also include single stranded specific DNA.

NANOS Gene Editing

NANOS is an evolutionarily conserved family of RNA-binding proteins that are expressed specifically within the germ cells of both invertebrate and vertebrate animals. Ablation of NANOS and its orthologs results in the loss of germ cells in Drosophila, C. elegans, Zebra fish, Xenopus, and mouse. In humans, germ cell loss and infertility are associated with mutations in NANOS genes.

In vertebrates, three NANOS genes have been identified, amongst which NANOS2 and NANOS3 are expressed in PGCs. In mice, Nanos3 protein is first detectable in early PGCs, persists throughout their migration to the genital ridge, and then ceases by embryonic day 15.5 in males or prior to E13.5 in female embryos. In contrast, expression of Nanos2 is restricted to the male gonad. Nanos2 mRNA is first detectable in germ cells that have colonized the male embryonic gonad at around E13.0 after the germ cells begin to interact with gonadal somatic cells. Although the expression transiently decreases at later stages of embryogenesis, Nanos2 mRNA is detectable again in gonocytes during neonatal development.

Ablation of Nanos3 in mice results in the complete loss of germ cells for both sexes due to apoptotic cell death around E8.0. Importantly, inactivation of Nanos2 in mice results in loss of germ cells in male embryos only around E15.5. Thus, the germline is completely lacking at birth in male mice but testicular somatic support cell populations are functionally intact. Also, Nanos2 null males and females are viable and grow to normal maturity. Moreover, Nanos2 null females are of normal fertility. Applicants have demonstrated that NANOS2 is expressed specifically by PGCs in pig embryos.

The NANOS family of genes is known and sequences encoding the same are available through Genbank or other such sources. Sus Scrofa NANOS1 nucleic acid and protein sequences are disclosed at XM_001928298 and herein as SEQ ID NOS: 5 and 6. NANOS2 is at XM_003127232.1 or as herein as SEQ ID NO:1 and 2 and NANOS3 at XM_005661246 or SEQ ID NO:3 and 4 bovine NANOS genes are available at NM_001291904 and SEQ ID NO:9 and 10 (NANOS2); XM_005225796 SEQ ID NO: 11 and 12 (NANOS1); XM_001787922 SEQ ID NO:13 and 14 (NANOS1 alt).

The present disclosure provides a genetically edited animal or animal cell comprising at least one edited chromosomal sequence encoding a NANOS protein or other protein associated with germ cell function or development. The edited chromosomal sequence may be (1) inactivated, (2) modified, or (3) comprise an integrated sequence. An inactivated chromosomal sequence is altered such that a NANOS protein function as it related to spermatogonial cell development is impaired, reduced or eliminated. Thus, a genetically edited animal comprising an inactivated chromosomal sequence may be termed a "knock out" or a "conditional knock out." Similarly, a genetically edited animal comprising an integrated sequence may be termed a "knock in" or a "conditional knock in." Furthermore, a genetically edited animal comprising a modified chromosomal sequence may comprise a targeted point mutation(s) or other modification such that an altered protein product is produced. Briefly, the process comprises introducing into an embryo or cell at least one RNA molecule encoding a targeted zinc finger nuclease and, optionally, at least one accessory polynucleotide. The method further comprises incubating the embryo or cell to allow expression of the zinc finger nuclease, wherein a double-stranded break introduced into the targeted chromosomal sequence by the zinc finger nuclease is repaired by an error-prone non-homologous end-joining DNA repair process or a homology-directed DNA repair process. The method of editing chromosomal sequences encoding a protein associated with germline development using targeted zinc finger nuclease technology is rapid, precise, and highly efficient.

In some embodiments of the present invention, at least one NANOS locus (e.g., a NANOS2 locus) is used as a target site for the site-specific editing. This can include insertion of an exogenous nucleic acid (e.g., a nucleic acid comprising a nucleotide sequence encoding a polypeptide of interest) or deletions of nucleic acids from the locus. In particular embodiments, insertions and/or deletions modified locus. For example, integration of the exogenous nucleic acid and/or deletion of part of the genomic nucleic acid may modify the locus so as to produce a disrupted (i.e., inactivated) NANOS gene.

In some embodiments the edited NANOS locus can comprise a nucleotide sequence selected from the group of SEQ ID NOS: 27, 28, 30, 31, 32, 33, 34, 35, 36, 37, 38, 39, 40, 41, 42, 45, 46, 47, 48, 49, 50, 51, 52, 56, 57, 58, 59, 60, 61, 118, 119, 120, 121, 122, 124, 125, 126, 127, 128, 130, 131, 132, 133, 134, 136, 137, 138, 139, 140, 142, 143, 144, 145, 146, 148, 149, 150, 151, 152, 164, 165, 166, 167, 168, 169, 170, 171, 172, 173, 174, 176, 177, 178, 179, 180, 181, 182, 183, 184, 185, 186, 187, 188, 189, 192, 193, 194, 195, 196, 198, 199, 201, 202, 203, or 204. In some embodiments, an edited NANOS locus may comprise a nucleotide sequence that is substantially identical to a nucleotide sequence selected from the group consisting of SEQ ID NOs: 27, 28, 30, 31, 32, 33, 34, 35, 36, 37, 38, 39, 40, 41, 42, 45, 46, 47, 48, 49, 50, 51, 52, 56, 57, 58, 59, 60, 61, 118, 119, 120, 121, 122, 124, 125, 126, 127, 128, 130, 131, 132, 133, 134, 136, 137, 138, 139, 140, 142, 143, 144, 145, 146, 148, 149, 150, 151, 152, 164, 165, 166, 167, 168, 169, 170, 171, 172, 173, 174, 176, 177, 178, 179, 180, 181, 182, 183, 184, 185, 186, 187, 188, 189, 192, 193, 194, 195, 196, 198, 199, 201, 202, 203, or 204. For example, in some embodiments, a NANOS locus is a NANOS homologue (e.g., an ortholog or a paralog) that comprises a nucleotide sequence that is at least about 85% identical to a nucleotide sequence selected from the group consisting of SEQ ID NOs: 27, 28, 30, 31, 32, 33, 34, 35, 36, 37, 38, 39, 40, 41, 42, 45, 46, 47, 48, 49, 50, 51, 52, 56, 57, 58, 59, 60, 61, 118, 119, 120, 121, 122, 124, 125, 126, 127, 128, 130, 131, 132, 133, 134, 136, 137, 138, 139, 140, 142, 143, 144, 145, 146, 148, 149, 150, 151, 152, 164, 165, 166, 167, 168, 169, 170, 171, 172, 173, 174, 176, 177, 178, 179, 180, 181, 182, 183, 184, 185, 186, 187, 188, 189, 192, 193, 194, 195, 196, 198, 199, 201, 202, 203, or 204. A NANOS homologue may comprise a nucleotide sequence that is, for example and without limitation: at least 80%; at least 85%; at least about 90%; at least about 91%; at least about 92%; at least about 93%; at least about 94%; at least about 95%; at least about 96%; at least about 97%; at least about 98%; at least about 99%; at least about 99.5%; 99.6%, 99.7%, 99.8% and/or at least about 99.9% identical to about 20 contiguous nucleotides of a nucleotide sequence selected from the group consisting of SEQ ID NOs: 27, 28, 30, 31, 32, 33, 34, 35, 36, 37, 38, 39, 40, 41, 42, 45, 46, 47, 48, 49, 50, 51, 52, 56, 57, 58, 59, 60, 61, 118, 119, 120, 121, 122, 124, 125, 126, 127, 128, 130, 131, 132, 133, 134, 136, 137, 138, 139, 140, 142, 143, 144, 145, 146, 148, 149, 150, 151, 152, 164, 165, 166, 167, 168, 169, 170, 171, 172, 173, 174, 176, 177, 178, 179, 180, 181, 182, 183, 184, 185, 186, 187, 188, 189, 192, 193, 194, 195, 196, 198, 199, 201, 202, 203, or 204.

Targeted Integration of a Nucleic Acid at a NANOS Locus

Site-specific integration of an exogenous nucleic acid at a NANOS locus may be accomplished by any technique known to those of skill in the art. In some embodiments, integration of an exogenous nucleic acid at a NANOS locus comprises contacting a cell (e.g., an isolated cell or a cell in a tissue or organism) with a nucleic acid molecule comprising the exogenous nucleic acid. In examples, such a nucleic acid molecule may comprise nucleotide sequences flanking the exogenous nucleic acid that facilitate homologous recombination between the nucleic acid molecule and at least one NANOS locus. In particular examples, the nucleotide sequences flanking the exogenous nucleic acid that facilitate homologous recombination may be complementary to endogenous nucleotides of the NANOS locus. In particular examples, the nucleotide sequences flanking the exogenous nucleic acid that facilitate homologous recombination may be complementary to previously integrated exogenous nucleotides. In some embodiments, a plurality of exogenous nucleic acids may be integrated at one NANOS locus, such as in gene stacking.

Integration of a nucleic acid at a NANOS locus may be facilitated (e.g., catalyzed) in some embodiments by endogenous cellular machinery of a host cell, such as, for example and without limitation, endogenous DNA and endogenous recombinase enzymes. In some embodiments, integration of a nucleic acid at a NANOS locus may be facilitated by one or more factors (e.g., polypeptides) that are provided to a host cell. For example, nuclease(s), recombinase(s), and/or ligase polypeptides may be provided (either independently or as part of a chimeric polypeptide) by contacting the polypeptides with the host cell, or by expressing the polypeptides within the host cell. Accordingly, in some examples, a nucleic acid comprising a nucleotide sequence encoding at least one nuclease, recombinase, and/or ligase polypeptide may be introduced into the host cell, either concurrently or sequentially with a nucleic acid to be integrated site-specifically at a NANOS locus, wherein the at least one nuclease, recombinase, and/or ligase polypeptide is expressed from the nucleotide sequence in the host cell.

DNA-Binding Polypeptides

In some embodiments, site-specific integration may be accomplished by utilizing factors that are capable of recognizing and binding to particular nucleotide sequences, for example, in the genome of a host organism. For instance, many proteins comprise polypeptide domains that are capable of recognizing and binding to DNA in a site-specific manner. A DNA sequence that is recognized by a DNA-binding polypeptide may be referred to as a "target" sequence. Polypeptide domains that are capable of recognizing and binding to DNA in a site-specific manner generally fold correctly and function independently to bind DNA in a site-specific manner, even when expressed in a polypeptide other than the protein from which the domain was originally isolated. Similarly, target sequences for recognition and binding by DNA-binding polypeptides are generally able to be recognized and bound by such polypeptides, even when present in large DNA structures (e.g., a chromosome), particularly when the site where the target sequence is located is one known to be accessible to soluble cellular proteins (e.g., a gene).

While DNA-binding polypeptides identified from proteins that exist in nature typically bind to a discrete nucleotide sequence or motif (e.g., a consensus recognition sequence), methods exist and are known in the art for modifying many such DNA-binding polypeptides to recognize a different nucleotide sequence or motif. DNA-binding polypeptides include, for example and without limitation: zinc finger DNA-binding domains; leucine zippers; UPA DNA-binding domains; GAL4; TAL; LexA; a Tet repressor; LacR; and a steroid hormone receptor.

In some examples, a DNA-binding polypeptide is a zinc finger. Individual zinc finger motifs can be designed to target and bind specifically to any of a large range of DNA sites. Canonical $Cys_2His_2$ (as well as non-canonical $Cys_3His$) zinc finger polypeptides bind DNA by inserting an .alpha.-helix into the major groove of the target DNA double helix. Recognition of DNA by a zinc finger is modular; each finger contacts primarily three consecutive base pairs in the target, and a few key residues in the polypeptide mediate recognition. By including multiple zinc finger DNA-binding domains in a targeting endonuclease, the DNA-binding specificity of the targeting endonuclease may be further increased (and hence the specificity of any gene regulatory effects conferred thereby may also be increased). See, e.g., Urnov et al. (2005) Nature 435:646-51. Thus, one or more zinc finger DNA-binding polypeptides may be engineered and utilized such that a targeting endonuclease introduced into a host cell interacts with a DNA sequence that is unique within the genome of the host cell.

Preferably, the zinc finger protein is non-naturally occurring in that it is engineered to bind to a target site of choice. See, for example, See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In some examples, a DNA-binding polypeptide is a DNA-binding domain from GAL4. GAL4 is a modular transactivator in *Saccharomyces cerevisiae*, but it also operates as a transactivator in many other organisms. See, e.g., Sadowski et al. (1988) Nature 335:563-4. In this regulatory system, the expression of genes encoding enzymes of the galactose metabolic pathway in *S. cerevisiae* is stringently regulated by the available carbon source. Johnston (1987) Microbiol. Rev. 51:458-76. Transcriptional control of these metabolic enzymes is mediated by the interaction between the positive regulatory protein, GAL4, and a 17 bp symmetrical DNA sequence to which GAL4 specifically binds (the UAS).

Native GAL4 consists of 881 amino acid residues, with a molecular weight of 99 kDa. GAL4 comprises functionally autonomous domains, the combined activities of which account for activity of GAL4 in vivo. Ma and Ptashne (1987) Cell 48:847-53); Brent and Ptashne (1985) Cell 43(3 Pt 2):729-36. The N-terminal 65 amino acids of GAL4 comprise the GAL4 DNA-binding domain. Keegan et al. (1986) Science 231:699-704; Johnston (1987) Nature 328: 353-5. Sequence-specific binding requires the presence of a divalent cation coordinated by 6 Cys residues present in the DNA binding domain. The coordinated cation-containing domain interacts with and recognizes a conserved CCG triplet at each end of the 17 bp UAS via direct contacts with the major groove of the DNA helix. Marmorstein et al. (1992) Nature 356:408-14. The DNA-binding function of the protein positions C-terminal transcriptional activating domains in the vicinity of the promoter, such that the activating domains can direct transcription.

Additional DNA-binding polypeptides that may be utilized in certain embodiments include, for example and without limitation, a binding sequence from a AVRBS3-inducible gene; a consensus binding sequence from a AVRBS3-inducible gene or synthetic binding sequence engineered therefrom (e.g., UPA DNA-binding domain); TAL; LexA (see, e.g., Brent & Ptashne (1985), supra); LacR (see, e.g., Labow et al. (1990) Mol. Cell. Biol. 10:3343-56; Baim et al. (1991) Proc. Natl. Acad. Sci. USA 88(12):5072-6); a steroid hormone receptor (Ellliston et al. (1990) J. Biol. Chem. 265:11517-121); the Tet repressor (U.S. Pat. No. 6,271,341) and a mutated Tet repressor that binds to a tet operator sequence in the presence, but not the absence, of tetracycline (Tc); the DNA-binding domain of NF-.kappa.B; and components of the regulatory system described in Wang et al. (1994) Proc. Natl. Acad. Sci. USA 91(17):8180-4, which utilizes a fusion of GAL4, a hormone receptor, and VP16.

In certain embodiments, the DNA-binding domain of one or more of the nucleases used in the methods and compositions described herein comprises a naturally occurring or engineered (non-naturally occurring) TAL effector DNA binding domain. See, e.g., U.S. Patent Publication No. 20110301073, incorporated by reference in its entirety herein.

In other embodiments, the nuclease comprises a CRISPR/Cas system. The CRISPR (clustered regularly interspaced short palindromic repeats) locus, which encodes RNA components of the system, and the Cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of Cas genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the foreign nucleic acid. Thus, in the bacterial cell, several Cas proteins are involved with the natural function of the CRISPR/Cas system and serve roles in functions such as insertion of the foreign DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In particular embodiments, a DNA-binding polypeptide specifically recognizes and binds to a target nucleotide sequence comprised within a genomic nucleic acid of a host organism. Any number of discrete instances of the target nucleotide sequence may be found in the host genome in some examples. The target nucleotide sequence may be rare within the genome of the organism (e.g., fewer than about 10, about 9, about 8, about 7, about 6, about 5, about 4, about 3, about 2, or about 1 copy(ies) of the target sequence may exist in the genome). For example, the target nucleotide sequence may be located at a unique site within the genome of the organism. Target nucleotide sequences may be, for example and without limitation, randomly dispersed throughout the genome with respect to one another; located in different linkage groups in the genome; located in the same linkage group; located on different chromosomes; located on the same chromosome; located in the genome at sites that are expressed under similar conditions in the organism (e.g., under the control of the same, or substantially functionally identical, regulatory factors); and located closely to one another in the genome (e.g., target sequences may be comprised within nucleic acids integrated as concatemers at genomic loci).

Targeting Endonucleases

In particular embodiments, a DNA-binding polypeptide that specifically recognizes and binds to a target nucleotide sequence may be comprised within a chimeric polypeptide, so as to confer specific binding to the target sequence upon the chimeric polypeptide. In examples, such a chimeric polypeptide may comprise, for example and without limitation, nuclease, recombinase, and/or ligase polypeptides, as these polypeptides are described above. Chimeric polypeptides comprising a DNA-binding polypeptide and a nuclease, recombinase, and/or ligase polypeptide may also comprise other functional polypeptide motifs and/or domains, such as for example and without limitation: a spacer sequence positioned between the functional polypeptides in the chimeric protein; a leader peptide; a peptide that targets the fusion protein to an organelle (e.g., the nucleus); polypeptides that are cleaved by a cellular enzyme; peptide tags (e.g., Myc, His, etc.); and other amino acid sequences that do not interfere with the function of the chimeric polypeptide.

Functional polypeptides (e.g., DNA-binding polypeptides and nuclease polypeptides) in a chimeric polypeptide may be operatively linked. In some embodiments, functional polypeptides of a chimeric polypeptide may be operatively linked by their expression from a single polynucleotide encoding at least the functional polypeptides ligated to each other in-frame, so as to create a chimeric gene encoding a chimeric protein. In alternative embodiments, the functional polypeptides of a chimeric polypeptide may be operatively linked by other means, such as by cross-linkage of independently expressed polypeptides.

In some embodiments, a DNA-binding polypeptide, or guide RNA that specifically recognizes and binds to a target nucleotide sequence may be comprised within a natural isolated protein (or mutant thereof), wherein the natural isolated protein or mutant thereof also comprises a nuclease polypeptide (and may also comprise a recombinase and/or ligase polypeptide). Examples of such isolated proteins include TALENs, recombinases (e.g., Cre, Hin, Tre, and FLP recombinase), RNA-guided CRISPR/Cas9, and meganucleases.

As used herein, the term "targeting endonuclease" refers to natural or engineered isolated proteins and mutants thereof that comprise a DNA-binding polypeptide or guide RNA and a nuclease polypeptide, as well as to chimeric polypeptides comprising a DNA-binding polypeptide or guide RNA and a nuclease. Any targeting endonuclease comprising a DNA-binding polypeptide or guide RNA that specifically recognizes and binds to a target nucleotide sequence comprised within a NANOS locus (e.g., either because the target sequence is comprised within the native sequence at the locus, or because the target sequence has been introduced into the locus, for example, by recombination) may be utilized in certain embodiments.

Some examples of chimeric polypeptides that may be useful in particular embodiments of the invention include, without limitation, combinations of the following polypeptides: zinc finger DNA-binding polypeptides; a FokI nuclease polypeptide; TALE domains; leucine zippers; transcription factor DNA-binding motifs; and DNA recognition and/or cleavage domains isolated from, for example and without limitation, a TALEN, a recombinase (e.g., Cre, Hin, RecA, Tre, and FLP recombinases), RNA-guided CRISPR/Cas9, a meganuclease; and others known to those in the art. Particular examples include a chimeric protein comprising a site-specific DNA binding polypeptide and a nuclease polypeptide. Chimeric polypeptides may be engineered by methods known to those of skill in the art to alter the recognition sequence of a DNA-binding polypeptide comprised within the chimeric polypeptide, so as to target the chimeric polypeptide to a particular nucleotide sequence of interest.

In certain embodiments, the chimeric polypeptide comprises a DNA-binding domain (e.g., zinc finger, TAL-effector domain, etc.) and a nuclease (cleavage) domain. The cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides, or nucleotide pairs, can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding, for example, such that one or more exogenous sequences (donors/trangsenes) are integrated at or near the binding (target) sites. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Patent Publication No. 20070134796, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Zinc Finger Nucleases

In specific embodiments, a chimeric polypeptide is a custom-designed zinc finger nuclease (ZFN) that may be designed to deliver a targeted site-specific double-strand DNA break into which an exogenous nucleic acid, or donor DNA, may be integrated (See co-owned US Patent publication 20100257638, incorporated by reference herein). ZFNs are chimeric polypeptides containing a non-specific cleavage domain from a restriction endonuclease (for example, FokI) and a zinc finger DNA-binding domain polypeptide. See, e.g., Huang et al. (1996) J. Protein Chem. 15:481-9; Kim et al. (1997a) Proc. Natl. Acad. Sci. USA 94:3616-20; Kim et al. (1996) Proc. Natl. Acad. Sci. USA 93:1156-60; Kim et al. (1994) Proc Natl. Acad. Sci. USA 91:883-7; Kim et al. (1997b) Proc. Natl. Acad. Sci. USA 94:12875-9; Kim et al. (1997c) Gene 203:43-9; Kim et al. (1998) Biol. Chem. 379:489-95; Nahon and Raveh (1998) Nucleic Acids Res. 26:1233-9; Smith et al. (1999) Nucleic Acids Res. 27:674-81. In some embodiments, the ZFNs comprise non-canonical zinc finger DNA binding domains (see co-owned US Patent publication 20080182332, incorporated by reference herein). The FokI restriction endonuclease must dimerize via the nuclease domain in order to cleave DNA and introduce a double-strand break. Consequently, ZFNs containing a nuclease domain from such an endonuclease also require dimerization of the nuclease domain in order to cleave target DNA. Mani et al. (2005) Biochem. Biophys. Res. Commun. 334:1191-7; Smith et al. (2000) Nucleic Acids Res. 28:3361-9. Dimerization of the ZFN can be facilitated by two adjacent, oppositely oriented DNA-binding sites. Id.

In particular examples, a method for the site-specific integration of an exogenous nucleic acid into at least one NANOS locus of a host comprises introducing into a cell of the host a ZFN, wherein the ZFN recognizes and binds to a target nucleotide sequence, wherein the target nucleotide sequence is comprised within at least one NANOS locus of the host. In certain examples, the target nucleotide sequence is not comprised within the genome of the host at any other position than the at least one NANOS locus. For example, a DNA-binding polypeptide of the ZFN may be engineered to recognize and bind to a target nucleotide sequence identified within the at least one NANOS locus (e.g., by sequencing the NANOS locus). A method for the site-specific integration of an exogenous nucleic acid into at least one NANOS performance locus of a host that comprises introducing into a cell of the host a ZFN may also comprise introducing into the cell an exogenous nucleic acid, wherein recombination of the exogenous nucleic acid into a nucleic acid of the host comprising the at least one NANOS locus is facilitated by site-specific recognition and binding of the ZFN to the target sequence (and subsequent cleavage of the nucleic acid comprising the NANOS locus).

Optional Exogenous Nucleic Acids for Integration at a NANOS Locus

Embodiments of the invention may include one or more nucleic acids selected from the group consisting of: an exogenous nucleic acid for site-specific integration in at least one NANOS locus, for example and without limitation, an ORF; a nucleic acid comprising a nucleotide sequence encoding a targeting endonuclease; and a vector comprising at least one of either or both of the foregoing. Thus, particular nucleic acids for use in some embodiments include nucleotide sequences encoding a polypeptide, structural nucleotide sequences, and/or DNA-binding polypeptide recognition and binding sites.

Optional Exogenous Nucleic Acid Molecules for Site-Specific Integration

As noted above, insertion of an exogenous sequence (also called a "donor sequence" or "donor" or "transgene") is provided, for example for expression of a polypeptide, correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See e.g., U.S. Patent Publication Nos. 20100047805, 20110281361, 20110207221 and U.S. application Ser. No. 13/889,162. If introduced in linear form, the ends of the donor sequence can be protected (e.g. from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLY)).

The donor is generally integrated so that its expression is driven by the endogenous promoter at the integration site, namely the promoter that drives expression of the endogenous gene into which the donor is integrated (e.g., NANOS). However, it will be apparent that the donor may comprise a promoter and/or enhancer, for example a constitutive promoter or an inducible or tissue specific promoter.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous nucleic acids that may be integrated in a site-specific manner into at least one NANOS locus, so as to modify the NANOS locus, in embodiments include, for example and without limitation, nucleic acids comprising a nucleotide sequence encoding a polypeptide of interest; nucleic acids comprising an agronomic gene; nucleic acids comprising a nucleotide sequence encoding an RNAi molecule; or nucleic acids that disrupt the NANOS gene.

In some embodiments, an exogenous nucleic acid is integrated at a NANOS locus, so as to modify the NANOS locus, wherein the nucleic acid comprises a nucleotide sequence encoding a polypeptide of interest, such that the nucleotide sequence is expressed in the host from the NANOS locus. In some examples, the polypeptide of interest (e.g., a foreign protein) is expressed from a nucleotide sequence encoding the polypeptide of interest in commercial quantities. In such examples, the polypeptide of interest may be extracted from the host cell, tissue, or biomass.

Nucleic Acid Molecules Comprising a Nucleotide Sequence Encoding a Targeting Endonuclease In some embodiments, a nucleotide sequence encoding a targeting endonuclease may be engineered by manipulation (e.g., ligation) of native nucleotide sequences encoding polypeptides comprised within the targeting endonuclease. For example, the nucleotide sequence of a gene encoding a protein comprising a DNA-binding polypeptide may be inspected to identify the nucleotide sequence of the gene that corresponds to the DNA-binding polypeptide, and that nucleotide sequence may be used as an element of a nucleotide sequence encoding a targeting endonuclease comprising the DNA-binding polypeptide. Alternatively, the amino acid sequence of a targeting endonuclease may be used to deduce a nucleotide sequence encoding the targeting endonuclease, for example, according to the degeneracy of the genetic code.

In exemplary nucleic acid molecules comprising a nucleotide sequence encoding a targeting endonuclease, the last codon of a first polynucleotide sequence encoding a nuclease polypeptide, and the first codon of a second polynucleotide sequence encoding a DNA-binding polypeptide, may be separated by any number of nucleotide triplets, e.g., without coding for an intron or a "STOP." Likewise, the last codon of a nucleotide sequence encoding a first polynucleotide sequence encoding a DNA-binding polypeptide, and the first codon of a second polynucleotide sequence encoding a nuclease polypeptide, may be separated by any number of nucleotide triplets. In these and further embodiments, the last codon of the last (i.e., most 3' in the nucleic acid sequence) of a first polynucleotide sequence encoding a nuclease polypeptide, and a second polynucleotide sequence encoding a DNA-binding polypeptide, may be fused in phase-register with the first codon of a further polynucleotide coding sequence directly contiguous thereto, or separated therefrom by no more than a short peptide sequence, such as that encoded by a synthetic nucleotide linker (e.g., a nucleotide linker that may have been used to achieve the fusion). Examples of such further polynucleotide sequences include, for example and without limitation, tags, targeting peptides, and enzymatic cleavage sites. Likewise, the first codon of the most 5' (in the nucleic acid sequence) of the first and second polynucleotide sequences may be fused in phase-register with the last codon of a further polynucleotide coding sequence directly contiguous thereto, or separated therefrom by no more than a short peptide sequence.

A sequence separating polynucleotide sequences encoding functional polypeptides in a targeting endonuclease (e.g., a DNA-binding polypeptide and a nuclease polypeptide) may, for example, consist of any sequence, such that the amino acid sequence encoded is not likely to significantly alter the translation of the targeting endonuclease. Due to the autonomous nature of known nuclease polypeptides and known DNA-binding polypeptides, intervening sequences will not in examples interfere with the respective functions of these structures.

Other Knockout Methods

Various other techniques known in the art can be used to inactivate genes to make knock-out animals and/or to introduce nucleic acid constructs into animals to produce founder animals and to make animal lines, in which the knockout or nucleic acid construct is integrated into the genome. Such techniques include, without limitation, pronuclear microinjection (U.S. Pat. No. 4,873,191), retrovirus mediated gene transfer into germ lines (Van der Putten et al. (1985) Proc. Natl. Acad. Sci. USA 82, 6148-1652), gene targeting into embryonic stem cells (Thompson et al. (1989) Cell 56, 313-321), electroporation of embryos (Lo (1983) Mol. Cell. Biol. 3, 1803-1814), sperm-mediated gene transfer (Lavitrano et al. (2002) Proc. Natl. Acad. Sci. USA 99, 14230-14235; Lavitrano et al. (2006) Reprod. Fert. Develop. 18, 19-23), and in vitro transformation of somatic cells, such as cumulus or mammary cells, or adult, fetal, or embryonic stem cells, followed by nuclear transplantation (Wilmut et al. (1997) Nature 385, 810-813; and Wakayama et al. (1998) Nature 394, 369-374). Pronuclear microinjection, sperm mediated gene transfer, and somatic cell nuclear transfer are particularly useful techniques. An animal that is genomically modified is an animal wherein all of its cells have the genetic modification, including its germ line cells. When methods are used that produce an animal that is mosaic in its genetic modification, the animals may be inbred and progeny that are genomically modified may be selected. Cloning, for instance, may be used to make a mosaic animal if its cells are modified at the blastocyst state, or genomic modification can take place when a single-cell is modified. Animals that are modified so they do not sexually mature can be homozygous or heterozygous for the modification, depending on the specific approach that is used. If a particular gene is inactivated by a knock out modification, homozygousity would normally be required. If a particular gene is inactivated by an RNA interference or dominant negative strategy, then heterozygosity is often adequate.

Typically, in embryo/zygote microinjection, a nucleic acid construct or mRNA is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATURATION MEDIUM (Minitube, Verona, Wis.) supplemented with 0.1 mg/mL cysteine, 10 ng/mL epidermal growth factor, 10% porcine follicular fluid, 50.mu.M 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium, which will not contain cAMP, PMSG or hCG and incubated for an additional 22 hours. Matured oocytes can be stripped of their cumulus cells by vortexing in 0.1% hyaluronidase for 1 minute.

For swine, mature oocytes can be fertilized in 500 μl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to 4×10×5 sperm. Sperm concentrations can be analyzed by computer assisted semen analysis (SPERMVISION, Minitube, Verona, Wis.). Final in vitro insemination can be performed in a 10.mu.l volume at a final concentration of approximately 40 motile sperm/oocyte, depending on boar. Incubate all fertilizing oocytes at 38.7°

C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs or mRNA can be injected into one of the pronuclei or into the cytoplasm. Then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with using an Eppendorf FEMTOJET injector and can be cultured until blastocyst formation. Rates of embryo cleavage and blastocyst formation and quality can be recorded.

Embryos can be surgically transferred into uteri of asynchronous recipients. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed.

In somatic cell nuclear transfer, a transgenic cell (e.g., a transgenic pig cell or bovine cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis-2 are termed eggs. After producing a porcine or bovine embryo (e.g., by fusing and activating the oocyte), the embryo is transferred to the oviducts of a recipient female, about 20 to 24 hours after activation. See, for example, Cibelli et al. (1998) Science 280, 1256-1258 and U.S. Pat. No. 6,548,741. For pigs, recipient females can be checked for pregnancy approximately 20-21 days after transfer of the embryos.

Standard breeding techniques can be used to create animals that are homozygous for the exogenous nucleic acid from the initial heterozygous founder animals. Homozygosity may not be required, however. Transgenic pigs described herein can be bred with other pigs of interest.

In some embodiments, a nucleic acid of interest and a selectable marker can be provided on separate transposons and provided to either embryos or cells in unequal amount, where the amount of transposon containing the selectable marker far exceeds (5-10 fold excess) the transposon containing the nucleic acid of interest. Transgenic cells or animals expressing the nucleic acid of interest can be isolated based on presence and expression of the selectable marker. Because the transposons will integrate into the genome in a precise and unlinked way (independent transposition events), the nucleic acid of interest and the selectable marker are not genetically linked and can easily be separated by genetic segregation through standard breeding. Thus, transgenic animals can be produced that are not constrained to retain selectable markers in subsequent generations, an issue of some concern from a public safety perspective.

Once transgenic animal have been generated, expression of an exogenous nucleic acid can be assessed using standard techniques. Initial screening can be accomplished by Southern blot analysis to determine whether or not integration of the construct has taken place. For a description of Southern analysis, see sections 9.37-9.52 of Sambrook et al., 1989, Molecular Cloning, A Laboratory Manual, second edition, Cold Spring Harbor Press, Plainview; N.Y. Polymerase chain reaction (PCR) techniques also can be used in the initial screening PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example PCR Primer: A Laboratory Manual, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) Genetic Engineering News 12, 1; Guatelli et al. (1990) Proc. Natl. Acad. Sci. USA 87:1874; and Weiss (1991) Science 254:1292. At the blastocyst stage, embryos can be individually processed for analysis by PCR, Southern hybridization and splinkerette PCR (see, e.g., Dupuy et al. Proc Natl Acad Sci USA (2002) 99:4495).

Expression of a nucleic acid sequence encoding a polypeptide in the tissues of transgenic pigs can be assessed using techniques that include, for example, Northern blot analysis of tissue samples obtained from the animal, in situ hybridization analysis, Western analysis, immunoassays such as enzyme-linked immunosorbent assays, and reverse-transcriptase PCR (RT-PCR).

Interfering RNAs

A variety of interfering RNA (RNAi) systems are known. Double-stranded RNA (dsRNA) induces sequence-specific degradation of homologous gene transcripts. RNA-induced silencing complex (RISC) metabolizes dsRNA to small 21-23-nucleotide small interfering RNAs (siRNAs). RISC contains a double stranded RNAse (dsRNase, e.g., Dicer) and ssRNase (e.g., Argonaut 2 or Ago2). RISC utilizes antisense strand as a guide to find a cleavable target. Both siRNAs and microRNAs (miRNAs) are known. A method of inactivating a gene in a genetically edited animal comprises inducing RNA interference against a target gene and/or nucleic acid such that expression of the target gene and/or nucleic acid is reduced.

For example the exogenous nucleic acid sequence can induce RNA interference against a nucleic acid encoding a polypeptide. For example, double-stranded small interfering RNA (siRNA) or small hairpin RNA (shRNA) homologous to a target DNA can be used to reduce expression of that DNA. Constructs for siRNA can be produced as described, for example, in Fire et al. (1998) Nature 391:806; Romano and Masino (1992) Mol. Microbiol. 6:3343; Cogoni et al. (1996) EMBO J. 15:3153; Cogoni and Masino (1999) Nature 399:166; Misquitta and Paterson (1999) Proc. Natl. Acad. Sci. USA 96:1451; and Kennerdell and Carthew (1998) Cell 95:1017. Constructs for shRNA can be produced as described by McIntyre and Fanning (2006) BMC Biotechnology 6:1. In general, shRNAs are transcribed as a single-stranded RNA molecule containing complementary regions, which can anneal and form short hairpins.

The probability of finding a single, individual functional siRNA or miRNA directed to a specific gene is high. The predictability of a specific sequence of siRNA, for instance, is about 50% but a number of interfering RNAs may be made with good confidence that at least one of them will be effective.

Embodiments include an in vitro cell, an in vivo cell, and a genetically edited animal such as a livestock animal that express an RNAi directed against a neuroendocrine gene selective for sexual maturation. An embodiment is an RNAi directed against a gene in the group consisting of Gpr54, Kiss1, and GnRH1. The RNAi may be, for instance, selected from the group consisting of siRNA, shRNA, dsRNA, RISC and miRNA.

Inducible Systems

An inducible system may be used to control expression of a sexual maturation gene. Various inducible systems are known that allow spatiotemporal control of expression of a gene. Several have been proven to be functional in vivo in transgenic animals.

An example of an inducible system is the tetracycline (tet)-on promoter system, which can be used to regulate transcription of the nucleic acid. In this system, a mutated Tet repressor (TetR) is fused to the activation domain of herpes simplex virus VP 16 transactivator protein to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

The tetracycline-inducible system and the Cre/loxP recombinase system (either constitutive or inducible) are among the more commonly used inducible systems. The tetracycline-inducible system involves a tetracycline-controlled transactivator (tTA)/reverse tTA (rtTA). A method to use these systems in vivo involves generating two lines of genetically edited animals. One animal line expresses the activator (tTA, rtTA, or Cre recombinase) under the control of a selected promoter. Another set of transgenic animals express the acceptor, in which the expression of the gene of interest (or the gene to be modified) is under the control of the target sequence for the tTA/rtTA transactivators (or is flanked by loxP sequences). Mating the two strains of mice provides control of gene expression.

The tetracycline-dependent regulatory systems (tet systems) rely on two components, i.e., a tetracycline-controlled transactivator (tTA or rtTA) and a tTA/rtTA-dependent promoter that controls expression of a downstream cDNA, in a tetracycline-dependent manner. In the absence of tetracycline or its derivatives (such as doxycycline), tTA binds to tetO sequences, allowing transcriptional activation of the tTA-dependent promoter. However, in the presence of doxycycline, tTA cannot interact with its target and transcription does not occur. The tet system that uses tTA is termed tet-OFF, because tetracycline or doxycycline allows transcriptional down-regulation. Administration of tetracycline or its derivatives allows temporal control of transgene expression in vivo. rtTA is a variant of tTA that is not functional in the absence of doxycycline but requires the presence of the ligand for transactivation. This tet system is therefore termed tet-ON. The tet systems have been used in vivo for the inducible expression of several transgenes, encoding, e.g., reporter genes, oncogenes, or proteins involved in a signaling cascade.

The Cre/lox system uses the Cre recombinase, which catalyzes site-specific recombination by crossover between two distant Cre recognition sequences, i.e., loxP sites. A DNA sequence introduced between the two loxP sequences (termed foxed DNA) is excised by Cre-mediated recombination. Control of Cre expression in a transgenic animal, using either spatial control (with a tissue- or cell-specific promoter), or temporal control (with an inducible system), results in control of DNA excision between the two loxP sites. One application is for conditional gene inactivation (conditional knockout). Another approach is for protein over-expression, wherein a foxed stop codon is inserted between the promoter sequence and the DNA of interest. Genetically edited animals do not express the transgene until Cre is expressed, leading to excision of the floxed stop codon. This system has been applied to tissue-specific oncogenesis and controlled antigene receptor expression in B lymphocytes. Inducible Cre recombinases have also been developed. The inducible Cre recombinase is activated only by administration of an exogenous ligand. The inducible Cre recombinases are fusion proteins containing the original Cre recombinase and a specific ligand-binding domain. The functional activity of the Cre recombinase is dependent on an external ligand that is able to bind to this specific domain in the fusion protein.

Embodiments include an in vitro cell, an in vivo cell, and a genetically edited animal such as a livestock animal that comprise a neuroendocrine gene selective for sexual maturation that is under control of an inducible system. The genetic modification of an animal may be genomic or mosaic. An embodiment is a gene in the group consisting of Gpr54, Kiss1, and GnRH1 that is under control of an inducible system. The inducible system may be, for instance, selected from the group consisting of Tet-On, Tet-Off, Cre-lox, and Hif1 alpha.

Vectors and Nucleic Acids

A variety of nucleic acids may be introduced into cells for knockout purposes, for inactivation of a gene, to obtain expression of a gene, or for other purposes. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. In other embodiments, a promoter that facilitates the expression of a nucleic acid molecule without significant tissue or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al. (2001) Hum. Gene Ther. 12:563; and Kiwaki et al. (1996) Hum. Gene Ther. 7:821.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34-bp recognition sites recognized by the Cre recombinase) or FRT recognition sites such that the selectable marker can be excised from the construct. See, Orban, et al., Proc. Natl. Acad. Sci. (1992) 89:6861, for a review of Cre/lox technology, and Brand and Dymecki, Dev. Cell (2004) 6:7. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the exogenous nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™tag (Kodak, New Haven, Conn.).

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37.degree. C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult animal cells of any type, including, for example, germ cells such as an oocyte or an egg, a progenitor cell, an adult or embryonic stem cell, a primordial germ cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to an exogenous nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) Nucleic Acids Res. 31:6873); Tol2 (Kawakami (2007) Genome Biology 8 (Suppl. 1):57; Minos (Pavlopoulos et al. (2007) Genome Biology 8 (Suppl. 1):S2); Hsmar1 (Miskey et al. (2007)) Mol Cell Biol. 27:4589); and Passport have been developed to introduce nucleic acids into cells, including mice, human, and pig cells. The Sleeping Beauty transposon is particularly useful. A transposase can be delivered as a protein, encoded on the same nucleic acid construct as the exogenous nucleic acid, can be introduced on a separate nucleic acid construct, or provided as an mRNA (e.g., an in vitro-transcribed and capped mRNA).

Insulator elements also can be included in a nucleic acid construct to maintain expression of the exogenous nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region-(MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). The term transgenic is used broadly herein and refers to a genetically edited organism or genetically engineered organism whose genetic material has been altered using genetic engineering techniques. A knockout animal is thus transgenic regardless of whether or not exogenous genes or nucleic acids are expressed in the animal or its progeny.

Founder Animals, Animal Lines, Traits, and Reproduction

Founder animals may be produced by cloning and other methods described herein. The founders can be homozygous for a genetic modification, as in the case where a zygote or a primary cell undergoes a homozygous modification. Similarly, founders can also be made that are heterozygous. In the case of NANOs knockouts, the founders are preferably heterozygous. The founders may be genomically modified, meaning that all of the cells in their genome have undergone modification. Founders can be mosaic for a modification, as may happen when vectors are introduced into one of a plurality of cells in an embryo, typically at a blastocyst stage. Progeny of mosaic animals may be tested to identify progeny that are genomically modified. An animal line is established when a pool of animals has been created that can be reproduced sexually or by assisted reproductive techniques, with heterogeneous or homozygous progeny consistently expressing the modification.

In livestock, many alleles are known to be linked to various traits such as production traits, type traits, workability traits, and other functional traits. Artisans are accustomed to monitoring and quantifying these traits, e.g., Visscher et al., Livestock Production Science, 40 (1994) 123-137, U.S. Pat. No. 7,709,206, US 2001/0016315, US 2011/0023140, and US 2005/0153317. An animal line may include a trait chosen from a trait in the group consisting of a production trait, a type trait, a workability trait, a fertility trait, a mothering trait, and a disease resistance trait. Further traits include expression of a recombinant gene product.

Animals with a desired trait or traits may be modified to prevent their sexual maturation. Since the animals are sterile until matured, it is possible to regulate sexual maturity as a means of controlling dissemination of the animals. Animals that have been bred or modified to have one or more traits can thus be provided to recipients with a reduced risk that the recipients will breed the animals and appropriate the value of the traits to themselves. Embodiments of the invention include genetically modifying a genome of an animal with the modification comprising an inactivated sexual maturation gene, wherein the sexual maturation gene in a wild type animal expresses a factor selective for sexual maturation. Embodiments include treating the animal by administering a compound to remedy a deficiency caused by the loss of expression of the gene to induce sexual maturation in the animal.

Breeding of animals that require administration of a compound to induce sexual maturity may advantageously be accomplished at a treatment facility. The treatment facility can implement standardized protocols on well-controlled stock to efficiently produce consistent animals. The animal progeny may be distributed to a plurality of locations to be raised. Farms and farmers (a term including a ranch and ranchers) may thus order a desired number of progeny with a specified range of ages and/or weights and/or traits and have them delivered at a desired time and/or location. The recipients, e.g., farmers, may then raise the animals and deliver them to market as they desire.

Embodiments include delivering (e.g., to one or more locations, to a plurality of farms) a genetically edited livestock animal having an inactivated neuroendocrine gene selective for sexual maturation. Embodiments include delivery of animals having an age of between about 1 day and about 180 days. The animal may have one or more traits (for example one that expresses a desired trait or a high-value trait or a novel trait or a recombinant trait). Embodiments further include providing said animal and/or breeding said animal.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

Example 1

Design, Construction and Testing of Porcine NANOS2 TALEN Reagents

Figure 1:
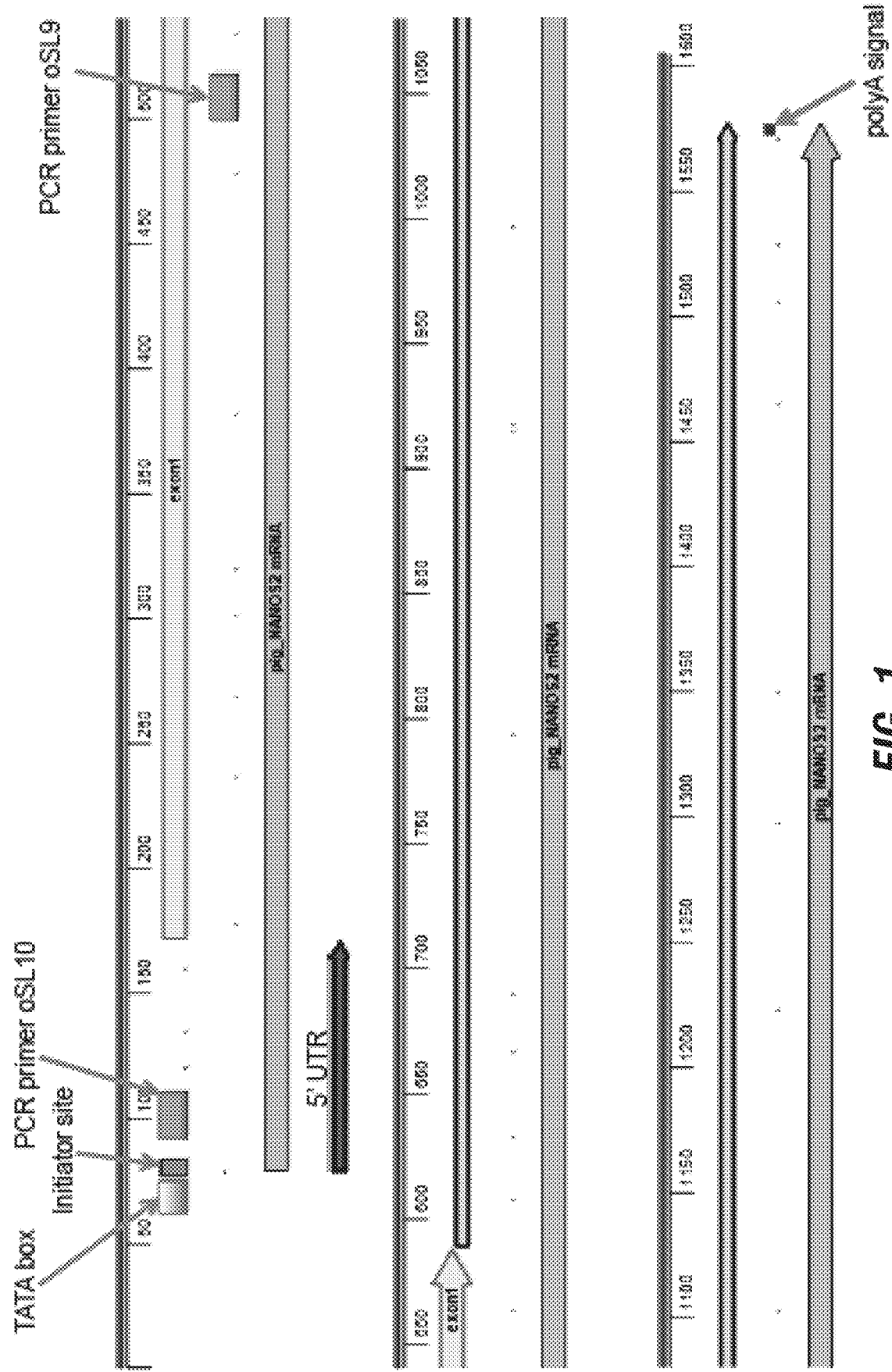
FIG. 1 is a composite of a multiple sequence alignment of porcine genomes to identify potential single nucleotide polymorphisms within the porcine NANOS2 gene (denoted by red dots) that could be used informatively in the design of genome editing reagents.

Porcine NANOS2 is located on chromosome 6, and constitutes a single exon encoding a protein of 138 amino acids. Multiple sequence alignment across independent pig sequences was carried out to identify potential single nucleotide polymorphisms (denoted by red dots FIG. 1), and where possible these were avoided during selection of TALEN binding sites. Potential sites for binding of porcine NANOS2 TALENs were identified close to the 5' end of the gene utilising the tool freely available at www.zifit.partners.org. Three TALEN pairs were constructed using the Golden Gate TALEN assembly protocol (Cermak et al, NAR 2011 39(12):e82). The right TALEN assembly was cloned into destination vector pCAG-T7-TALEN (Sangamo)-FokI-KKR-Destination and the left into pCAG-T7-TALEN (Sangamo)-FokI-ELD-Destination. A diagnostic restriction digest was carried out using enzymes BspeI and StuI/AatII, and positive clones were confirmed by DNA sequencing. Porcine NANOS2 TALENs

A SEQ ID NO: 75
TGCCATGCAGCTGCCACCCTTTGACATGTGGAAGGACTACTTCAACCTG

AGCCA
18:18:18

A Left:
SEQ ID NO: 76
5' TGCCATGCAG CTGCCACC

A Right:
SEQ ID NO: 77
5' TGGCTCAGGT TGAAGTAG

A Left
1) NG1-NN2-HD3-HD4-NI5-NG6-NN7-HD8-NI9-NN10-- pFUS_A

2) HD1-NG2-NN3-HD4-HD5-NI6-HD7--pFUS_B7

A Right
1) NG1-NN2-NN3-HD4-NG5-HD6-NI7-NN8-NN9-NG10-- pFUS_A

2) NG1-NN2-NI3-NI4-NN5-NG6-NI7--pFUS_B7

B SEQ ID NO: 78
TTTGACATGTGGAAGGACTACTTCAACCTGAGCCAGGTGGTGTTGGGAC

TGA
18:16:18

B Left:
SEQ ID NO: 79
5' TTTGACATGT GGAAGGAC

B Right:
SEQ ID NO: 80
5' TCAGTCCCAA CACCACCT

B Left
1) NG1-NG2-NG3-NN4-NI5-HD6-NI7-NG8-NN9-NG10--
   pFUS_A

2) NN1-NN2-NI3-NI4-NN5-NN6-NI7--pFUS_B7

B Right
1) NG1-HD2-NI3-NN4-NG5-HD6-HD7-HD8-NI9-NI10--
   pFUS_A

2) HD1-NI2-HD3-HD4-NI5-HD6-HD7--pFUS_B7

C SEQ ID NO: 81
TCAACCTGAGCCAGGTGGTGTTGGGACTGATCCAGAATCGTCGACAAGG

GCCA
18:17:18

C Left:
SEQ ID NO: 82
5' TCAACCTGAG CCAGGTGG

C Right:
SEQ ID NO: 83
5' TGGCCCTTGT CGACGATT

C Left
1) NG1-HD2-NI3-NI4-HD5-HD6-NG7-NN8-NI9-NN10- pFUS_A

2) HD1-HD2-NI3-NN4-NN5-NG6-NN7-pFUS_B7

C Right
1) NG1-NN2-NN3-HD4-HD5-HD6-NG7-NG8-NN9-NG10- pFUS_A

2) HD1-NN2-NI3-HD4-NN5-NI6-NG7-pFUS_B7

Porcine kidney PK15 cells were cultured in high glucose DMEM (Life Technologies, #31966) supplemented with 10% fetal bovine serum, 100 U/ml penicillin and 100 ug/ml streptomycin in a humidified incubator at 37° C. with 5% $CO_2$. One microgram of endotoxin-free maxiprep plasmid DNA encoding each half of TALEN pairs A, B or C, together with 1 ug of a plasmid encoding a CMV-driven eGFP were co-transfected into $6 \times 10^5$ PK15 cells using a Neon electroporator set at 2 pulses of 1400 mV for 20 ms each. Transfected cells were recovered in complete medium without antibiotic. Twenty four hours after transfection cells were transferred from 37° C. to a 30° C. incubator and maintained there for 48 hours. GFP+ve cells were isolated by fluorescence activated cell sorting, expanded by culturing and genomic DNA prepared using the Qiagen Dneasy Blood and Tissue kit. PCR was carried out on genomic DNA using Accuprime High Fidelity polymerase with PCR primers oSL9 and oSL10 oSL9
(SEQ ID NO: 84)
5' AGCGGGCAGTACTTGAGTGT oSL10
SEQ ID NO: 85)
5' CCAGAAAACCTTCTGCTGCT

Figure 2:
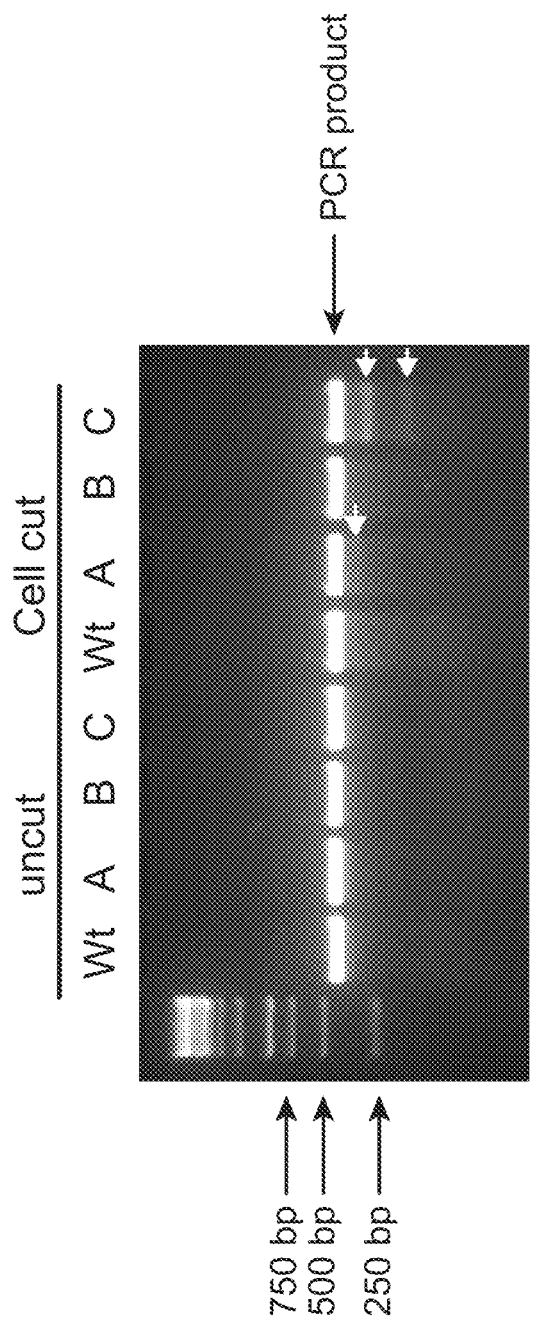
FIG. 2 shows the results of digested PCR products on agarose gel to identify NHEJ events. Genomic DNA was prepared from PK15 cells transfected with plasmids encoding TALEN pairs A, B or C then amplified with PCR primers oSL9 and oSL10. Mismatches were identified by digestion with the enzyme Cell.

Cell analysis was carried out on the PCR products as recommended by the manufacturer (Transgenomic). Digested PCR products were resolved on a 2% TAE agarose gel (FIG. 2). Surprisingly, there were substantial differences in the efficiency with which TALEN pairs were able to induce NHEJ events at their target sites. Low activity was noted for TALEN pair A (green arrow, FIG. 2), activity was not detectable for TALEN pair B, and was best for TALEN pair C (red arrows, FIG. 2).

Design, Construction and Testing of Porcine NANOS2 CRISPR Reagents

Potential small guide RNA target sites were initially identified based on the presence of protospacer adjacent motifs (PAM) within the coding sequence of the porcine NANOS2 gene (as determined by the presence of two consecutive guanine residues in either sense or antisense orientation within said coding sequence). Sites thus identified that spanned a potential SNP (as denoted by red dots in FIG. 1) were excluded from further analysis. Each of the remaining sites was analysed for potential off-target binding by using the BLAST algorithm (ncbi.nlm.nih.gov) to analyse the porcine genome for sequence matches. One sgRNA-binding site was selected that appeared to have high specificity for the NANOS2 gene within the porcine genome. This 20 base pair sequence fortuitously had a PAM sequence in each orientation

```
NANOS2 binding sites
                                    (SEQ ID NO: 86)
5' ccagaatcgtcgacaagggccagagg.3'

(SEQ ID NO: 87)
3' ggtcttagcagctgttcccggtctcc 5'
```

The underlined sequence is the binding site for the porcine NANOS2 guide sequences in both sense and antisense orientation (SEQ ID NOs 86 and 87). On the sense strand the PAM is denoted by the sequence agg 3' to the target site. On the antisense strand the PAM is denoted by the sequence tgg 3' to the target site.

Figure 3C:
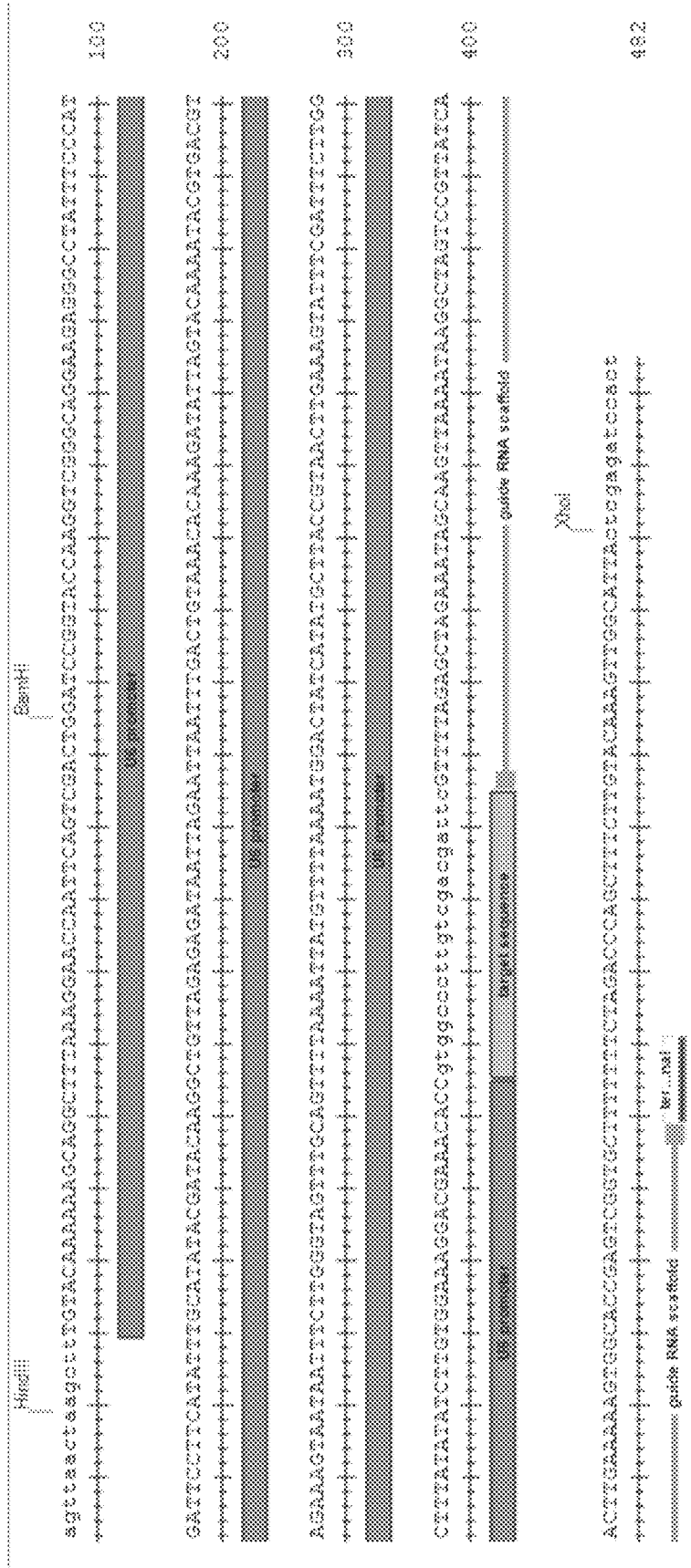
Figure 4:
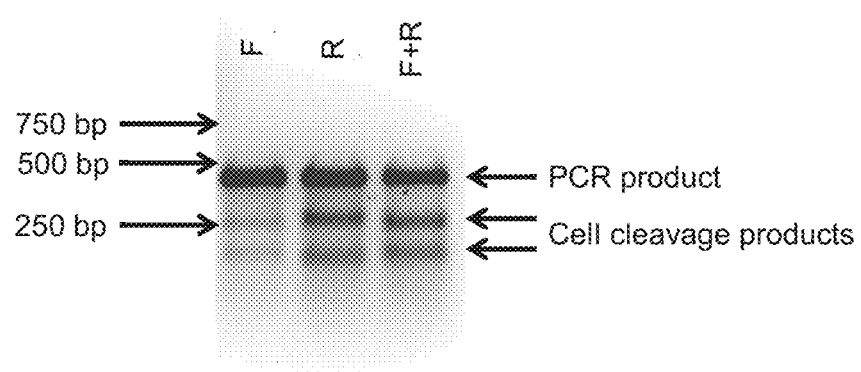
FIG. 4 shows the digested PCR products on agarose gel of Porcine CRISPR/Cas9 acting on DNA from PK15 cells. Three plasmids encoding the sgRNA sequence, a CAG-driven Cas9 and a CMV-driven eGFP respectively were co-transfected into PK15 cells. PCR was carried out on resultant genomic DNA with primers oSL9 and oSL10. Digested PCR products were resolved on a 2% TAE agarose gel. While both guide sequences resulted in cutting and NHEJ formation at the target site (indicated by the presence of Cell digestion products, red arrows), surprisingly it was discovered that the sgRNA sequence in reverse orientation with respect to the coding sequence was substantially more efficient than its sense counterpart.

The forward and reverse versions of the identified guide RNA binding sequence were designed and ordered as gBlocks (IDT) with the human U6 promoter driving expression of the sgRNA binding sequence, a guide RNA scaffold (also referred to as the Cas9 binding domain) and a terminator sequence (poly T) (FIGS. 3A and 3B). gBlock DNAs were cloned into a plasmid and endotoxin-free plasmid DNA prepared (Qiagen) (FIG. 3C). Three plasmids encoding the sgRNA sequence, a CAG-driven Cas9 and a CMV-driven eGFP respectively were co-transfected into 6×10⁵ PK15 cells using a Neon electroporator set at 2 pulses of 1400 mV for 20 ms each. Transfected cells were recovered in complete medium without antibiotic. Three days post transfection GFP positive cells were isolated by fluorescence activated cell sorting, expanded by culturing and genomic DNA prepared using the Qiagen DNeasy Blood and Tissue kit. PCR was carried out on this genomic DNA using Accuprime High Fidelity polymerase with PCR primers oSL9 and oSL10. Cell analysis was carried out on the PCR products as recommended by the manufacturer (Transgenomic). Digested PCR products were resolved on a 2% TAE agarose gel (FIG. 4). While both guide sequences resulted in cutting and NHEJ formation at the target site (indicated by the presence of Cell digestion products, red arrows, FIG. 4), surprisingly it was discovered that the sgRNA sequence in reverse orientation with respect to the coding sequence was substantially more efficient than its sense counterpart.

Example 2

Design, Construction and Testing of Bovine NANOS2 CRISPR Reagents

Potential target sites for sgRNAs were initially identified based on the presence of PAM sequences within either the coding sequence of the bovine NANOS2 gene or the sequence immediately flanking the coding sequence. Each potential site was analysed for potential off-target binding by using the BLAST algorithm (ncbi.nlm.nih.gov) to analyse the bovine genome for sequence matches. Nine potential sgRNA-binding sites were selected (three 5' to the coding sequence, three within the coding sequence, and three 3' to the stop codon) that appeared to have high specificity for the NANOS2 gene within the bovine genome.

For each identified sgRNA binding site, 2 guide sequences were designed; a 20-mer binding sequence, and a 19-, 18- or 17-mer binding sequence. See Table 1 and FIG. 12

TABLE 1

| oSL48 | caccggtctttgggaatataaaag | forward oligo for bovine NANOS2 5'guide 1 20-mer |
| oSL49 | aaaccttttatattcccaaagacc | reverse oligo for bovine NANOS2 5'guide 1 20-mer |
| oSL50 | caccgtctttgggaatataaaag | forward oligo for bovine NANOS2 5'guide 1 19-mer |
| oSL51 | aaaccttttatattcccaaagac | reverse oligo for bovine NANOS2 5'guide 1 19-mer |
| oSL52 | caccgctttgcttagaagggtcttt | forward oligo for bovine NANOS2 5'guide 2 20-mer |
| oSL53 | aaacaaagacccttctaagcaaagc | reverse oligo for bovine NANOS2 5'guide 2 20-mer |
| oSL54 | caccgttgcttagaagggtcttt | forward oligo for bovine NANOS2 5'guide 2 18-mer |
| oSL55 | aaacaaagacccttctaagcaac | reverse oligo for bovine NANOS2 5'guide 2 18-mer |
| oSL56 | caccgagctccacctttgcttagaa | forward oligo for bovine NANOS2 5'guide 3 20-mer |
| oSL57 | aaacttctaagcaaaggtggagctc | reverse oligo for bovine NANOS2 5'guide 3 20-mer |
| oSL58 | caccgctccacctttgcttagaa | forward oligo for bovine NANOS2 5'guide 3 19-mer |
| oSL59 | aaacttctaagcaaaggtggagc | reverse oligo for bovine NANOS2 5'guide 3 19-mer |
| oSL60 | caccggcaagggttggagacccaa | forward oligo for bovine NANOS2 internal guide 1 20-mer |
| oSL61 | aaacttgggtctccaacccttgcc | reverse oligo for bovine NANOS2 internal guide 1 20-mer |
| oSL62 | caccgcaagggttggagacccaa | forward oligo for bovine NANOS2 internal guide 1 19-mer |
| oSL63 | aaacttgggtctccaacccttgc | reverse oligo for bovine NANOS2 internal guide 1 19-mer |
| oSL64 | caccgccgagacccgggcccatg | forward oligo for bovine NANOS2 internal guide 2 20-mer |
| oSL65 | aaaccatggggcccgggtctcggc | reverse oligo for bovine NANOS2 internal guide 2 20-mer |

TABLE 1-continued

| | | |
|---|---|---|
| oSL66 | caccgagacccgggccccatg | forward oligo for bovine NANOS2 internal guide 2 17-mer |
| oSL67 | aaaccatggggcccgggtctc | reverse oligo for bovine NANOS2 internal guide 2 17-mer |
| oSL68 | caccgcccatgtggagcaggatcag | forward oligo for bovine NANOS2 internal guide 3 20-mer |
| oSL69 | aaacctgatcctgctccacatgggc | reverse oligo for bovine NANOS2 internal guide 3 20-mer |
| oSL70 | caccgcatgtggagcaggatcag | forward oligo for bovine NANOS2 internal guide 3 18-mer |
| oSL71 | aaacctgatcctgctccacatgc | reverse oligo for bovine NANOS2 internal guide 3 18-mer |
| oSL72 | caccgtccccatctctggactcgtc | forward oligo for bovine NANOS2 3'guide 1 20-mer |
| oSL73 | aaacgacgagtccagagatggggac | reverse oligo for bovine NANOS2 3'guide 1 20-mer |
| oSL74 | caccgcccatctctggactcgtc | forward oligo for bovine NANOS2 3'guide 1 18-mer |
| oSL75 | aaacgacgagtccagagatgggc | reverse oligo for bovine NANOS2 3'guide 1 18-mer |
| oSL76 | caccgtctggactcgtccggcectt | forward oligo for bovine NANOS2 3'guide 2 20-mer |
| oSL77 | aaacaagggccggacgagtccagac | reverse oligo for bovine NANOS2 3'guide 2 20-mer |
| oSL78 | caccggactcgtccggccctt | forward oligo for bovine NANOS2 3'guide 2 17-mer |
| oSL79 | aaacaagggccggacgagtcc | reverse oligo for bovine NANOS2 3'guide 2 17-mer |
| oSL80 | caccgtctcagtacttgatccctgc | forward oligo for bovine NANOS2 3'guide 3 20-mer |
| oSL81 | aaacgcagggatcaagtactgagac | reverse oligo for bovine NANOS2 3'guide 3 20-mer |
| oSL82 | caccgtcagtacttgatccctgc | forward oligo for bovine NANOS2 3'guide 3 18-mer |
| oSL83 | aaacgcagggatcaagtactgac | reverse oligo for bovine NANOS2 3'guide 3 18-mer |

Figure 5A:
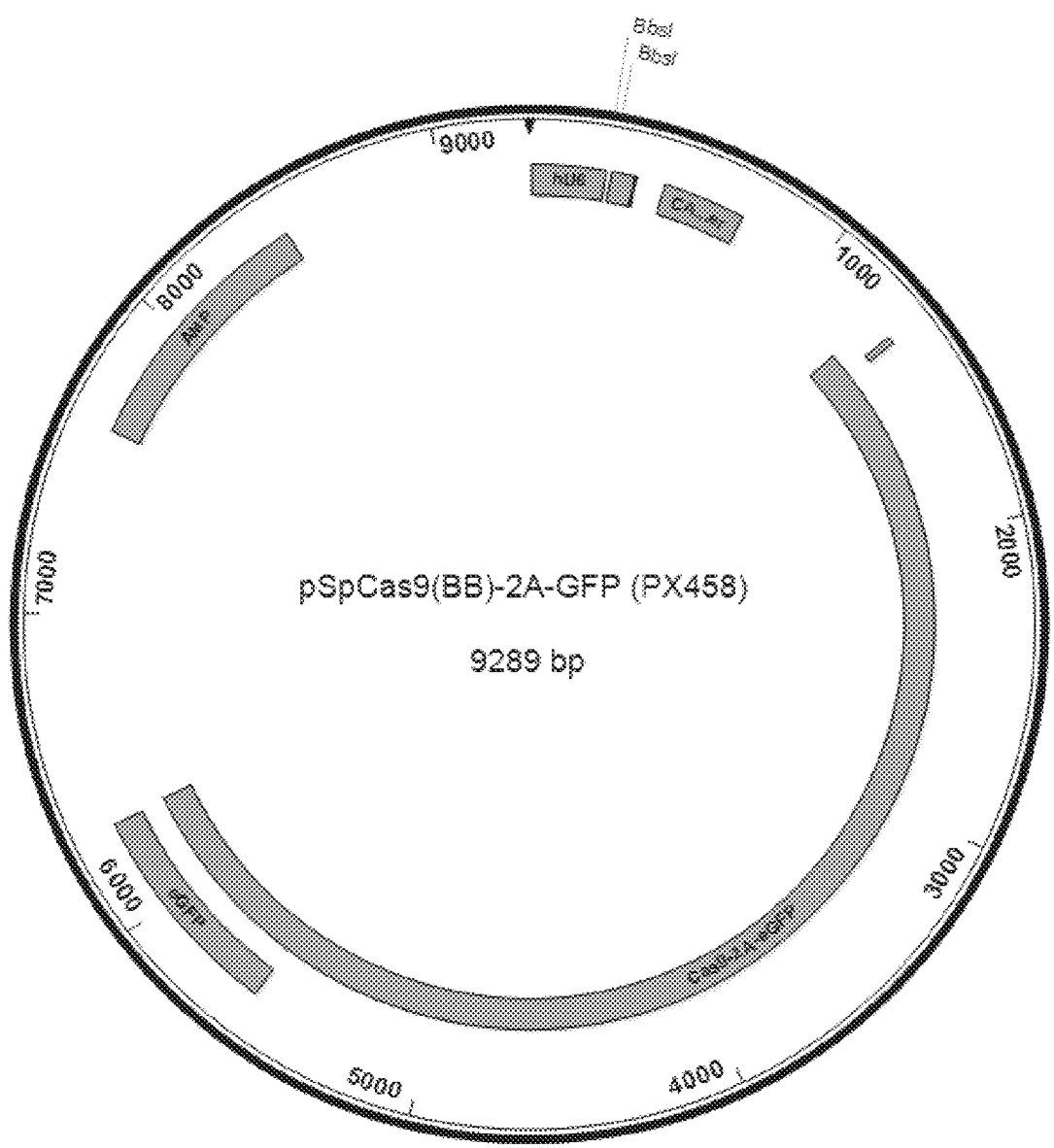
FIG. 5A is a map of the pSpCas9(BB)-2A-GFP (PX458) plasmid.
Figure 5B:
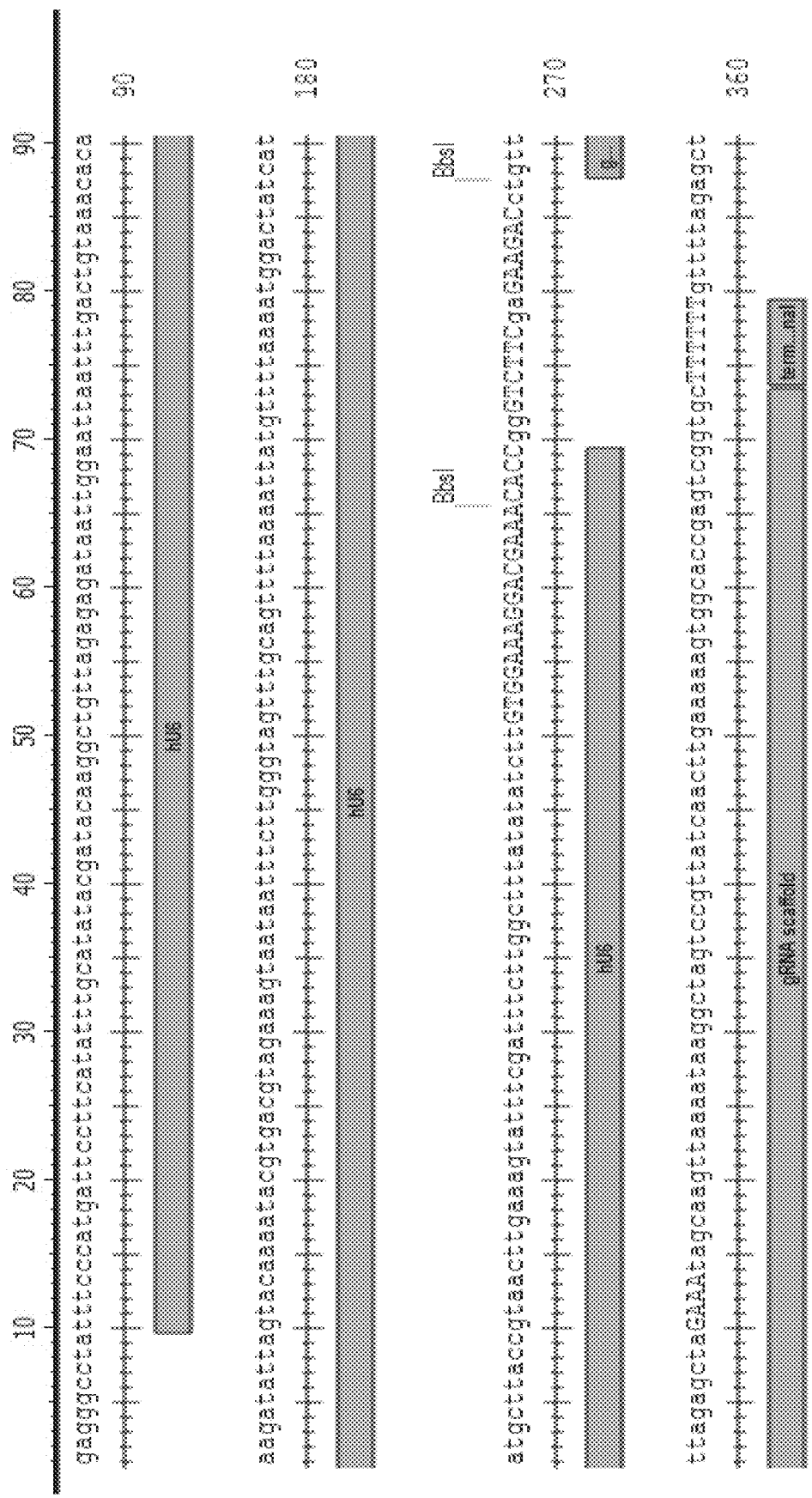
FIG. 5B shows the sequence annotations pX458 partial sequence (SEQ ID NO:22); hU6 sequence (SEQ ID NO:23), gRNA sequence (SEQ ID NO:24), terminal sequence (SEQ ID NO:25).
Figure 5C1:
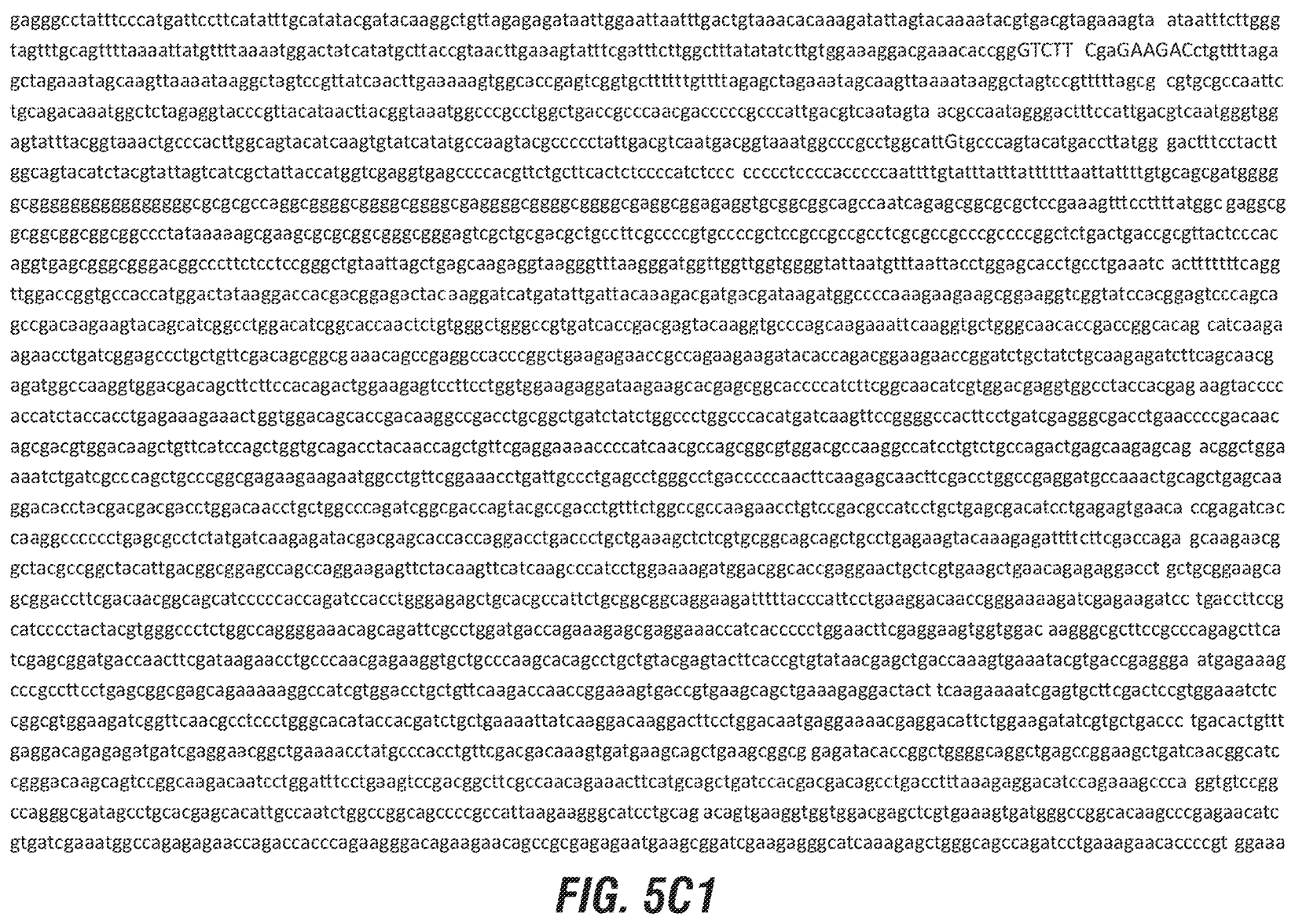

The guide RNA sequences were constructed as a pair of oligonucleotides which, once annealed, could be cloned into the BbsI sites of plasmid px458 (FIGS. 5A, 5B and 5C). This produced a single plasmid with a human U6-driven sgRNA sequence, followed by a CAG-driven Cas9 with a 2A-cleavable GFP. A list of plasmids is in Table 2, See FIG. 12.

TABLE 2

| | |
|---|---|
| pSL32 | oSL48/49 cloned into px458 |
| pSL33 | oSL50/51 cloned into px458 |
| pSL34 | oSL52/53 cloned into px458 |
| pSL35 | oSL54/55 cloned into px458 |
| pSL36 | oSL56/57 cloned into px458 |
| pSL37 | oSL58/59 cloned into px458 |
| pSL38 | oSL60/61 cloned into px458 |
| pSL39 | oSL64/65 cloned into px458 |
| pSL40 | oSL66/67 cloned into px458 |
| pSL41 | oSL68/69 cloned into px458 |
| pSL42 | oSL70/71 cloned into px458 |
| pSL43 | oSL72/73 cloned into px458 |
| pSL44 | oSL74/75 cloned into px458 |
| pSL45 | oSL76/77 cloned into px458 |
| pSL46 | oSL78/79 cloned into px458 |
| pSL47 | oSL80/81 cloned into px458 |
| pSL48 | oSL82/83 cloned into px458 |
| pSL49 | oSL62/63 cloned into px458 |

Figure 6A:
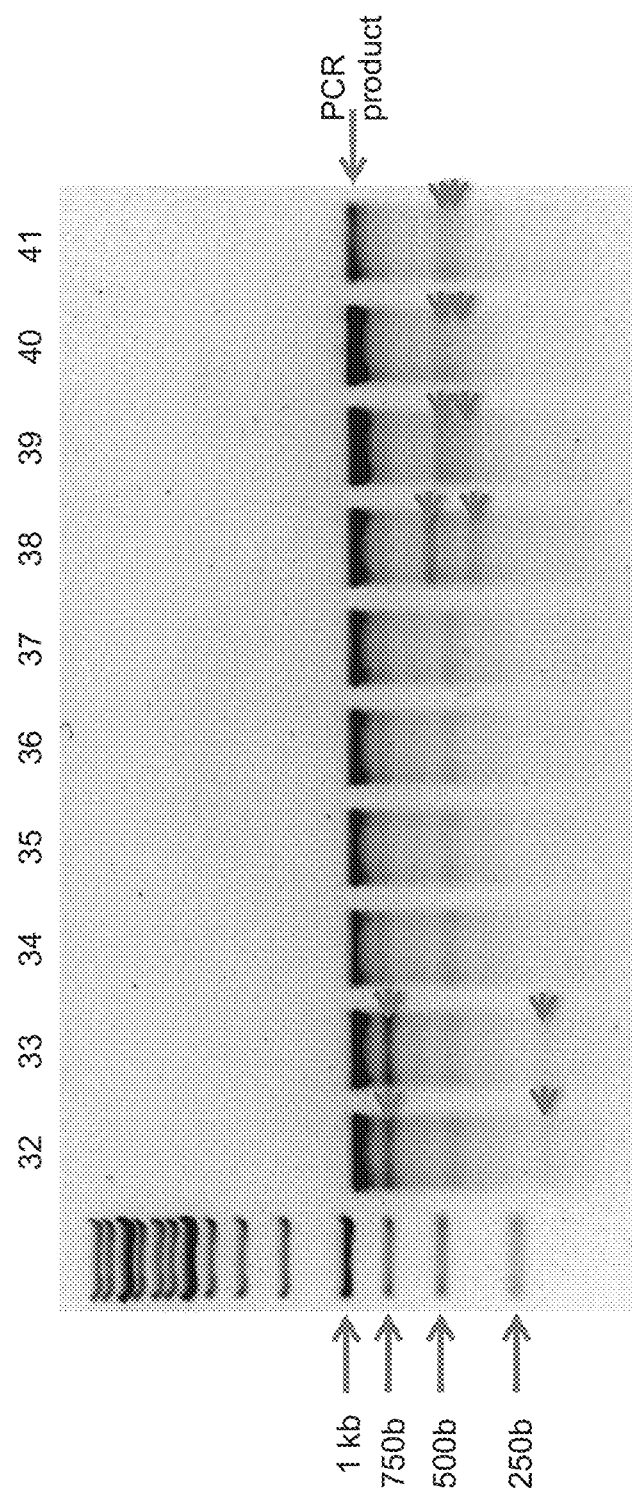
FIGS. 6A and 6B is a gel of PCR products from genomic DNA post transfection and showed substantial differences in the efficiencies with which sgRNAs were able to induce NHEJ formation at their target site as indicated by the presence of T7endonuclease digestion products (red arrows).
Figure 6B:
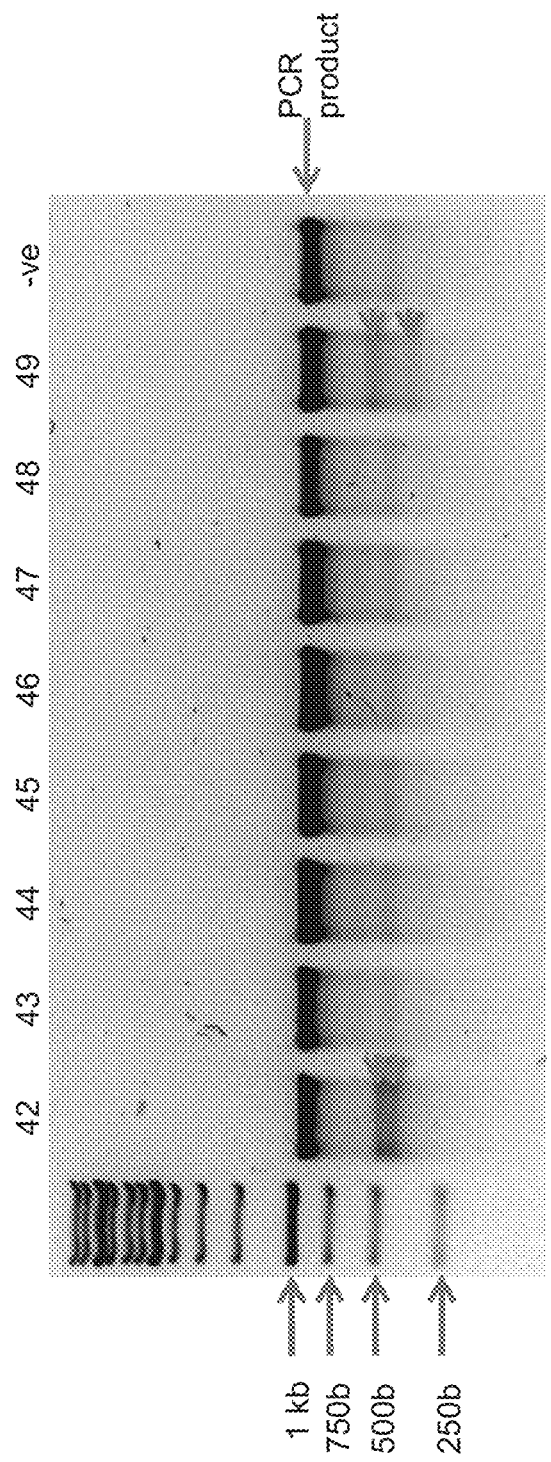

One microgram of plasmid miniprep DNA (Qiagen) was transfected into 6×10⁵ bovine embryonic fibroblast cells (BEF) using a Neon electroporator set at a single pulse of 1800 mV for 20 ms. Two days post transfection genomic DNA was prepared using the Qiagen DNeasy Blood and Tissue kit. PCR was carried out on this genomic DNA using Accuprime High Fidelity polymerase with PCR primers oSL86 and oSL87.

oSL86
(SEQ ID NO: 64)
agacgggtctttccagaggt oSL87
(SEQ ID NO: 74)
acaagagtccggagagctga T7 endonuclease analysis was carried out on purified PCR products as recommended by the manufacturer (NEB). Digested PCR products were resolved on a 1.4% TAE agarose gel (FIGS. 6A and 6B). Surprisingly there were substantial differences discovered in the efficiencies with which sgRNAs were able to induce NHEJ formation at their target sites (indicated by the presence of T7 endonuclease digestion products, red arrows FIGS. 6A and 6B).

Figure 7:
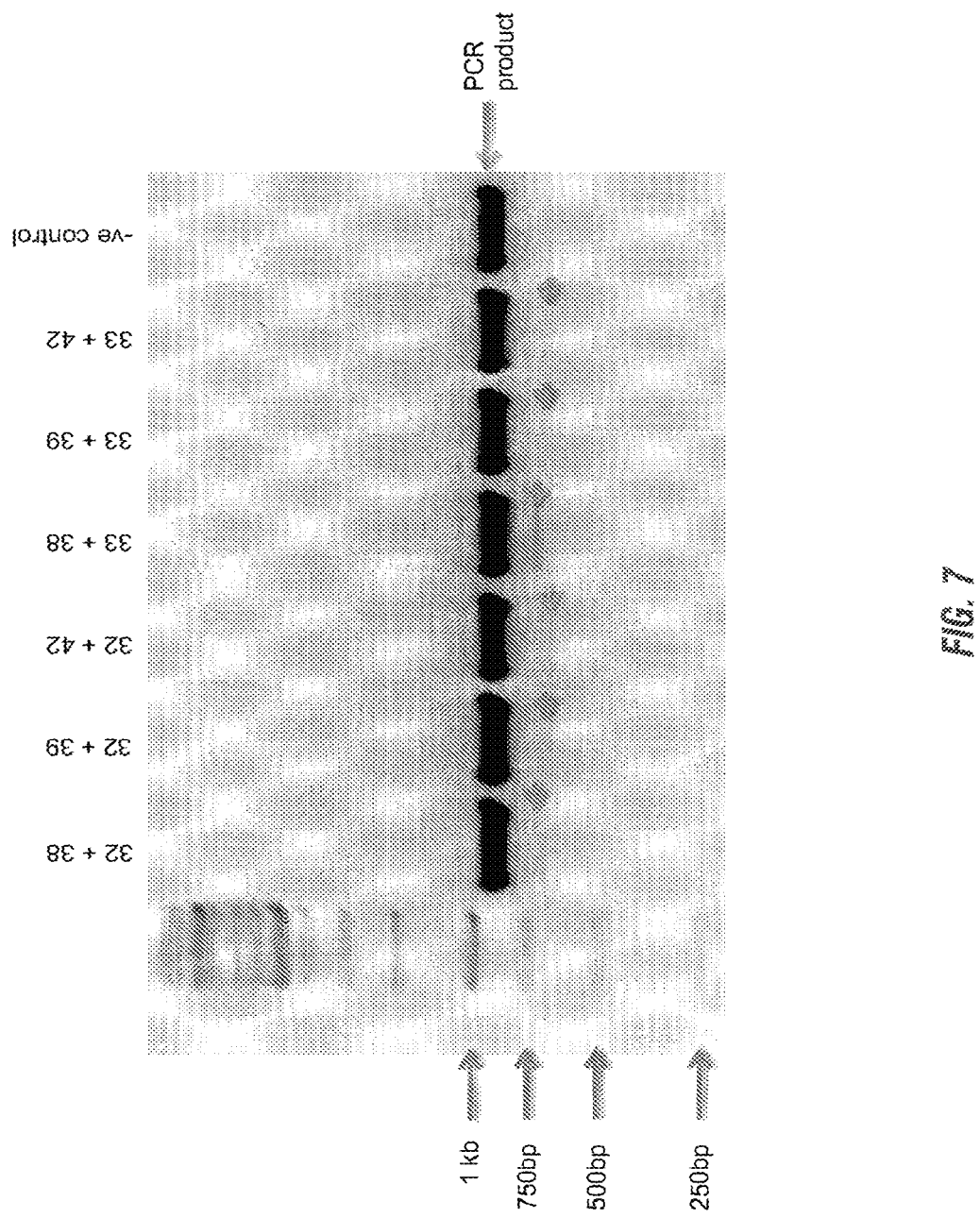
FIG. 7 is shows deletions generated by the use of different combinations of CRISPRs. Photo is a gel of genomic DNA if indels amplified with primers oSL86 (SEQ ID NO:64) and oSL87 (SEQ ID NO:74) of the six plasmid combinations.

Guide sequences with the highest activity as determined by T7 endonuclease assay for NHEJ were combined in pairs, such that cleavage at both target sites within a cell has the potential to cause a deletion of the intervening sequence. One microgram each of plasmids pSL32+pSL38, pSL32+pSL39, pSL32+pSL42, pSL33+pSL38, pSL33+pSL39 or pSL33+pSL42 was transfected into 6×10⁵ BEF cells. Transfection, culturing and DNA preparation from BEF cells was as above. PCR was carried out on genomic DNA using Accuprime High Fidelity polymerase with PCR primers oSL86 and oSL87 and products were resolved on a 1.4% TAE agarose gel (FIG. 7). All six plasmid combinations demonstrated that, in addition to the full length PCR product, transfected cell populations also harboured truncated NANOS2 gene fragments of a size specific to sgRNA sequence combination employed (red arrows, FIG. 7).

These truncated fragments were excised from the gel and DNA separated from the agarose by centrifuging the gel slice in a Spin-X Centrifuge Tube Filter (Costar #8163). The purified products were cloned into a pCR 4-TOPO vector using the TOPO TA Cloning Kit For Sequencing (Invitrogen #45-0030) and transformed into XL-1 Blue Competent Cells (Agilent Technologies #200249). Transformed bacteria were plated onto LB agar plates containing 100 ug/ml ampicillin and cultured at 37° C. overnight. Five colonies from each plate were selected and expanded overnight in LB medium containing 50 ug/ml ampicillin. Plasmid was isolated using a PureYield Plasmid Miniprep System (Promega #A1223) and sent for sequencing (Edinburgh Genomics) using primer oSL86. Alignment of the sequences demonstrates that deletion within the targeted sequence had occurred in each case (FIG. 8). Precise end joining between the ends of the deleted fragments was detected in at least one clone from each transfection, while other clones represented more imprecise events, indicating additional modification to the sequence occurred during the end-joining process. Clones sequenced from the pSL33+pSL38 combination all showed identical, precise end joining events.

This approach indicates that it is possible, and possibly desirable, to cause specific deletions in the target gene that result in loss or reduction of encoded protein expression or alteration of function of the resultant translated protein, as an additional strategy to the induction of NHEJ and consequent frame-shift mutations.

Example 3

The CRISPR/Cas System for Genetic Ablation

Following successful validation in cell culture as shown in FIG. 4, the guide sequence was assembled with a T7 promoter and synthesized as a G-block from IDT technologies. Assembly with a T7 driven construct is necessary for in vitro transcription and production of RNA. Briefly, sgRNA was transcribed using T7 in vitro transcription kit (Ambion). Likewise, the Cas9 plasmid was obtained from Addgene (Plasmid #42234; Name: pMJ920), and the Cas9 mRNA was transcribed using T7 Megascript in vitro transcription kit (FIG. 9A).

Both Cas9 mRNA (100 ng/µl), and sgRNA targeting NANOS2 (50 ng/µl) were injected into 1-cell porcine zygotes using an Eppendorf Femtojet injector on a continuous flow setting. The injected embryos were allowed to progress to blastocyst stage (FIG. 9C) for an additional 6 days, DNA collected, and PCR amplified around the target site. The presence of target gene deletions (as a consequence of NHEJ repair) was assessed by sequencing of the PCR amplicons. As shown in FIG. 9D, successful targeting of the NANOS2 locus was demonstrated. The sequence surrounding the CRISPR target site in NANOS2 was amplified using gene specific primers, cloned into PCR2.1 vector (Invitrogen), transformed into DH5a cells (NEB) and transformants selected based on Kanamycin resistance. The colonies were cultured overnight, miniprepped and the plasmids sequenced by Sanger sequencing. In FIG. 9, "N" represents NANOS2 allele, first digit is the blastocyst number, and the second hyphenated number represents the bacterial clone containing the amplified NANOS2. In the figure, representative sequences from clones are shown indicating deletions "–" around the predicted CRISPR cut site. Sequences from 8 different blastocysts showed successful deletion and disruption of the NANOS2 open reading frame, generating knockout alleles and are shown in FIG. 9D.

A second sgRNA sequence for NANOS2 was also selected. GAAGACACCGGAGGGCGTGGTGG (SEQ ID NO: 7). This target and the earlier target GAATCGTCGACAAGGGCCAGAGG (SEQ ID NO: 8), were co-injected together into one cell embryos and cultured to blastocyst DNA analysis of blastocysts demonstrated deletions and knockout of the NANOS2 alleles, see FIG. 10.

Use of Nickase Pairs for Gene Targeting

The Cas9 nuclease introduces double strand breaksinto DNA. By contrast, Cas9 nickase only cuts (or nicks) one of the two strands of DNA. When designed against targets in close proximity on opposite strands, paired nickases can introduce double strand breaks, and consequently can generate deletions with high precision. The advantage of using paired nickases vs nucleases is that even if the Cas9 nickase displays off-target binding, only one of the two strands will be nicked, which can be effectively repaired without causing unwanted modifications at the off targeting site. However, when used in combination in close proximity, the nickases introduce targeted DNA cleavage. A pair of nickases was designed to target the porcine NANOS2 gene. However, the nickases were not effective in introducing mutations (FIG. 11). A pair of single guide RNAs was designed to target on opposite strands. Both the sgRNAs are shown in the boxed section in FIG. 11, with the reverse strand highlighted in yellow. PAM motifs of both sgRNAs are highlighted in green. No modifications were identified around the target site.

Generation of NANOS2-Deficient Pig Models

The candidate CRISPR sgRNAs and Cas9:GFP mRNA were injected into in vitro fertilized porcine embryos (FIG. 9C). Briefly, maturing oocytes from sows were purchased from ART Inc. (Madison, WI) and shipped to the lab overnight in their commercial maturation medium #1. Twenty-four hours after being placed in the maturation medium #1 (provided by ART), 50 to 75 cumulus-oocyte complexes (COCs) were placed in 500 µl of tissue culture medium 199 (TCM 199) containing 0.14% PVA, 10 ng/ml epidermal growth factor, 0.57 mM cysteine, 0.5 IU/ml porcine FSH, and 0.5 IU/ml ovine LH and cultured for an additional 20 hours at 38.5° C. and 5% $CO_2$ in air, 100% humidity. COCs were vortexed in 0.1% hyaluronidase in HEPES-buffered medium containing 0.01% PVA for 4 minutes to remove the cumulus cells following maturation. Groups of 30-35 mature, denuded oocytes were placed in 100 µl of a modified Tris-buffered medium (mTBM) and fertilized according to an established protocol using fresh extended boar semen. Briefly, 1-2 ml of extended semen was mixed with Dulbecco's Phosphate Buffered Saline (DPBS) containing 1 mg/ml BSA to a final volume of 10 ml and centrifuged at 1000×g, 25° C. for four minutes; spermatozoa were washed in DPBS a total of three times. After the final wash, spermatozoa were resuspended in mTBM medium and added to oocytes at a final concentration of $5 \times 10^5$ spermatozoa/ml, and co-incubated for 5 hours at 38.5° C. and 5% $CO_2$. Five hours following fertilization, the presumptive zygotes were injected with Cas9 mRNA and sgRNA targeting NANOS2 and the intact embryos surgically transferred into the oviducts of synchronized female recipient animals by exposing the reproductive tract by midline incision. Animals were allowed to recover from surgery and housed at BARC-USDA facility.

Another alternative is to use in vivo fertilized 1-cell embryos for CRISPR mediated targeting of NANOS2 and generation of edited animals. Embryo donor animals are synchronized for estrus and superovulated by first feeding with Regumate (Alterenogest) for 14-16 days, followed by subcutaneous injections of PG600 (5 ml) on day 17 and 1000 IU of hCG on day 20. Animals are bred thrice, once on standing estrus (day 20), and two more inseminations 8 hours apart on day 21. Animals are humanely slaughtered on day 22 and the embryos harvested by flushing the oviduct. Embryos are injected with CRISPR mRNA and surgically transferred into synchronized recipient (or surrogate) animals the same day as described above.

Example 4

Screening and Breeding of Animals
Screening Animals

Liveborn animals following transfer of edited embryos will be genotyped as follows. Tissue samples (for example hair follicle, ear notches, tail clips, blood) will be taken and DNA extracted. The NANOS2 gene will be amplified using suitable primers and sequenced. Animals will be characterized as non-edited, heterozygous edited or homozygous edited.

Fertility of Homozygous NANOS2 Edited Females

Homozygous NANOS2 edited females will be monitored for puberty and the ability to ovulate fertile oocytes. Oocytes will be tested for the ability to produce blastocysts following in vitro fertilization. Example homozygous NANOS2 edited females will undergo hemiovariectomy and the ovary examined for normal oogenesis. The females will also be bred and the establishment of pregnancy monitored. Ultimately homozygous NANOS2 edited female fertility will be established by the production of live healthy offspring. We expect homozygous NANOS2 edited females to have normal fertility.

Testis Structure and Function of Heterozygous and Homozygous NANOS2 Edited Males Testis growth and dimensions will be monitored in heterozygous and homozygous NANOS2 edited males. We expect heterozygous males to have normal testis growth and dimensions, whereas homozygous males are expected to show reduced testis growth and small testes at puberty due to a lack of germ cells. Example heterozygous and homozygous NANOS2 edited males will undergo hemicastration and the testes examined cytologically. We expect heterozygous males to show normal testis structure with seminiferous tubules populated with Sertoli and germ cells, whereas homozygous males are expected to have a Sertoli cell-only morphology and the complete absence of germcells. Semen volume and composition will be examined following appropriate semen collection (for example artificial vagina, gloved hand, electroejaculation). We expect heterozygous males to have normal semen volumes and sperm counts, whereas homozygous males are expected to show the complete absence of sperm cells.

Transplantation of SSCs into the Testes of Homozygous NANOS2 Edited Males

SSCs will be harvested and propagated from appropriate donors, for example Duroc pigs, and SSCs injected into the rete testis of homozygous NANOS2 edited recipient males, for example Large White×Landrace crossbred pigs, at various ages. At puberty or at least three months after SSC transplantation, semen will be collected and examined for the presence of sperm cells. If sperm cells are present, we will determine sperm cell concentration, morphology and motility. We will also determine that the sperm cells present are from the donor SSCs and not from the recipient, for example showing the presence of Duroc specific SNPs in the MC1R gene for the pig example. We will determine the optimal recipient age of recipient pigs for maximum sperm cell production which should correlate with the efficiency of SSC colonization of the recipient testis.

Breeding for the Production of Homozygous NANOS2 Edited Males as SSC Recipients

A supply of homozygous NANOS2 edited males can be produced by breeding homozygous NANOS2 edited females with heterozygous edited males. The cross will produce equal numbers of homozygous and heterozygous edited males and females. Homozygous edited males will be used as SSC recipients, homozygous females and heterozygous males will be used as replacement breeding animals to produce further homozygous NANOS2 edited males as SSC recipients and heterozygous females will be culled.

Example 5

Generation of NANOS2 Edited Animals Via Embryo Injections

A candidate chimeric sgRNA targeting Exon-1 of porcine NANOS2 was designed based on the freely available software developed by Dr. Feng Zhang at MIT (crispr.mit.edu). The guide RNA used in the embryo injection studies is:

(SEQ ID NO: 160)
GATCAGTCCCAACACCACCTGG.

Both the CRISPR guide RNA sequence (SEQ ID NO:160) and the CRISPR target sequence (SEQ ID NO:161) within the NANOS2 ORF (SEQ ID NOS:1 and 2) are shown in FIG. 13.

The candidate CRISPR sgRNA alongside Cas9:GFP mRNA were in vitro transcribed using T7 mMessage Machine kit (Ambion), cleaned by Megaclear Kit (Ambion) and injected into in vivo fertilized porcine 1-cell embryos. A cohort of 12 animals of 8-9 months of age were synchronized for estrus and used in the experiment. Eight of the synchronized animals were bred to serve as embryo donors, whereas the remaining 4 animals were synchronized but not bred to serve as surrogates. Estrus was synchronized by feeding 5 ml of progesterone analog, Regumate (or Matrix) for 14 days. Twenty four hours (h) after last Regumate feeding, the animals were given a dose of PMSG (1200 IU, Sigma) subcutaneously, and the ovulation is induced 72 h later by administration of HCG (1000 IU, Chorulon, Merck) subcutaneously. The donor animals (n=8) in standing heat were artificially inseminated with boar semen (provided by PIC Genetics). In vivo embryos from donor animals were recovered surgically 24 h after AI by retrograde flushing with sterile PVA TL-Hepes medium from the oviduct. The in vivo derived embryos were then injected with Cas9:GFP mRNA and sgRNA targeting NANOS2, and cultured in PZM3 medium[58] overnight. A day after microinjection, 30 embryos were transferred surgically into the oviducts of each surrogate animal.

For embryo transfers, donor and surrogate pigs were anesthetized by a mix of ketamine/xylazine (6.6 mg/kg and 1-2 mg/kg IM) and placed on the back on a surgical table. Adequate depth of anesthesia was assessed by monitoring heart rate, temperature, full rhythmic respirations, constricted pupil, and reduced or absent palpebral reflex. The reproductive tract of anesthetized gilts were exposed via a midline abdominal incision. Only the oviducts and tips of the uterus were exposed. In donors, embryos were retrograde flushed through the utero-tubal junction, and the embryos collected from ostium of oviduct. For embryo transfer into surrogates, a tom-cat catheter containing the embryos was placed through the infundibulum and the embryos deposited into the oviduct. Following three-layered closure of the incision using absorbable sutures (USP #3 body wall, #3 fat, #1 sub-q), the animals were allowed to recover. Pregnancies were confirmed by lack of return to Estrus (21 days) and ultrasound at 28 days post embryo transfer. Our first embryo transfer trial has resulted in 3 out of 4 surrogate animals establishing pregnancy, and the birth of 18 edited piglets (FIG. 14). All 18 piglets displayed either mono- or bi-allelic modifications for NANOS2, highlighting very high efficiencies of our approach.

Example 6

Generation of NANOS2 Edited Animals Via Somatic Cell Nuclear Transfer (SCNT)

Porcine fetal fibroblasts (PFF) were established from fetuses recovered from D35 pregnant Duroc pigs. A candidate male and female PFF line were nucleofected with a CMV promoter driven Cas9:GFP plasmid (Addgene) and PCR fragment consisting of hU6 promoter driven single-guide RNA targeting NANOS2 (SEQ ID NO:162). One day after nucleofection, the nucleofected cells were sorted singly into each well of a 96-well plate. The cells were fed with irradiated fibroblast conditioned growth medium, and allowed to form colonies. Following a week of culture, colonies begin to appear within the wells. The cells are clonally propagated, DNA extracted and screened for mutations using DNA sequencing. The cells are homozygous null for NANOS2 were cloned via somatic cell nuclear transfer to generate NANOS2 null male and female piglets. From these initial SCNT attempts, one surviving male, and three female piglets were generated, see FIG. 15.

Example 7

Testicular Phenotype of NANOS-2 Editied Animals

At 3 months of age, the testes of two bi-allelic Nanos2 homozygous knockout piglets were biopsied and examined morphologically. Based on observations of cross-sections from the biopsies using light microscopy (FIG. 16), the seminiferous cords are intact and somatic support cells are present. Although some germ cells are still present in the homozygous knockout animals, the number appears to be severely reduced compared to what is typically observed in a wild-type animal at this age. Indeed, some of the cords in homozygous animals appear to be devoid of germ cells. Also, the nuclei of remaining germ cells in homozygous animals appeared to be picnotic which is indicative of apoptosis. At 3 months of age, the seminiferous cords of wild-type pigs typically contain multiple layers of developing germ cells which is indicative of active spermatogenesis. None of the cords in Nanos2 knockout animal contain multiple layers of germ cells, strongly suggesting lack of an endogenous germline. Taken together, these observations suggest that the phenotype of Nanos2 loss-of-function is conserved in animals including loss of the male germline during early development leading to a Sertoli-cell only phenotype. Studies with mice have demonstrated that males with this phenotype are excellent hosts for regeneration of a donor germline following transplantation of spermatogonia.

Example 8

Transplantations with Nanos2 Homozygous Knockout Recipients

At 4 months of age, two homozygous knockout piglets received transplantations of spermatogonia isolated from the testes of a 21 day old Duroc donor male piglet. Briefly, the donor cells were suspended in 1 ml volumes of injection media at $1.4 \times 10^6$ cells/ml and 600-900 ul of volume was infused into the seminiferous tubules via ultrasound guided injection into the rete testis. One testis of each animal was transplanted with donor cells and the contralateral testis was left as a non-injected control.

Example 9

```
NANOS Genes
NANOS1 Sus scrofa
                                                                SEQ ID NO: 6
MEAFPWAPRSPRRGRVPPPMALVPSARYVSAQGPAHPQPFSSWNDYLGLATLITK

AVDGEPRFGCARGEDGGGGGGSPPSSSSSSCCSPHAGAGPGALGPALGPPDYDED

DDDDSDEPGSRGRYLGGTLELRALELCADPSEAGLLEERFAELSPFAGRATAVLLG

WAPATAATAEAAPREERAPAWAAEPRLHAAFGAAGARLLKPELQVCVFCRNNKE

AVALYTTHILKGPDGRVLCPVLRRYTCPLCGASGDNAHTIKYCPLSKVPPPRSVRD

GLPGKKLR

ORIGIN
                                                                SEQ ID NO: 5
     1  cgcaggggc  agggccgcgg  cagcgaggcc  gggggcggg  gaggagcggg  gcccgataaa 61  aggcagcgag  gcggccccac  cccgctgcag  gccggcgggc  aggctcggcg  cgtcctttcc 121  gtccggcccg  cgccggcggc  ggggaggcgg  cgcgcgcggc  ccgcagcccg  cccatggagg 181  ctttcccctg  ggcgccccgc  tcgccccgcc  gcggccgcgt  ccccccgccc  atggcgctcg 241  tgcccagcgc  ccgctacgtg  agcgcccagg  gcccggcgca  cccgcaaccc  ttcagctcgt 301  ggaacgacta  cctgggactc  gccacgctca  tcaccaaggc  ggtggacggc  gagccgcgct 361  ttggctgcgc  ccgcggcgag  gacggcggcg  gcggcggcgg  ctccccaccc  tcctcttcct 421  cctcgtcgtg  ctgctccccc  cacgcggggg  ccgggcctgg  ggcgctgggg  cccgcgctgg
```

-continued

```
 481 ggccacccga ctacgacgag gacgacgacg acgacagcga cgagccgggg tcccggggcc
 541 gctacctggg gggcacgctg gagctgcgcg cgctggagct gtgcgcggac ccctcggagg
 601 ccgggctgct ggaggagcgc ttcgccgagc tgagcccgtt cgcgggtcgc gccaccgctg
 661 tgctgctggg ctgggcaccc gccactgccc caccgccga gcggcaccg cgcgaggagc
 721 gggccccggc gtgggcggcc gagccccggc tgcacgcagc ctttggggcg gccggcgccc
 781 ggctgctcaa gcccgagctg caggtgtgtg tgttttgccg gaacaacaag gaggcggtgg
 841 cgctctacac cacccacatc ttgaagggac ccgacgggcg agtgctgtgc cccgtgctgc
 901 gccgctacac gtgtcccctg tgcggcgcca gcggcgacaa cgcgcacacc atcaagtact
 961 gcccgctctc caaagtgccg ccgccgcgca cgtcaggga cggcctgccc ggcaagaagc
1021 tgcgctgagg gcccggactc cggtctgcta ctgccacctg acgccaccag gtcgccgcc
1081 tgcccaatgt ctagtttggc ctgcgcacca tctctctctc tcgctgctga ggagcgtgga
1141 gctcagctgt tggttgaact tgagatgtac tgatttttt ttttttttt tcaaaagaac
1201 ccggcggtac tgagtccttt cctgtcgaag agcgcttaag actagaagct aaaatcttga
1261 tttgtttatc tctagtttgt gcacatccag acggtgaagg ctgggtgttc gttccactaa
1321 ctgaaatgtg gcaacttaga agtgtttatt tactctatac gtcaacctat tttagatgcg
1381 catcagtata tgaaattgtc tcaatctaat cttggatgtt taattttatg aatggaggca
1441 ctttactagg cctagaatat tttttaaaa gcctctaaac tgaacttaac tggcgatttt
1501 atggaatgtc agcaaaatga cttttattgt ttgaaacaag taataatatt tctgttgtcc
1561 ttaatcagtt attctaattc caggtgaagc aaccctcacc tgcctggtag catcattaag
1621 tgaaggctta gtaaactttc cagtgttagt ttgggtgggt gttccccccg tggcttgttt
1681 ctgtcctagc tggaggtgta aagatgtaca atctgtggca ggtagaatac agctccttat
1741 ccttttatgt accacatctt ttattactga acgagcaact agcgtttccc atctttcaaa
1801 gtcgtgccag gttatataat attgtgtata cacttggaaa tggtgctgtt taaaagaatt
1861 tgtgtattta tacagtaaca gtatatgaat tcattaatct tgtctt
```

NANOS2 Sus Scrofa

SEQ ID NO: 2

MQLPPFDMWKDYFNLSQVVLGLIQNRRQGPEAPGTGEPRPEPPLEQDQGPGERGA

SGGLATLCNFCKHNGESRHVYSSHQLKTPEGVVVCPILRHYVCPLCGATGDQAHT

LKYCPLNGGQQSLYRRSGRNSAGRKVKR (CRISPR target site is underlined)

SEQ ID NO: 1

```
   1 atgcagctgc cacccttga catgtggaag gactacttca acctgagcca ggtggtgttg
  61 ggactgatcc agaatcgtcg acaagggcca gaggccccgg gcaccgggga gccaagacct
 121 gagccccac tggagcagga ccaggcccg ggagagcggg gggccagcgg ggggctggcc
 181 accctgtgca actttttgcaa acacaatggg gaatctcgcc acgtgtactc ctcgcaccag
 241 ctgaagacac cggagggcgt ggtggtgtgt cccatcctac gacactatgt gtgtcccctg
 301 tgcggggcca ccggtgacca ggctcacaca ctcaagtact gcccgctcaa cggcggccag
 361 cagtctctct atcgccgcag tgggcgcaat tcagccggcc gcaaggtcaa cgctga
```

NANOS3 Sus scrofa

SEQ ID NO: 4

MHSFGRCIFGGAAASPPVTIRNLPQPAPPSSHPLGGIRRELTAQTPGLQREKGRGRG

KGIEGRSLGWLGFFSLSALSPGTLCPAMGTFNLWTDYLGLARLVGALRGEEEPETR

LDPQPAPVPGPEGQRPSPESSPAPERLCSFCKHNGESRAIYQSHVLKDEAGRVLCPI

-continued

LRDYVCPQCGATRERAHTRRFCPLTSQGYTSVYSYTTRNSAGKKLARPDKARTQD

SGHRRGGGGGASTGSKGAGKSSGTSPSPCCPSTSA

SEQ ID NO: 3
```
   1 cagcccaccc agggaccatg cattcctttg gcaggtgcat ttttggagga gcagcagcaa
  61 gccccctgt gacaataagg aacctcccac agcctgctcc tccctcttca cccccttg
 121 gaggtataag gagggaactg acagcccaga ctcctgggct ccagagagag aaagggaggg
 181 gcaggggaa ggggatagaa ggacgatctt tggggtggct gggtttcttc tctctctctg
 241 cccctttcacc tggtacactt tgcccagcca tggggacctt caacctgtgg acagattacc
 301 tgggtttggc acgcctggtg ggggctctgc gtggggaaga ggaacctgag acgaggctgg
 361 accccagcc agcaccagtg ccaggaccag agggtcagag gcccagcccg gaatcctcac
 421 cagctcctga acgcctgtgc tctttctgca aacataatgg cgaatcccgg ccatctacc
 481 agtcccacgt gctcaaggat gaagcgggcc gagttctgtg ccccattctt cgagactacg
 541 tgtgccccca gtgcggtgcc acacgcgagc gtgcccatac ccgccgcttc tgccctctca
 601 ccagccaggg ctacacctct gtctacagct acaccacccg caactcggcc ggcaagaagc
 661 tggcccgccc ggacaaggcg aggacacagg actctggaca tcggcgagga ggaggaggag
 721 gaggtgccag cacaggttcc aaaggtgccg ggaagtcttc tggaacttct ccgtctccct
 781 gctgtccctc cacttctgcc taagaggctg gcgcgagcag gacggagatg ctgccttcac
 841 ctggggatgg ggacccaggc tcagtggagg ctgggtttca gggacgacct accttcgcg
 901 gatccgcccc tgcccccagc ctgggagccc tgcaagggag ccaggcctgg aagctcggcc
 961 aaaagagagc cgctcctttc tccccatctc ccaccccaag aaaggaggtg gtcctctggc
1021 aaccctgccc tccttcccca gcgctgggca cccagttagc actcaataaa tac
```

BOVINE NANOS2 NM_001281904

SEQ ID NO: 10

MQLPPFDMWKDYFNLSQVVLALIQSRGQGLETQGTGEPRPGPHVEQDQGQGGRG

AGGGLATLCNFCKHNGESRHVYSSHQLKTPEGVVVCPILRHYVCPLCGATGDQA

HTLKYCPLNGGQQSLYRRSGRNSAGRKVKR

SEQ ID NO: 9
```
   1 tcagctgctc ctgtctgcgg gcccccagcc cacttctctc cagccaccca ccaccaacac
  61 tcccccgggt gccatgcagc tgccacccct tgacatgtgg aaggactact tcaacctgag
 121 ccaagtggtg ctggcactga tccagagtcg ggggcaaggg ttggagaccc aagggactgg
 181 ggagccgaga cccgggcccc atgtggagca ggatcagggg cagggcggac gcggggctgg
 241 cgggggcctg gccacccctgt gcaactttg caaacacaat ggagagtctc gccacgtgta
 301 ctcctcacac cagctgaaga ccccggaggg cgtggtggtg tgtcccattc tgcggcatta
 361 tgtatgtccc ctgtgcgggg ccaccgggga ccaggcccac acactcaagt actgcccact
 421 caacggagga cagcagtctc tctaccgccg cagtgggcgc aactcagccg gccgcaaggt
 481 caagcgctga agaccgtcag gtacccaccc gctgcagccc caaccctccc tggttcagcc
 541 ctcccaag
```

NANOS 1 bovine
XM_005225796

SEQ ID NO: 12

AAAAATAEAAPREERAPAWAAEPKLHAASGAAAARLLKPELQVCVFCRNNKEA

VALYTTHILKGPDGRVLCPVLRRYTCPLCGASGDNAHTIKYCPLSKVPPPPAARPP

PRSARDGLPGKKLR

SEQ ID NO: 11

-continued

```
   1 gccgccgccg cggccaccgc cgaagcagca ccgcgagagg agcgggcccc ggcgtgggcg
  61 gccgagccca agctgcacgc cgcctccggg gcggccgccg cccggctgct caagcccgag
 121 ctgcaggtgt gcgtgttttg ccggaacaac aaggaggcgg tggcgctcta caccacccac
 181 atcctgaagg gacccgacgg gcgggtgctg tgcccgtgc tgcgccgta cacgtgtccc
 241 ctgtgcggtg ccagcggcga caacgcgcac accatcaagt actgcccgct tccaaagtg
 301 ccgccgccgc ctgcagcccg cccgccgccg cgcagcgccc gggacggcct gcccggcaag
 361 aagctgcgct aagggcccgg accccggtct gctgctgcca cctgatgcca ctggggtagc
 421 cgcccgccca ctctcgtgtt tggtctgcgc accatctctt cctcgctgcc ggggagtgtg
 481 gagctcgtct tggttttcc agaggaagcc gacggtaccg agtatttcc taacgaagag
 541 cagttgagac tagacgttaa aattttgatt aatgtttcta gtttgtgcac atccagatgg
 601 tgaaggctgg gtattccact aactgaaatg tggcaactta gaggcgctgt ggtttattta
 661 tacgtcgacc tattttagat gcgcatcagt atgaaattgt ctcagtctaa tcttggatgt
 721 ttaattttat gaatggaggc actttactag gtctagaata ttttttaaa agcctctcaa
 781 ctgaacttaa aactggcgat tttatggagt gtcagcaaaa tgactatttt attgtctgaa
 841 acaatatttc tgttgtcctt acccagttgt aattccaggt gaagccctgc gtggtagcat
 901 cattaagtga agacttggta tgctttacag tgttagtttg ggtgggtgtt ccctccttgt
 961 ggcttgtttt tgtcctagct ggagatgtat aaaatgtaca atttgtaggt agcaggtaga
1021 atacagctca tgtaccagat cttttatta ctgaacgagc aactactacc gttttcccc
1081 tttaaaaata gtgccaagtt ataatcatat tgtgtataca cttgaaaatg gtgctgttta
1141 aaaaaattgt gtatttatac agtaacagta tatgaattca ttaaccttgc ctttaactct
1201 acttggcttt ttcttatgc cccttcctat tccagttctt caaaaatatg tgatacttaa
1261 gatcaaacgg gtgcaataac tcattcactc tgaattgctc catttcaggg tctctaaata
1321 gtggaaatct cattccagct gttgcctctc agactaaatg taagatggaa tcctttgagc
1381 tctggaaggt taatgaaaca actggtgttc aggaaggttc cactctggac tgtgtcagct
1441 ttaaaccatc acagaagtcc tcaaaccagt ataagtacca attaaaggaa ctgactgggt
1501 gtaggggggg taacacaagg aacacagcct ccatctattg tgttcccatt ctcattagaa
1561 gacaacccct ctggaatccc accagttatt ttcatcggtg agattaaatc taatcttggg
1621 caaa
```

BOVINE NANOS1 (ALT)
XM_001787922

SEQ ID NO: 14

RYVSTQGPAHPQPFSSWNDYLGLATLITKAVDGEPRFGCARGGDGGGDGSPPSSSS
SSCCSPHVGAGPGALGPALGPPDYDEDDDDDDSDDPGSRSRYLGGALELRALELC
ADPAEAGLLEERFAELSPFAGRAAAVLLGCAPAAAAAATAEAAPREERAPAWAA
EPKLHAASGAAAARLLKPELQVCVFCRNNKEAVALYTTHILKGPDGRVLCPVLRR
YTCPLCGASGDNAHTIKYCPLSKVPPPPAARPPPRSARDGLPGKKLR

SEQ ID NO: 13

```
   1 cgctacgtga gcacccaggg cccggcgcac ccgcagccct tcagctcgtg gaacgactat
  61 ctgggactcg ccacgctcat caccaaggcg gtggacggcg agccgcgctt cggctgcgcc
 121 cgcggcgggg acgcggcgg ggacggctcc ccgccttctt cttcctcctc gtcgtgctgc
 181 tccccccacg tgggggccgg gcctggggcg ctggggcccg cctggggcc gcccgactac
 241 gacgaggacg acgacgacga cgacagcgac gatccggggt cccggagccg ctacctgggg
 301 ggcgcgctgg agctgcgcgc gctggagctg tgcgcggacc ctgccgaggc cgggctgctg
```

```
   361 gaggagcgtt tcgctgagct gagcccgttc gctggtcgcg ccgctgccgt gcttctgggc 421 tgcgcaccct ccgccgccgc cgcggccacc gccgaagcag caccgcgaga ggagcgggcc 481 ccggcgtggg cggccgagcc caagctgcac gccgcctccg gggcggccgc cgcccggctg 541 ctcaagcccg agctgcaggt gtgcgtgttt tgccggaaca caaggaggc ggtggcgctc 601 tacaccaccc acatcctgaa gggacccgac gggcgggtgc tgtgccccgt gctgcgccgg 661 tacacgtgtc cctgtgcgg tgccagcggc gacaacgcgc acaccatcaa gtactgcccg 721 ctttccaaag tgccgccgcc gcctgcagcc cgcccgccgc cgcgcagcgc ccgggacggc 781 ctgcccggca agaagctgcg ctaagggccc ggacccggt ctgctgctgc acctgatgc 841 cactgggta gccgcccgcc cactctcgtg tttggtctgc gcaccatctc ttcctcgctg 901 ccggggagtg tggagctcgt cttggttttt ccagaggaag ccgacggtac cgagtatttt 961 cctaacgaag agcagttgag actagacgtt aaaattttga ttaatgtttc tagtttgtgc 1021 acatccagat ggtgaaggct gggtattcca ctaactgaaa tgtggcaact tagaggcgct 1081 gtggtttatt tatacgtcga cctattttag atgcgcatca gtatgaaatt gtctcagtct 1141 aatcttggat gtttaatttt atgaatggag gcactttact aggtctagaa tatttttta 1201 aaagcctctc aactgaactt aaaactggcg attttatgga gtgtcagcaa aatgactatt 1261 ttattgtctg aaacaatatt tctgttgtcc ttacccagtt gtaattccag gtgaagccct 1321 gcgtggtagc atcattaagt gaagacttgg tatgctttac agtgttagtt tgggtgggtg 1381 ttccctcctt gtggcttgtt tttgtcctag ctggagatgt ataaaatgta caatttgtag 1441 gtagcaggta gaatacagct catgtaccag atcttttat tactgaacga gcaactacta 1501 ccgttttcc cctttaaaaa tagtgccaag ttataatcat attgtgtata cacttgaaaa 1561 tggtgctgtt taaaaaatt gtgtatttat acagtaacag tatatgaatt cattaaccctt 1621 gcctttaact ctacttggct ttttctttat gccccttcct attccagttc ttcaaaaata 1681 tgtgatactt aagatcaaac gggtgcaata actcattcac tctgaattgc tccatttcag 1741 ggtctctaaa tagtgaaat ctcattccag ctgttgcctc tcagactaaa tgtaagatgg 1801 aatcctttga gctctggaag gttaatgaaa caactggtgt tcaggaaggt tccactctgg 1861 actgtgtcag cttaaaacca tcacagaagt cctcaaacca gtataagtac caattaaagg 1921 aactgactgg gtgtaggggg ggtaacacaa ggaacacagc ctccatctat tgtgttccca 1981 ttctcattag aagacaaccc ttctggaatc ccaccagtta ttttcatcgg tgagattaaa 2041 tctaatcttg ggcaaa
```

All references cited herein are incorporated herein by reference in their entirety. Examples disclosed herein are provided by way of exemplification and are not intended to limit the scope of the invention.

TABLE OF SEQUENCES

| SEQ | TYPE | DESCRIPTION |
| --- | --- | --- |
| SEQ ID NO: 1 | nucleotide | *sus scrofa* NANOS2 |
| SEQ ID NO: 2 | protein | *Sus scrofa* NANOS2 |
| SEQ ID NO: 3 | nucleotide | *sus scrofa* NANOS3 |
| SEQ ID NO: 4 | protein | *Sus scrofa* NANOS3 |
| SEQ ID NO: 5 | nucleotide | *sus scrofa* NANOS1 |
| SEQ ID NO: 6 | protein | *Sus scrofa* NANOS1 |
| SEQ ID NO: 7 | nucleotide | 2nd sgRNA FIG. 10 |
| SEQ ID NO: 8 | nucleotide | sgRNA FIG. 10 |
| SEQ ID NO: 9 | nucleotide | bovine NANOS2 |
| SEQ ID NO: 10 | protein | bovine NANOS2 |
| SEQ ID NO: 11 | nucleotide | bovine NANOS3 |
| SEQ ID NO: 12 | protein | bovine NANOS3 |
| SEQ ID NO: 13 | nucleotide | bovine NANOS3 (alt) |
| SEQ ID NO: 14 | protein | bovine NANOS3 (alt) |
| SEQ ID NO: 15 | nucleotide | FIG. 3A U6 promoter guide sequence and scaffold |
| SEQ ID NO: 16 | nucleotide | FIG. 3B U6 promoter guide sequence and scaffold |
| SEQ ID NO: 17 | nucleotide | FIG. 3C CRISPR construct |
| SEQ ID NO: 18 | nucleotide | FIG. 3C U6 |
| SEQ ID NO: 19 | nucleotide | FIG. 3C target |
| SEQ ID NO: 20 | nucleotide | FIG. 3C gRNA scaffold |
| SEQ ID NO: 21 | nucleotide | FIG. 3C terminal |

-continued

TABLE OF SEQUENCES

| SEQ | TYPE | DESCRIPTION |
|---|---|---|
| SEQ ID NO: 22 | nucleotide | FIG. 5B PX458 |
| SEQ ID NO: 23 | nucleotide | FIGS. 5B hu6 |
| SEQ ID NO: 24 | nucleotide | FIG. 5B gRNA scaffold |
| SEQ ID NO: 25 | nucleotide | FIGS. 5B terminal |
| SEQ ID NO: 26 | nucleotide | NANOS FIG. 10A |
| SEQ ID NO: 27 | nucleotide | NN6-1 FIG. 10A |
| SEQ ID NO: 28 | nucleotide | NN7-1 and NN7-2 FIG. 10A |
| SEQ ID NO: 29 | nucleotide | NANOS FIG. 9D |
| SEQ ID NO: 30 | nucleotide | N1-1 FIG. 9D |
| SEQ ID NO: 31 | nucleotide | N1-2 FIG. 9D |
| SEQ ID NO: 32 | nucleotide | N3-2 FIG. 9D |
| SEQ ID NO: 33 | nucleotide | N3-3 FIG. 9D |
| SEQ ID NO: 34 | nucleotide | N5-2 FIG. 9D |
| SEQ ID NO: 35 | nucleotide | N5-3 FIG. 9D |
| SEQ ID NO: 36 | nucleotide | N6-1 FIG. 9D |
| SEQ ID NO: 37 | nucleotide | N7-2 FIG. 9D |
| SEQ ID NO: 38 | nucleotide | N7-3 FIG. 9D |
| SEQ ID NO: 39 | nucleotide | N10-2 FIG. 9D |
| SEQ ID NO: 40 | nucleotide | N11-2 FIG. 9D |
| SEQ ID NO: 41 | nucleotide | N12-2 FIG. 9D |
| SEQ ID NO: 42 | nucleotide | N12-3 FIG. 9D |
| SEQ ID NO: 43 | nucleotide | FIG. 5C PX458 |
| SEQ ID NO: 44 | nucleotide | NANOS2 FIG. 10B |
| SEQ ID NO: 45 | nucleotide | N3-1-3 FIG. 10B |
| SEQ ID NO: 46 | nucleotide | N3-2-3 FIG. 10B |
| SEQ ID NO: 47 | nucleotide | N3-6-2 FIG. 10B |
| SEQ ID NO: 48 | nucleotide | N3-7-3 FIG. 10B |
| SEQ ID NO: 49 | nucleotide | N3-8-3 FIG. 10B |
| SEQ ID NO: 50 | nucleotide | N3-10-2 FIG. 10B |
| SEQ ID NO: 51 | nucleotide | N-3-12-2 FIG. 10B |
| SEQ ID NO: 52 | nucleotide | N3-12-3 FIG. 10B |
| SEQ ID NO: 53 | nucleotide | FIG. 11 sgRNA1 |
| SEQ ID NO: 54 | nucleotide | FIG. 11 sgRNA2 |
| SEQ IN NO: 55 | nucleotide | FIG. 11 NANOS |
| SEQ ID NO: 56 | nucleotide | FIG. 11 N2-3 |
| SEQ ID NO: 57 | nucleotide | FIG. 11 N3-1 |
| SEQ ID NO: 58 | nucleotide | FIG. 11 N4-2 |
| SEQ ID NO: 59 | nucleotide | FIGS. 11 N5-2 |
| SEQ ID NO: 60 | nucleotide | FIG. 11 N6-3 |
| SEQ ID NO: 61 | nucleotide | FIGS. 11 N7-1 |
| SEQ ID NO: 62 | nucleotide | FIG. 12 nt |
| SEQ ID NO: 63 | amino acid | FIG. 12 NANOS CDS |
| SEQ ID NO: 64 | nucleotide | FIG. 12 oSL86 |
| SEQ ID NO: 65 | nucleotide | FIG. 12 pSL36 or 37 |
| SEQ ID NO: 66 | nucleotide | FIG. 12 pSL34 or 35 |
| SEQ ID NO: 67 | nucleotide | FIG. 12 pSL32 or 33 |
| SEQ ID NO: 68 | nucleotide | FIG. 12 pSL38 or 39 |
| SEQ ID NO: 69 | nucleotide | FIG. 12 pSL39 or 40 |
| SEQ ID NO: 70 | nucleotide | FIG. 12 pSL41 or 42 |
| SEQ ID NO: 71 | nucleotide | FIG. 12 pSL43 or 44 |
| SEQ ID NO: 72 | nucleotide | FIG. 12 pSL45 or 46 |
| SEQ IN NO: 73 | nucleotide | FIG. 12 pSL47 or 48 |
| SEQ ID NO: 74 | nucleotide | FIG. 12 oSL87 |
| SEQ ID NO: 75 | nucleotide | 18:18:18 TALEN |
| SEQ ID NO: 76 | nucleotide | TALEN primer 1 |
| SEQ ID NO: 77 | nucleotide | TALEN primer 2 |
| SEQ ID NO: 78 | nucleotide | 18:16:18 TALEN |
| SEQ ID NO: 79 | nucleotide | TALEN primer 3 |
| SEQ ID NO: 80 | nucleotide | TALEN primer 4 |
| SEQ ID NO: 81 | nucleotide | 18:17:18 TALEN |
| SEQ ID NO: 82 | nucleotide | TALEN primer 5 |
| SEQ ID NO: 83 | nucleotide | TALEN primer 6 |
| SEQ ID NO: 84 | nucleotide | oSL9 |
| SEQ ID NO: 85 | nucleotide | oSL10 |
| SEQ ID NO: 86 | nucleotide | CRISPR target |
| SEQ ID NO: 87 | nucleotide | CRISPR target |
| SEQ ID NO: 88 | nucleotide | oSL48 |
| SEQ ID NO: 89 | nucleotide | oSL49 |
| SEQ ID NO: 90 | nucleotide | oSL50 |
| SEQ ID NO: 91 | nucleotide | oSL51 |
| SEQ ID NO: 92 | nucleotide | oSL52 |
| SEQ ID NO: 93 | nucleotide | oSL53 |
| SEQ ID NO: 94 | nucleotide | oSL54 |
| SEQ ID NO: 95 | nucleotide | oSL55 |
| SEQ ID NO: 96 | nucleotide | oSL56 |
| SEQ ID NO: 97 | nucleotide | oSL57 |
| SEQ ID NO: 98 | nucleotide | oSL58 |
| SEQ ID NO: 99 | nucleotide | oSL59 |
| SEQ IN NO: 100 | nucleotide | oSL60 |
| SEQ ID NO: 101 | nucleotide | oSL61 |
| SEQ ID NO: 102 | nucleotide | oSL62 |
| SEQ ID NO: 103 | nucleotide | oSL63 |
| SEQ ID NO: 104 | nucleotide | oSL64 |
| SEQ ID NO: 105 | nucleotide | oSL65 |
| SEQ ID NO: 106 | nucleotide | oSL66 |
| SEQ ID NO: 107 | nucleotide | oSL67 |
| SEQ ID NO: 108 | nucleotide | oSL68 |
| SEQ ID NO: 109 | nucleotide | oSL69 |
| SEQ ID NO: 110 | nucleotide | oSL70 |
| SEQ ID NO: 111 | nucleotide | oSL71 |
| SEQ ID NO: 112 | nucleotide | oSL72 |
| SEQ ID NO: 113 | nucleotide | oSL73 |
| SEQ ID NO: 114 | nucleotide | oSL74 |
| SEQ ID NO: 115 | nucleotide | oSL75 |
| SEQ ID NO: 116 | nucleotide | oSL76 |
| SEQ ID NO: 117 | nucleotide | pSL32 & pSL38: WT FIG. 8a |
| SEQ ID NO: 118 | nucleotide | pSL32 & pSL38 Clone 1 FIG. 8a |
| SEQ ID NO: 119 | nucleotide | pSL32 & pSL38 Clone 2 FIG. 8a |
| SEQ ID NO: 120 | nucleotide | pSL32 & pSL38 Clone 3 FIG. 8a |
| SEQ ID NO: 121 | nucleotide | pSL32 & pSL38 Clone 4 FIG. 8a |
| SEQ ID NO: 122 | nucleotide | pSL32 & pSL38 Clone 5 FIG. 8a |
| SEQ ID NO: 123 | nucleotide | pSL32 & pSL39: WT FIG. 8b |
| SEQ ID NO: 124 | nucleotide | pSL32 & pSL39: Clone 1 FIG. 8b |
| SEQ ID NO: 125 | nucleotide | pSL32 & pSL39: Clone 2 FIG. 8b |
| SEQ ID NO: 126 | nucleotide | pSL32 & pSL39: Clone 3 FIG. 8b |
| SEQ ID NO: 127 | nucleotide | pSL32 & pSL39: Clone 4 FIG. 8b |
| SEQ ID NO: 128 | nucleotide | pSL32 & pSL39: Clone 5 FIG. 8b |
| SEQ ID NO: 129 | nucleotide | pSL32 & pSL42 WT FIG. 8c |
| SEQ ID NO: 130 | nucleotide | pSL32 & pSL42 Clone 1 FIG. 8c |
| SEQ ID NO: 131 | nucleotide | pSL32 & pSL42 Clone 2 FIG. 8c |
| SEQ ID NO: 132 | nucleotide | pSL32 & pSL42 Clone 3 FIG. 8c |
| SEQ ID NO: 133 | nucleotide | pSL32 & pSL42 Clone 4 FIG. 8c |
| SEQ ID NO: 134 | nucleotide | pSL32 & pSL42 Clone 5 FIG. 8c |
| SEQ ID NO: 135 | nucleotide | pSL33 & pSL38 WT FIG. 8d |
| SEQ ID NO: 136 | nucleotide | pSL33 & pSL38 Clone 1 FIG. 8d |
| SEQ ID NO: 137 | nucleotide | pSL33 & pSL38 Clone 2 Fig. 8d |
| SEQ ID NO: 138 | nucleotide | pSL33 & pSL38 Clone 3 FIG. 8d |
| SEQ ID NO: 139 | nucleotide | pSL33 & pSL38 Clone 4 FIG. 8d |
| SEQ ID NO: 140 | nucleotide | pSL33 & pSL38 Clone 5 FIG. 8d |
| SEQ ID NO: 141 | nucleotide | pSL33 & pSL39 WT FIG. 8e |
| SEQ ID NO: 142 | nucleotide | pSL33 & pSL39 Clone 1 FIG. 8e |
| SEQ ID NO: 143 | nucleotide | pSL33 & pSL39 Clone 2 FIG. 8e |
| SEQ ID NO: 144 | nucleotide | pSL33 & pSL39 Clone 3 FIG. 8e |
| SEQ ID NO: 145 | nucleotide | pSL33 & pSL39 Clone 4 FIG. 8e |
| SEQ ID NO: 146 | nucleotide | pSL33 & pSL39 Clone 5 FIG. 8e |
| SEQ ID NO: 147 | nucleotide | pSL33 & pSL42 WT FIG. 8f |
| SEQ ID NO: 148 | nucleotide | pSL33 & pSL42 Clone 1 FIG. 8f |
| SEQ ID NO: 149 | nucleotide | pSL33 & pSL42 Clone 2 FIG. 8f |
| SEQ ID NO: 150 | nucleotide | pSL33 & pSL42 Clone 3 FIG. 8f |
| SEQ ID NO: 151 | nucleotide | pSL33 & pSL42 Clone 4 FIG. 8f |
| SEQ ID NO: 152 | nucleotide | pSL33 & pSL42 Clone 5 FIG. 8f |
| SEQ ID NO: 153 | nucleotide | oSL77 |
| SEQ ID NO: 154 | nucleotide | oSL78 |
| SEQ ID NO: 155 | nucleotide | oSL79 |
| SEQ ID NO: 156 | nucleotide | oSL80 |
| SEQ ID NO: 157 | nucleotide | oSL81 |
| SEQ ID NO: 158 | nucleotide | oSL82 |
| SEQ ID NO: 159 | nucleotide | oSL83 |
| SEQ ID NO: 160 | nucleotide | sgRNA FIG. 13A |
| SEQ ID NO: 161 | nucleotide | CRISPR Target FIG. 13B |
| SEQ ID NO: 162 | nucleotide | sgRNA FIG. 15 |
| SEQ ID NO: 163 | nucleotide | NANOS2 WT FIG. 14 |
| SEQ ID NO: 164 | nucleotide | NANOS2 pig 1-1 FIG. 14 |
| SEQ ID NO: 165 | nucleotide | NANOS2 pig 1-2 FIG. 14 |
| SEQ ID NO: 166 | nucleotide | NANOS2 pig 1-3 FIG. 14 |
| SEQ ID NO: 167 | nucleotide | NANOS2 pig 2-1 FIG. 14 |
| SEQ ID NO: 168 | nucleotide | NANOS2 pig 2-4 FIG. 14 |
| SEQ ID NO: 169 | nucleotide | NANOS2 pig 3-1 FIG. 14 |
| SEQ ID NO: 170 | nucleotide | NANOS2 pig 4-1 FIG. 14 |
| SEQ ID NO: 171 | nucleotide | NANOS2 pig 4-2 FIG. 14 |

TABLE OF SEQUENCES

| SEQ | TYPE | DESCRIPTION |
|---|---|---|
| SEQ ID NO: 172 | nucleotide | NANOS2 pig 10-1 FIG. 14 |
| SEQ ID NO: 173 | nucleotide | NANOS2 pig 10-2 FIG. 14 |
| SEQ ID NO: 174 | nucleotide | NANOS2 pig 11-1 FIG. 14 |
| SEQ ID NO: 164 | nucleotide | NANOS2 pig 11-4 FIG. 14 |
| SEQ ID NO: 176 | nucleotide | NANOS2 pig 12-1 FIG. 14 |
| SEQ ID NO: 177 | nucleotide | NANOS2 pig 12-2 FIG. 14 |
| SEQ ID NO: 178 | nucleotide | NANOS2 #1 piglet Allele-1 FIG. 14 |
| SEQ ID NO: 179 | nucleotide | NANOS2 #1 piglet Allele-2 FIG. 14 |
| SEQ ID NO: 180 | nucleotide | NANOS2 #2 piglet Allele-1 FIG. 14 |
| SEQ ID NO: 181 | nucleotide | NANOS2 #2 piglet Allele-2 FIG. 14 |
| SEQ ID NO: 182 | nucleotide | NANOS2 #3 piglet Allele-1 FIG. 14 |
| SEQ ID NO: 183 | nucleotide | NANOS2 #3 piglet Allele-2 FIG. 14 |
| SEQ ID NO: 184 | nucleotide | NANOS2 #4 piglet Allele-1 FIG. 14 |
| SEQ ID NO: 185 | nucleotide | NANOS2 #4 piglet Allele-2 FIG. 14 |
| SEQ ID NO: 186 | nucleotide | NANOS2 #5 piglet Allele-1 FIG. 14 |
| SEQ ID NO: 187 | nucleotide | NANOS2 #5 piglet Allele-2 FIG. 14 |
| SEQ ID NO: 188 | nucleotide | NANOS2 #6 piglet Allele-1 FIG. 14 |
| SEQ ID NO: 189 | nucleotide | NANOS2 #6 piglet Allele-2 FIG. 14 |
| SEQ ID NO: 164 | nucleotide | NANOS2 #7 piglet Allele-1 FIG. 14 |
| SEQ ID NO: 164 | nucleotide | NANOS2 #7 piglet Allele-2 FIG. 14 |
| SEQ ID NO: 192 | nucleotide | NANOS2 #8 piglet Allele-1 FIG. 14 |
| SEQ ID NO: 193 | nucleotide | NANOS2 #8 piglet Allele-2 FIG. 14 |
| SEQ ID NO: 194 | nucleotide | NANOS2 #9 piglet Allele-1 FIG. 14 |
| SEQ ID NO: 195 | nucleotide | NANOS2 #9 piglet Allele-2 FIG. 14 |
| SEQ ID NO: 196 | nucleotide | NANOS2 #10 piglet Allele-1 FIG. 14 |
| SEQ ID NO: 164 | nucleotide | NANOS2 #10 piglet Allele-2 FIG. 14 |
| SEQ ID NO: 198 | nucleotide | NANOS2 #11 piglet Allele-1 FIG. 14 |
| SEQ ID NO: 199 | nucleotide | NANOS2 #11 piglet Allele-2 FIG. 14 |
| SEQ ID NO: 200 | nucleotide | NANOS2 WT FIG. 15 |
| SEQ ID NO: 201 | nucleotide | NANOS2 male piglet A-1 FIG. 15 |
| SEQ ID NO: 202 | nucleotide | NANOS2 male piglet A-2 FIG. 15 |
| SEQ ID NO: 203 | nucleotide | NANOS2 female piglet A-1 FIG. 15 |
| SEQ ID NO: 204 | nucleotide | NANOS2 female piglet A-2 FIG. 15 |

What is claimed is:

1. A method of breeding porcine animals comprising:
modifying NANOS2 gene expression in a male porcine animal by an insertion or deletion (indel) mutation to form a homozygous NANOS2 gene knock out or a bi-allele NANOS2 gene knockout, so that NANOS2 protein function is reduced or eliminated, wherein the male porcine animal produces no germline cells but retains Sertoli cell function, and wherein the modified NANOS2 gene comprises SEQ ID NO: 27, 28, 30, 31, 33, 34, 36, 37, 38, 40, 41, 42, 45, 46, 48, 49, 51, 56, 57, 164, 165, 166, 167, 168, 169, 172, 176, 177, 180, 181, 184, 185, 186, 190, 192, 193, 195, 199, 201, 203, or 204;

transplanting donor spermatogonial stem cells (SSCs) to the male porcine animal so that spermatogenic colonies are generated; and introducing donor-derived sperm from the male porcine animal into a female porcine animal so that the female porcine animal becomes pregnant.

2. The method of claim 1, wherein the modifying comprises use of a NANOS2 guide RNA and a polypeptide that effects cleavage or integration of the NANOS2 target.

3. The method of claim 2, wherein the modifying is by use of RNA-guided CRISPR/Cas9.

4. The method of claim 1, wherein the modifying is by use of a TALEN, a zinc finger nuclease, and/or a recombinase fusion protein, wherein the recombinase fusion protein comprises a NANOS2 site-specific DNA binding domain polypeptide and a nuclease cleavage domain polypeptide.

5. The method of claim 1, wherein the male porcine animal comprises no exogenously introduced sequence.

6. The method of claim 1, wherein the donor SSCs are collected from a desired male donor.

7. The method of claim 6, wherein the donor SSCs are proliferated in vitro prior to transplanting.

8. The method of claim 1, wherein the introducing is by artificial insemination.

9. The method of claim 1, wherein the introducing is by natural mating.

10. The method of claim 1, wherein the transplanting comprises injection into the rete testis of the male porcine animal.

\* \* \* \* \*